US012293016B2

United States Patent
Lussier et al.

(10) Patent No.: US 12,293,016 B2
(45) Date of Patent: May 6, 2025

(54) LIGHT FIELD DEVICE, PIXEL RENDERING METHOD THEREFOR, AND ADJUSTED VISION PERCEPTION SYSTEM AND METHOD USING SAME

(71) Applicant: EVOLUTION OPTIKS LIMITED, Bridgetown (BB)

(72) Inventors: Guillaume Lussier, Montreal (CA); Raul Mihali, Westport, CT (US); Yaiza Garcia, Beaconsfield (CA); Matej Goc, Kingston (CA); Daniel Gotsch, Redwood City, CA (US)

(73) Assignee: EVOLUTION OPTIKS LIMITED, Christ Church (BB)

( * ) Notice: Subject to any disclaimer, the term of this patent is extended or adjusted under 35 U.S.C. 154(b) by 0 days.

(21) Appl. No.: 18/661,404

(22) Filed: May 10, 2024

(65) Prior Publication Data
US 2024/0295923 A1 Sep. 5, 2024

Related U.S. Application Data

(60) Continuation of application No. 18/343,575, filed on Jun. 28, 2023, now Pat. No. 12,019,799, which is a
(Continued)

(30) Foreign Application Priority Data

Oct. 22, 2018 (CA) .................................. CA 3021636

(51) Int. Cl.
*G06F 3/01* (2006.01)
*G02B 27/00* (2006.01)
(Continued)

(52) U.S. Cl.
CPC .......... *G06F 3/013* (2013.01); *G02B 27/0025* (2013.01); *G06F 3/04845* (2013.01); *G06T 3/40* (2013.01); *G06V 40/19* (2022.01)

(58) Field of Classification Search
CPC .... G06F 3/04845; G06F 3/013; G06F 3/0481; G06F 3/0487; G06T 15/06; G06T 3/40;
(Continued)

(56) References Cited

U.S. PATENT DOCUMENTS 5,032,754 A 7/1991 Iwao et al.
5,959,664 A 9/1999 Woodgate
(Continued)

FOREIGN PATENT DOCUMENTS

AU 2015100739 7/2015
CN 103026367 A 4/2013
(Continued)

OTHER PUBLICATIONS

"A Computational Light Field Display for Correcting Visual Aberrations," Huang, F.C., Technical Report No. UCB/EECS-2013-206, Electrical Engineering and Computer Sciences University of California at Berkeley, http://www.eecs.berkeley.edu/Pubs/TechRpts/2013/EECS-2013-206.html, Dec. 15, 2013.
(Continued)

*Primary Examiner* — Jack Dinh
(74) *Attorney, Agent, or Firm* — Knobbe, Martens, Olson & Bear, LLP

(57) ABSTRACT

Described are various embodiments of a device to subjectively assess a user's reduced visual acuity. In one embodiment, the device comprises: a digital display; a lenslet array disposed relative to the digital display to shape a light field emanating therefrom; and a hardware processor. The hardware processor operates on pixel data for respective optotypes to output respectively adjusted pixel data to be ren-
(Continued)

dered side-by-side by the digital display via the lenslet array so to respectively adjust user perception of the respective optotypes as rendered therethrough to thereby render, side-by-side, distinctly perceptively adjusted optotypes corresponding to respective visual corrections to subjectively assess the user's reduced visual acuity.

10 Claims, 32 Drawing Sheets

Related U.S. Application Data continuation of application No. 17/652,077, filed on Feb. 22, 2022, now Pat. No. 11,726,563, which is a division of application No. 17/302,392, filed on Apr. 30, 2021, now Pat. No. 11,287,883, which is a continuation-in-part of application No. PCT/US2020/058392, filed on Oct. 30, 2020, and a continuation-in-part of application No. 17/309,133, filed as application No. PCT/IB2020/057887 on Aug. 22, 2020, now Pat. No. 11,966,507, which is a continuation of application No. 16/810,143, filed on Mar. 5, 2020, now Pat. No. 10,761,604, which is a continuation-in-part of application No. 16/569,137, filed on Sep. 12, 2019, now Pat. No. 10,642,355, which is a continuation of application No. 16/510,673, filed on Jul. 12, 2019, now Pat. No. 10,474,235, which is a continuation of application No. 16/259,845, filed on Jan. 28, 2019, now Pat. No. 10,394,322, said application No. PCT/IB2020/057887 is a continuation-in-part of application No. PCT/IB2019/058955, filed on Oct. 21, 2019, said application No. 16/810,143 is a continuation-in-part of application No. 16/551,572, filed on Aug. 26, 2019, now Pat. No. 10,636,116, and a continuation-in-part of application No. PCT/IB2019/058955, filed on Oct. 21, 2019, said application No. PCT/US2020/058392 is a continuation-in-part of application No. 16/810,143, filed on Mar. 5, 2020, now Pat. No. 10,761,604.

(60) Provisional application No. 62/929,639, filed on Nov. 1, 2019.

(51) Int. Cl.
  *G06F 3/04845* (2022.01)
  *G06T 3/40* (2024.01)
  *G06V 40/19* (2022.01)

(58) Field of Classification Search
  CPC .......... G06V 40/19; G06G 3/001; G06G 3/04; G06G 2380/08; G06G 2354/00; G02B 27/0075; G02B 27/0025; G02B 27/0093
  See application file for complete search history.

(56) References Cited

U.S. PATENT DOCUMENTS

| | | |
|---|---|---|
| 6,192,341 B1 | 2/2001 | Becker et al. |
| 6,309,117 B1 | 10/2001 | Bunce et al. |
| 6,386,707 B1 | 5/2002 | Pellicano |
| 6,483,485 B1 | 11/2002 | Huang et al. |
| 6,536,907 B1 | 3/2003 | Towner et al. |
| 6,543,898 B1 | 4/2003 | Griffin et al. |
| 6,784,905 B2 | 8/2004 | Brown et al. |
| 6,809,704 B2 | 10/2004 | Kulas |
| 6,820,979 B1 | 11/2004 | Stark et al. |
| 6,876,758 B1 | 4/2005 | Polat et al. |
| 6,953,249 B1 | 10/2005 | Maguire, Jr. |
| 7,062,547 B2 | 6/2006 | Brown et al. |
| 7,147,605 B2 | 12/2006 | Ragauskas |
| 7,517,086 B1 | 4/2009 | Kürkure |
| 7,819,818 B2 | 10/2010 | Ghajar |
| 7,866,817 B2 | 1/2011 | Polat |
| 7,891,813 B2 | 2/2011 | Ogilvie |
| 7,973,850 B2 | 7/2011 | Ishiga |
| 8,089,512 B2 | 1/2012 | Okabe et al. |
| 8,098,440 B2 | 1/2012 | Jethmalani et al. |
| 8,164,598 B2 | 4/2012 | Kimpe |
| 8,231,220 B2 | 7/2012 | Baranton |
| 8,322,857 B2 | 12/2012 | Barbur et al. |
| 8,540,375 B2 | 9/2013 | Destain |
| 8,717,254 B1 | 5/2014 | Nave et al. |
| 8,783,871 B2 | 7/2014 | Pamplona et al. |
| 8,798,317 B2 | 8/2014 | Wu |
| 8,823,742 B2 | 9/2014 | Kweon |
| 8,857,984 B2 | 10/2014 | Clarke et al. |
| 8,967,809 B2 | 3/2015 | Kirschen et al. |
| 9,010,929 B2 | 4/2015 | Lewis |
| 9,041,833 B2 | 5/2015 | Hatakeyama |
| 9,052,502 B2 | 6/2015 | Caldeira et al. |
| 9,066,683 B2 | 6/2015 | Zhou |
| 9,104,233 B2 | 8/2015 | Alberth |
| 9,159,299 B2 | 10/2015 | Lee |
| 9,177,355 B1 | 11/2015 | Buchheit |
| 9,183,806 B2 | 11/2015 | Felt |
| 9,198,571 B2 | 12/2015 | Kiderman et al. |
| 9,301,680 B2 | 4/2016 | Fassi et al. |
| 9,307,940 B2 | 4/2016 | MacLullich et al. |
| 9,492,074 B1 | 11/2016 | Lee et al. |
| 9,642,522 B2 | 5/2017 | Samadani et al. |
| 9,844,323 B2 | 12/2017 | Pamplona et al. |
| 9,895,057 B2 | 2/2018 | Tumlinson |
| 10,058,241 B2 | 8/2018 | Patella et al. |
| 10,085,631 B2 | 10/2018 | Shimizu et al. |
| 10,182,717 B2 | 1/2019 | Lindig et al. |
| 10,206,566 B2 | 2/2019 | Skolianos et al. |
| 10,247,941 B2 | 4/2019 | Fürsich |
| 10,335,027 B2 | 7/2019 | Pamplona et al. |
| 10,345,590 B2 | 7/2019 | Samec et al. |
| 10,394,322 B1 | 8/2019 | Gotsch |
| 10,420,467 B2 | 9/2019 | Krall et al. |
| 10,548,473 B2 | 2/2020 | Escalier et al. |
| 10,761,604 B2 | 9/2020 | Gotsch et al. |
| 11,287,883 B2 | 3/2022 | Lussier |
| 2002/0024633 A1 | 2/2002 | Kim et al. |
| 2002/0099305 A1 | 7/2002 | Fukushima et al. |
| 2006/0119705 A1 | 6/2006 | Liao |
| 2007/0247522 A1 | 10/2007 | Holliman |
| 2008/0309764 A1 | 12/2008 | Kubota et al. |
| 2009/0290132 A1 | 11/2009 | Shevlin |
| 2010/0156214 A1 | 6/2010 | Yang |
| 2010/0277693 A1 | 11/2010 | Martinez-Conde et al. |
| 2010/0298735 A1 | 11/2010 | Suffin |
| 2011/0019056 A1 | 1/2011 | Hirsch et al. |
| 2011/0122144 A1 | 5/2011 | Gabay |
| 2011/0157180 A1 | 6/2011 | Burger et al. |
| 2011/0268868 A1 | 11/2011 | Dowski, Jr. et al. |
| 2012/0010474 A1 | 1/2012 | Olsen et al. |
| 2012/0113389 A1 | 5/2012 | Mukai et al. |
| 2012/0206445 A1 | 8/2012 | Chiba |
| 2012/0249951 A1 | 10/2012 | Hirayama |
| 2012/0254779 A1 | 10/2012 | Ollivierre et al. |
| 2012/0262477 A1 | 10/2012 | Buchheit |
| 2013/0027384 A1 | 1/2013 | Ferris |
| 2013/0096820 A1 | 4/2013 | Agnew |
| 2013/0120390 A1 | 5/2013 | Marchand et al. |
| 2013/0222652 A1 | 8/2013 | Akeley et al. |
| 2014/0028662 A1 | 1/2014 | Liao et al. |
| 2014/0055692 A1 | 2/2014 | Kroll et al. |
| 2014/0063332 A1 | 3/2014 | Miyawaki |
| 2014/0118354 A1 | 5/2014 | Pais et al. |
| 2014/0137054 A1 | 5/2014 | Gandhi et al. |
| 2014/0200079 A1 | 7/2014 | Bathiche et al. |
| 2014/0253876 A1 | 9/2014 | Klin et al. |
| 2014/0267284 A1 | 9/2014 | Blanche et al. |
| 2014/0268060 A1 | 9/2014 | Lee et al. |
| 2014/0282285 A1 | 9/2014 | Sadhvani et al. |

(56) References Cited

U.S. PATENT DOCUMENTS

| | | |
|---|---|---|
| 2014/0300711 A1 | 10/2014 | Kroon |
| 2014/0327750 A1 | 11/2014 | Malachowsky et al. |
| 2014/0327771 A1 | 11/2014 | Malachowsky et al. |
| 2014/0340390 A1 | 11/2014 | Lanman et al. |
| 2015/0049390 A1 | 2/2015 | Lanman et al. |
| 2015/0177514 A1 | 6/2015 | Maimone et al. |
| 2015/0185501 A1 | 7/2015 | Bakaraju et al. |
| 2015/0234187 A1 | 8/2015 | Lee |
| 2015/0234188 A1 | 8/2015 | Lee |
| 2015/0245766 A1 | 9/2015 | Rennaker et al. |
| 2015/0262424 A1 | 9/2015 | Tabaka et al. |
| 2015/0336511 A1 | 11/2015 | Ukeda |
| 2016/0042501 A1 | 2/2016 | Huang et al. |
| 2016/0103419 A1 | 4/2016 | Callagy et al. |
| 2016/0134815 A1 | 5/2016 | Ishiguro et al. |
| 2016/0260258 A1 | 9/2016 | Lo |
| 2016/0270656 A1 | 9/2016 | Samec et al. |
| 2016/0306390 A1 | 10/2016 | Vertegaal et al. |
| 2016/0335749 A1 | 11/2016 | Kano |
| 2017/0027435 A1 | 2/2017 | Boutinon et al. |
| 2017/0060399 A1 | 3/2017 | Hough et al. |
| 2017/0212352 A1 | 7/2017 | Cobb et al. |
| 2017/0227781 A1 | 8/2017 | Banerjee et al. |
| 2017/0302913 A1 | 10/2017 | Tonar et al. |
| 2017/0307898 A1 | 10/2017 | Vdovin et al. |
| 2017/0353717 A1 | 12/2017 | Zhou et al. |
| 2017/0365101 A1 | 12/2017 | Samec et al. |
| 2017/0365189 A1 | 12/2017 | Halpin et al. |
| 2018/0033209 A1 | 2/2018 | Akeley |
| 2018/0070820 A1 | 3/2018 | Fried et al. |
| 2018/0084245 A1 | 3/2018 | Lapstun |
| 2018/0136486 A1 | 5/2018 | Macnamara et al. |
| 2018/0203232 A1 | 7/2018 | Bouchier et al. |
| 2018/0252935 A1 | 9/2018 | Vertegaal et al. |
| 2018/0271741 A1 | 9/2018 | Diaz et al. |
| 2018/0290593 A1 | 10/2018 | Cho |
| 2018/0329485 A1 | 11/2018 | Carothers |
| 2018/0330652 A1 | 11/2018 | Perreault et al. |
| 2019/0125179 A1 | 5/2019 | Xu et al. |
| 2019/0150729 A1 | 5/2019 | Huang et al. |
| 2019/0175011 A1 | 6/2019 | Jensen et al. |
| 2019/0228586 A1 | 7/2019 | Bar-Zeev et al. |
| 2019/0246095 A1 | 8/2019 | Kishimoto |
| 2019/0246889 A1 | 8/2019 | Marin et al. |
| 2019/0293939 A1 | 9/2019 | Sluka |
| 2019/0310478 A1 | 10/2019 | Marin et al. |
| 2020/0012090 A1 | 1/2020 | Lapstun |
| 2020/0126180 A1 | 4/2020 | Gotsch |
| 2021/0271091 A1 | 9/2021 | Xu |
| 2021/0382307 A1 | 12/2021 | Sluka et al. |
| 2022/0187909 A1 | 6/2022 | Gotsch |
| 2022/0404689 A1 | 12/2022 | Sluka |
| 2022/0408070 A1 | 12/2022 | Hirt |

FOREIGN PATENT DOCUMENTS

| | | |
|---|---|---|
| CN | 109683335 A | 4/2019 |
| CN | 109788901 A | 5/2019 |
| CN | 109863533 A | 6/2019 |
| DE | 9410161 | 12/1994 |
| DE | 102004038822 | 3/2006 |
| DE | 102016212761 | 5/2018 |
| DE | 102018121742 | 3/2020 |
| DE | 102018129600 | 5/2020 |
| DE | 102019102373 | 7/2020 |
| EP | 2127949 | 12/2009 |
| EP | 1509121 | 9/2012 |
| EP | 2589020 | 5/2013 |
| EP | 2678804 | 1/2014 |
| EP | 2760329 | 8/2014 |
| EP | 2999393 | 3/2016 |
| EP | 2547248 | 5/2017 |
| EP | 3262617 | 1/2018 |
| EP | 3339943 | 6/2018 |
| EP | 3367307 | 12/2018 |
| EP | 3542206 | 9/2019 |
| EP | 2828834 | 11/2019 |
| EP | 3620846 | 3/2020 |
| EP | 3631770 | 4/2020 |
| EP | 3657440 | 5/2020 |
| EP | 3659109 | 6/2020 |
| EP | 3689225 | 8/2020 |
| EP | 3479344 | 12/2020 |
| EP | 3313263 | 12/2021 |
| EP | 4100780 B1 | 11/2024 |
| FR | 3059537 | 5/2019 |
| JP | 2003038443 | 2/2003 |
| WO | WO 2010116019 | 10/2010 |
| WO | WO 2011156721 | 12/2011 |
| WO | WO 2013166570 | 11/2013 |
| WO | WO 2014174168 | 10/2014 |
| WO | WO 2014197338 | 12/2014 |
| WO | WO 2015049402 | 4/2015 |
| WO | WO 2015162098 | 10/2015 |
| WO | WO 2017192887 | 11/2017 |
| WO | WO 2017218539 | 12/2017 |
| WO | WO 2018022521 | 2/2018 |
| WO | WO 2018092989 | 5/2018 |
| WO | WO 2018129310 | 7/2018 |
| WO | WO 2019002656 | 1/2019 |
| WO | WO 2021038421 | 8/2020 |
| WO | WO 2021087384 | 10/2020 |
| WO | WO 2021122640 | 6/2021 |
| WO | WO 2021209785 | 10/2021 |
| WO | WO 2022038400 | 2/2022 |
| WO | WO 2022112818 | 6/2022 |
| WO | WO 2022175716 | 8/2022 |
| WO | WO 2022254243 | 12/2022 |

OTHER PUBLICATIONS

Agus M. et al., "GPU Accelerated Direct Volume Rendering on an Interactive Light Field Display", EUROGRAPHICS 2008, vol. 27, No. 2, 2008.

Burnett T., "FoVI3D Extreme Multi-view Rendering for Light-field Displays", GTC 2018 (GPU Technology Conference), Silicon Valley, 2018.

Ciuffreda, Kenneth J., et al., Understanding the effects of mild traumatic brain injury on the pupillary light reflex, Concussion (2017) 2(3), CNC36.

Fattal, D. et al., A Multi-Directional Backlight for a Wide-Angle, Glasses-Free Three-Dimensional Display, Nature, Mar. 21, 2013, pp. 348-351, vol. 495.

Fielmann Annual Report 2019 (https://www.fielmann.eu/downloads/fielmann_annual_report_2019.pdf).

Gray, Margot, et al., Female adolescents demonstrate greater oculomotor and vestibular dysfunction than male adolescents following concussion, Physical Therapy in Sport 43 (2020) 68-74.

Halle M., "Autostereoscopic displays and computer graphics", Computer Graphics, ACM SIGGRAPH, 31(2), May 1997, pp. 58-62.

Howell, David R., et al., Near Point of Convergence and Gait Deficits in Adolescents After Sport-Related Concussion, Clin J Sport Med, 2017.

Howell, David R., et al., Receded Near Point of Convergence and Gait Are Associated After Concussion, Br J Sports Med, Jun. 2017; 51:e1, p. 9 (Abstract).

Huang, F.C. et al., "Eyeglasses-Free Display: Towards Correcting Visual Aberrations With Computational Light Field Displays,", ACM Transactions on Graphics (TOG)—Proceedings of ACM SIGGRAPH 2014, vol. 33, Issue 4, Article No. 59 , Jul. 2014.

Kawata, K., et al., Effect of Repetitive Sub-concussive Head Impacts on Ocular Near Point of Convergence, In t. J Sports Med 2016; 37; 405-410.

Lewin, Sarah "No Need for Reading Glasses With Vision-Correcting Display", published 2014.

Maimone, Andrew, et al. "Focus 3D: Compressive accommodation display." ACM Trans. Graph. 32.5 (2013): 153-1.

Masia B. et al., "A survey on computational displays: Pushing the boundaries of optics, computation, and perception", Computer & Graphics, vol. 37, 2013, pp. 1012-1038.

(56) References Cited

OTHER PUBLICATIONS

Murray, Nicholas G., et al., Smooth Pursuit and Saccades after Sport-Related Concussion, Journal of Neurotrauma 36: 1-7 (2019).
Pamplona V. F. et al., "Tailored Displays to Compensate for Visual Aberrations," ACM Transactions on Graphics (TOG), Jul. 2012 Article No. 81, https://doi.org/10.1145/2185520.2185577.
Pamplona V. F., Thesis (Ph.D.)—Universidade Federal do Rio Grande do Sul. Programa de Pós-Graduação em Computação, Porto Alegre, BR-RS, 2012. Advisor: Manuel Menezes de Oliveira Neto.
Ventura, Rachel E., et al., Diagnostic Tests for Concussion: Is Vision Part of the Puzzle?, Journal of Neuro-Ophthalmology 2015; 35; 73-81.
Wetzstein, G. et al., "Tensor Displays: Compressive Light Field Synthesis using Multilayer Displays with Directional Backlighting", https://web.media.mit.edu/~gordonw/TensorDisplays/TensorDisplays.pdf.
Zahid, Abdullah Bin, et al., Eye Tracking as a Biomarker for Concussion in Children, Clin J Sport Med 2018.

FIGURE 2A
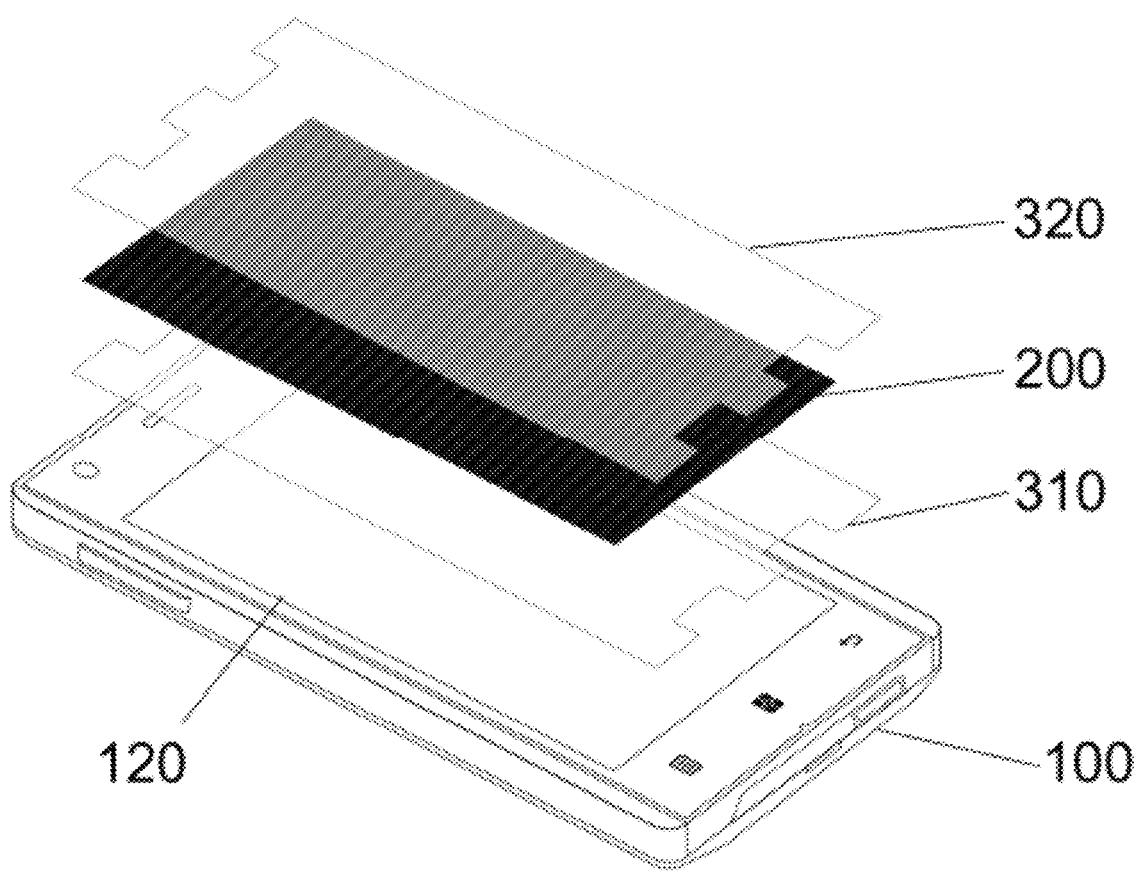
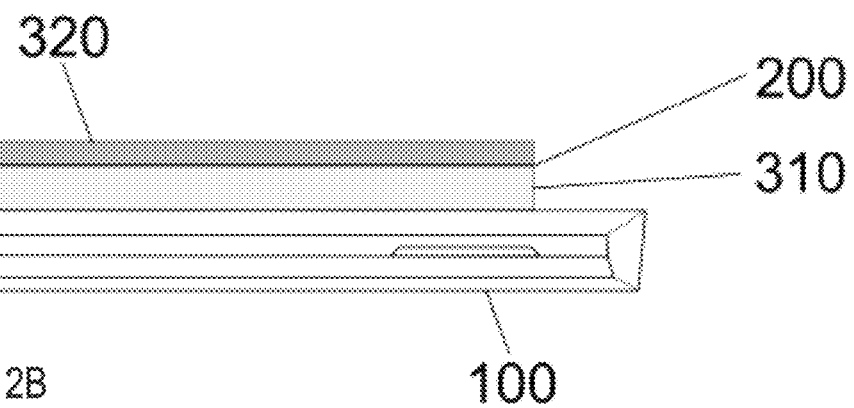
FIGURE 2B

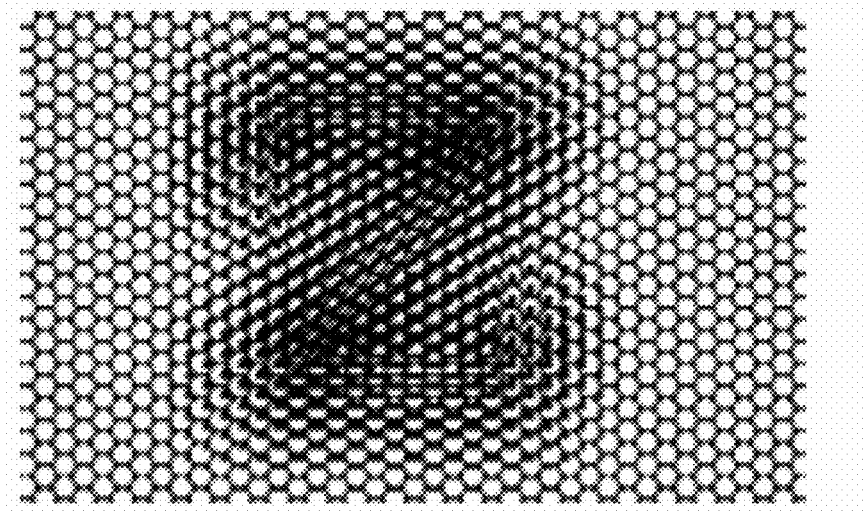
FIGURE 6
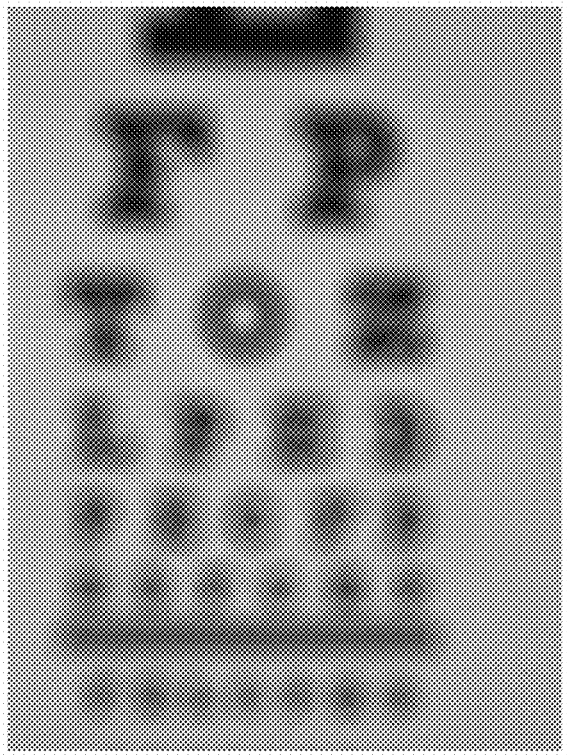 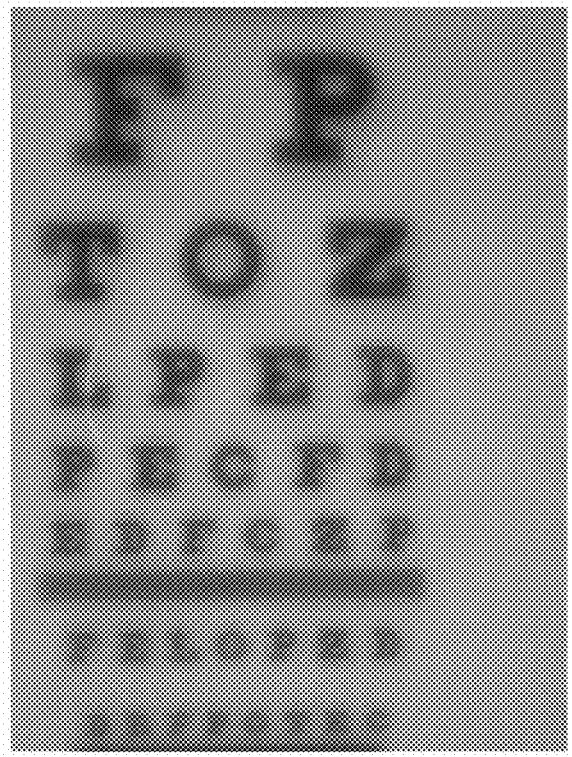
FIGURE 7A  FIGURE 7B

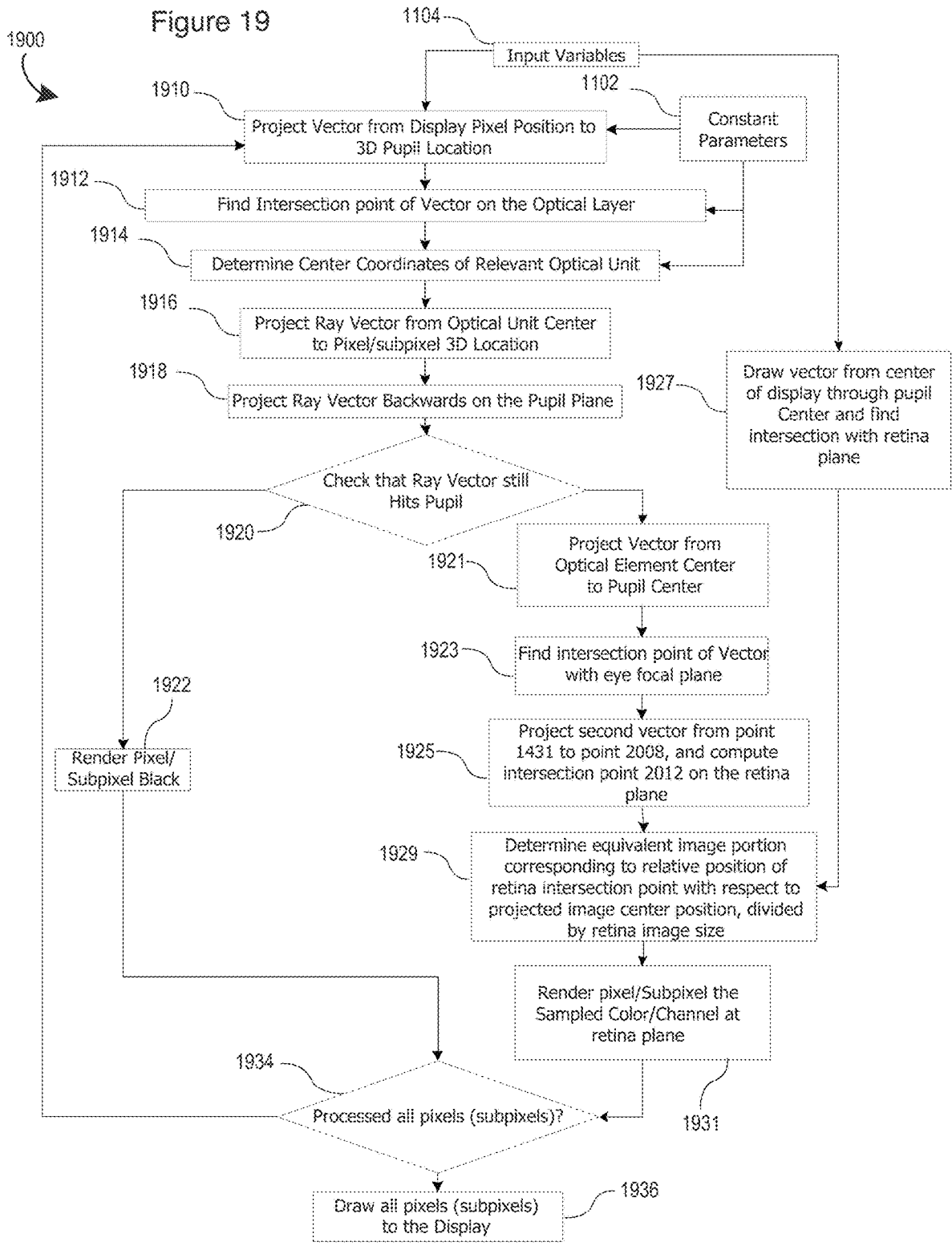

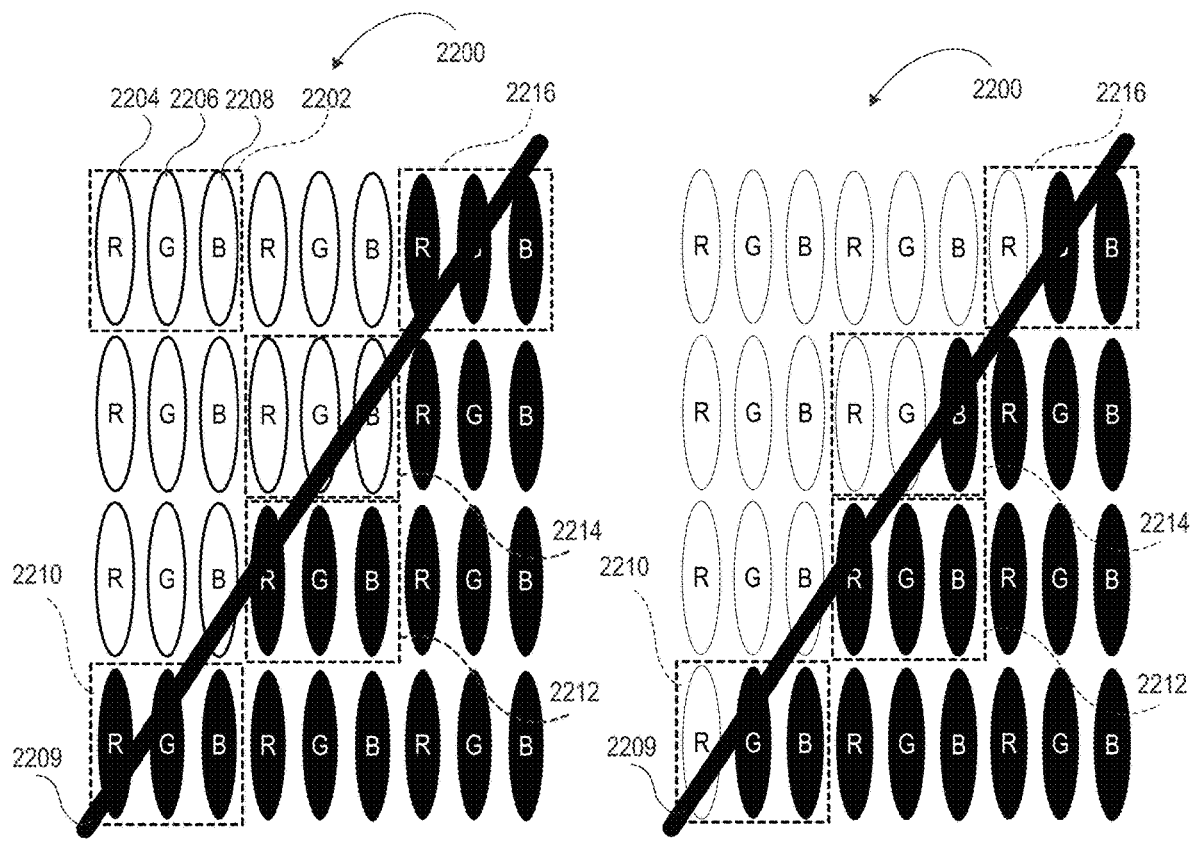
FIGURE 22A
FIGURE 22B
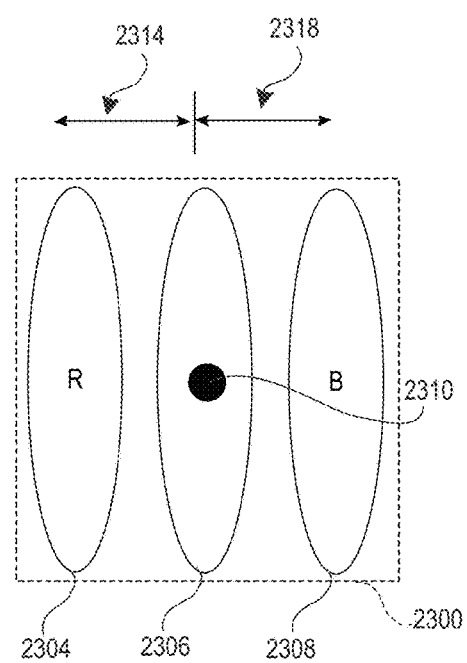
FIGURE 23

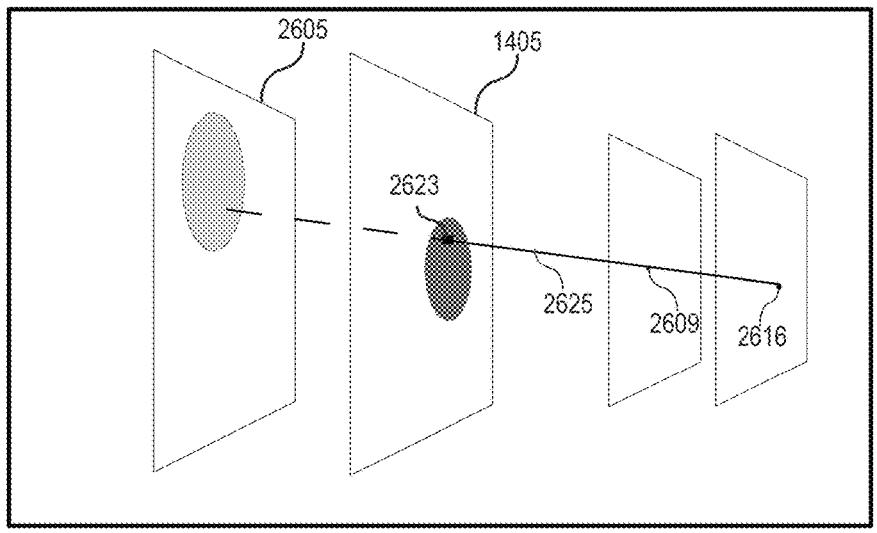
Figure 26A
Figure 26B
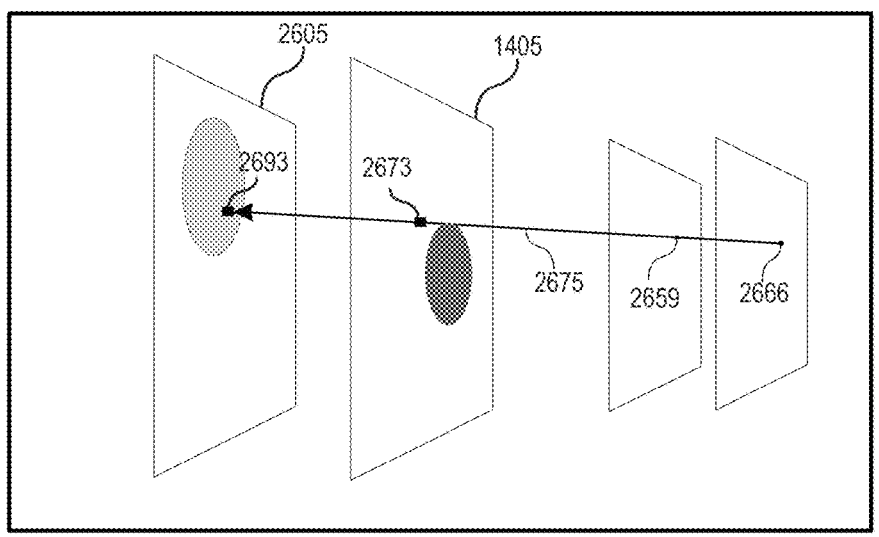
Figure 26C
Figure 26D ial Application No. PCT/IB2020/057887 filed Aug. 22, 2020, which claims priority to, and is a continuation of, U.S. patent application Ser. No. 16/810,143 filed Mar. 5, 2020 and issued as U.S. Pat. No. 10,761,604 on Sep. 1, 2020, which is a continuation-in-part of U.S. patent application Ser. No. 16/569,137 filed Sep. 12, 2019 and issued as U.S. Pat. No. 10,642,355 on May 5, 2020, which is a continuation of U.S. patent application Ser. No. 16/510,673 filed Jul. 12, 2019 and issued as U.S. Pat. No. 10,474,235 on Nov. 12, 2019, which is a continuation of U.S. patent application Ser. No. 16/259,845 filed Jan. 28, 2019 and issued as U.S. Pat. No. 10,394,322 on Aug. 27, 2020, which claims priority to Canadian Patent Application No. 3,021,636 filed Oct. 22, 2018, the entire disclosure of each of which is hereby incorporated herein by reference. International Application No. PCT/IB2020/057887 is a continuation-in-part of International Application No. PCT/IB2019/058955 filed Oct. 21, 2019, the entire disclosure of each of which is also hereby incorporated herein by reference. International Application No. PCT/IB2020/057887 also claims priority to U.S. Provisional Application No. 62/929,639 filed Nov. 1, 2019, the entire disclosure of which is also hereby incorporated by reference. U.S. patent application Ser. No. 16/810,143 is also a continuation-in-part of U.S. patent application Ser. No. 16/551,572 filed Aug. 26, 2019 and issued as U.S. Pat. No. 10,636,116 on Apr. 28, 2020, and a continuation-in-part of International Application No. PCT/IB2019/058955 filed Oct. 21, 2019, the entire disclosure of each of which is also hereby incorporated herein by reference.

U.S. patent application Ser. No. 17/302,392 is also a continuation-in-part of International Application No. PCT/US2020/058392 filed Oct. 30, 2020, which is a continuation-in-part of U.S. patent application Ser. No. 16/810,143 filed Mar. 5, 2020 and issued as U.S. Pat. No. 10,761,604 on Sep. 1, 2020, the entire disclosure of which is hereby incorporated by reference. PCT/US2020/058392 also claims priority to U.S. Provisional Application No. 62/929,639 filed Nov. 1, 2019 and International Application Serial No. PCT/IB2020/057887 filed Aug. 22, 2020, the entire disclosure of each of which is hereby incorporated herein by reference.

FIELD OF THE DISCLOSURE

The present disclosure relates to digital displays, and in particular, to a light field device, multi-depth pixel rendering method therefor, and multi-depth vision perception system and method using same.

BACKGROUND

Light field displays are known to adjust a user's perception of an input image by adjusting a light field emanated by the display so to control how a light field image is ultimately projected for viewing. For instance, in some examples, users who would otherwise require corrective eyewear such as glasses or contact lenses, or again bifocals, may consume images produced by such devices in clear or improved focus without the use of such eyewear. Other light field display applications, such as 3D displays, are also known.

This background information is provided to reveal information believed by the applicant to be of possible relevance. No admission is necessarily intended, nor should be construed, that any of the preceding information constitutes prior art.

SUMMARY

The following presents a simplified summary of the general inventive concept(s) described herein to provide a basic understanding of some aspects of the disclosure. This summary is not an extensive overview of the disclosure. It is not intended to restrict key or critical elements of the embodiments of the disclosure or to delineate their scope beyond that which is explicitly or implicitly described by the following description and claims.

A need exists for a light field display, adjusted pixel rendering method therefor, and adjusted vision perception system and method using same, that overcome some of the drawbacks of known techniques, or at least, provide a useful alternative thereto. Some aspects of disclosure provide embodiments of such systems, methods, and displays.

In accordance with one aspect, there is provided a computer-implemented method, automatically implemented by one or more digital processors, to adjust user perception of an image portion to be rendered via a set of pixels and a corresponding array of light field shaping elements (LFSE), the method comprising, for each given pixel of at least some of the set of pixels, digitally: projecting an adjusted image ray trace between said given pixel and a user pupil location to intersect an adjusted image location for a given perceived image depth given a direction of a light field emanated by said given pixel based on a given LFSE intersected thereby; upon said adjusted image ray trace intersecting a given image portion associated with said given perceived image depth, associating with said given pixel an adjusted image portion value designated for said adjusted image location based on said intersection; and rendering for each said given pixel said adjusted image portion value associated therewith, thereby perceptively rendering said adjusted image portion at said perceived image depth.

In one embodiment, the method is to adjust perception of distinct image portions, and further comprises, upon said adjusted image ray trace failing to intersect said given image portion associated with said given perceived image depth, repeating said projecting and associating for a subsequent perceived image depth and adjusted image portion associated therewith, thereby rendering distinctly perceptively adjusted image portions perceptively rendered at respectively corresponding perceived image depths.

In accordance with another aspect, there is provided a device operable to dynamically adjust user perception of an input image, the device comprising: an array of digital display pixels; a corresponding array of light field shaping elements (LFSEs) shaping a light field emanating from said pixels; and a hardware processor operable on pixel data for the input image to output adjusted image pixel data to be rendered via said LFSEs to dynamically adjust user perception of the input image as rendered therethrough by: digitally mapping the input image on an adjusted image plane corresponding to a designated vision correction parameter associated with a given visual acuity level; for each given pixel, digitally: projecting an adjusted image ray trace between said given pixel and a user pupil location to intersect said adjusted image plane at a given adjusted image location given a direction of a light field emanated by said given pixel based on a given LFESE intersected thereby; and associating an adjusted image pixel value designated for said given adjusted image location with said given pixel based on said mapping; rendering each said given pixel according to said adjusted pixel value, thereby rendering a perceptively adjusted version of the input image that at least partially accommodates said given visual acuity level; and adjusting said designated vision correction parameter to accommodate for a distinct visual acuity level until an optimal visual acuity level is identified.

In one embodiment, the input image is an optotype, and wherein said optimal visual acuity level is associated with a visual acuity of the user in prescribing corrective eyewear or surgery.

In one embodiment, the given visual acuity level corresponds with a minimum reading distance or a maximum reading distance.

In one embodiment, the device further comprises an adjustable refractive optical system, interposed between said array of pixels and said user pupil location so to set a selectable coarse refractive correction and thus further refract and thus redirect said light field emanated by each said given pixel, wherein said adjusted image ray trace is further projected between said given pixel and said user pupil location to intersect said adjusted image plane at said given adjusted image location based on said given LFSE and a current coarse refractive correction of said adjustable refractive optical system, wherein said optimal visual acuity level is identified as a function of said designated vision correction parameter and said current coarse refractive correction.

In one embodiment, the adjustable refractive optical system comprises at least one of a tunable lens or a lens selectable from an array of selectable lenses.

In one embodiment, the device is operable to dynamically adjust user perception of distinct image portions by: digitally processing each given image portion to be perceptively rendered according to distinct vision correction parameters to accommodate for distinct visual acuity levels for comparative purposes; and adjusting said distinct vision correction parameters until said optimal visual acuity level is identified.

In one embodiment, the distinct visual acuity levels correspond with distinct comfortable viewing distances and each given image portion is mapped to a respective adjusted image plane accordingly; said adjusted image ray trace is projected to identify a corresponding adjusted image location for a first viewing distance; upon said adjusted image ray trace intersecting said given image portion associated with said first viewing distance, associating with said given pixel an adjusted image portion value designated for said corresponding adjusted image location based on said intersection; otherwise repeating said projecting and associating for a subsequent viewing distance; and rendering for each said given pixel said adjusted image portion value associated therewith, thereby rendering distinctly perceptively adjusted image portions.

In one embodiment, the distinct image portions comprise distinct optotypes or distinct levels of correction for a same optotype.

In one embodiment, the distinct image portions comprise two side-by-side image portions.

In one embodiment, the distinct image portions comprise an array or grid of image portions.

In one embodiment, the device further comprises an adjustable refractive optical system interposed between said array of pixels and said user pupil location so to set a selectable common coarse refractive correction and thus further refract and thus redirect said light field emanated by each said given pixel, wherein the device is further operable to digitally process each said given image portion to be perceptively rendered according to said distinct vision correction parameters based on a current common coarse refractive correction.

In one embodiment, the device is a refractor or phoropter.

In one embodiment, the device further comprises a user eye alignment structure or a pupil tracking device to define said user pupil location.

In one embodiment, the device further comprises an optical reflector to fold an optical path between said user pupil location and said array of digital display pixels.

In one embodiment, the adjusted image plane comprises one of a virtual image plane virtually positioned relative to the digital display to correspond with said given visual acuity level or a user retinal plane based on a user eye focus parameter corresponding with said given visual acuity level.

In accordance with another aspect, there is provided a subjective eye test device comprising: an array of digital display pixels; a corresponding array of light field shaping elements (LFSEs) shaping a light field emanating from said pixels; and a hardware processor operable on pixel data for a defined optotype to output adjusted image pixel data to be rendered via said LFSEs to dynamically adjust user perception of said defined optotype as rendered therethrough by: digitally mapping said defined optotype on an adjusted image plane corresponding to a designated vision correction parameter associated with a given visual acuity level; for each given pixel, digitally: projecting an adjusted image ray trace between said given pixel and a user pupil location to intersect said adjusted image plane at a given adjusted image location given a direction of a light field emanated by said given pixel based on a given LFESE intersected thereby; and associating an adjusted image pixel value designated for said given adjusted image location with said given pixel based on said mapping; and rendering each said given pixel according to said adjusted pixel value, thereby rendering a perceptively adjusted version of said defined optotype that at least partially accommodates said given visual acuity level; and adjusting said designated vision correction parameter to accommodate for a distinct visual acuity level until an optimal visual acuity level is identified.

In one embodiment, the computer-implemented method, automatically implemented by one or more digital processors, to dynamically adjust user perception of an input image to be rendered by an array of digital display pixels via a corresponding array of light field shaping elements (LFSE), the method comprising: digitally mapping the input image on an adjusted image plane corresponding to a designated vision correction parameter associated with a given visual acuity level; for each given pixel, digitally: projecting an adjusted image ray trace between said given pixel and a user pupil location to intersect said adjusted image plane at a given adjusted image location given a direction of a light field emanated by said given pixel based on a given LFESE intersected thereby; and associating an adjusted image pixel value designated for said given adjusted image location with said given pixel based on said mapping; rendering each said given pixel according to said adjusted pixel value, thereby rendering a perceptively adjusted version of the input image that at least partially accommodates said given visual acuity level; and adjusting said designated vision correction parameter to accommodate for a distinct visual acuity level until an optimal visual acuity level is identified.

In one embodiment, the method dynamically adjusts user perception of distinct image portions by: digitally processing each given image portion to be perceptively rendered according to distinct vision correction parameters to accommodate for distinct visual acuity levels for comparative purposes; and adjusting said distinct vision correction parameters until said optimal visual acuity level is identified.

In one embodiment, the distinct visual acuity levels correspond with distinct comfortable viewing distances and each given image portion is mapped to a respective adjusted image plane accordingly; said adjusted image ray trace is projected to identify a corresponding adjusted image location for a first viewing distance; upon said adjusted image ray trace intersecting said given image portion associated with said first viewing distance, associating with said given pixel an adjusted image portion value designated for said corresponding adjusted image location based on said intersection; otherwise repeating said projecting and associating for a subsequent viewing distance; and rendering for each said given pixel said adjusted image portion value associated therewith, thereby rendering distinctly perceptively adjusted image portions.

In one embodiment, the distinct image portions comprise distinct optotypes or distinct levels of correction for a same optotype, and wherein said distinct image portions comprise side-by-side image portions or an array or grid of image portions.

In one embodiment, the adjusted image plane comprises one of a virtual image plane virtually positioned relative to the digital display to correspond with said given visual acuity level or a user retinal plane based on a user eye focus parameter corresponding with said given visual acuity level.

In one embodiment, the method further comprises, prior to said projecting: calculating a vector between said given pixel and said user pupil location; and approximating said direction of said light field emanated by said given pixel based on said given LFSE intersected by said vector.

In one embodiment, the method further comprises digitally accounting for an adjustable refractive optical system interposed between said array of pixels and said user pupil location so to set a selectable coarse refractive correction and thus further refract and thus redirect said light field emanated by each said given pixel, wherein said adjusted image ray trace is further projected between said given pixel and said user pupil location to intersect said adjusted image plane at said given adjusted image location based on said given LFSE and a current coarse refractive correction of said adjustable refractive optical system, wherein said optimal visual acuity level is identified as a function of said designated vision correction parameter and said current coarse refractive correction.

In accordance with another aspect, there is provided a non-transitory computer-readable medium comprising digital instructions to be implemented by one or more digital processors to dynamically adjust user perception of an input image to be rendered by an array of digital display pixels via a corresponding array of light field shaping elements (LFSE), by: digitally mapping the input image on an adjusted image plane corresponding to a designated vision correction parameter associated with a given visual acuity level; for each given pixel, digitally: projecting an adjusted image ray trace between said given pixel and a user pupil location to intersect said adjusted image plane at a given adjusted image location given a direction of a light field emanated by said given pixel based on a given LFSE intersected thereby; and associating an adjusted image pixel value designated for said given adjusted image location with said given pixel based on said mapping; rendering each said given pixel according to said adjusted pixel value, thereby rendering a perceptively adjusted version of the input image that at least partially accommodates said given visual acuity level; and adjusting said designated vision correction parameter to accommodate for a distinct visual acuity level until an optimal visual acuity level is identified.

In one embodiment, the non-transitory computer-readable medium further comprises digital instructions to be implemented to dynamically adjust user perception of distinct image portions by: digitally processing each given image portion to be perceptively rendered according to distinct vision correction parameters to accommodate for distinct visual acuity levels for comparative purposes; and adjusting said distinct vision correction parameters until said optimal visual acuity level is identified.

In one embodiment, the distinct visual acuity levels correspond with distinct comfortable viewing distances and each given image portion is mapped to a respective adjusted image plane accordingly; said adjusted image ray trace is projected to identify a corresponding adjusted image location for a first viewing distance; upon said adjusted image ray trace intersecting said given image portion associated with said first viewing distance, associating with said given pixel an adjusted image portion value designated for said corresponding adjusted image location based on said intersection; otherwise repeating said projecting and associating for a subsequent viewing distance; and rendering for each said given pixel said adjusted image portion value associated therewith, thereby rendering distinctly perceptively adjusted image portions.

In one embodiment, the distinct image portions comprise distinct optotypes or distinct levels of correction for a same optotype, and wherein said distinct image portions comprise side-by-side image portions or an array or grid of image portions.

In one embodiment, the adjusted image plane comprises one of a virtual image plane virtually positioned relative to the digital display to correspond with said given visual acuity level or a user retinal plane based on a user eye focus parameter corresponding with said given visual acuity level.

In one embodiment, the non-transitory computer-readable further comprising instructions for, prior to said projecting: calculating a vector between said given pixel and said user pupil location; and approximating said direction of said light field emanated by said given pixel based on said given LFSE intersected by said vector.

In one embodiment, the non-transitory computer-readable medium further comprising digital instructions to be implemented to account for an adjustable refractive optical system interposed between said array of pixels and said user pupil location so to set a selectable coarse refractive correction and thus further refract and thus redirect said light field emanated by each said given pixel, wherein said adjusted image ray trace is further projected between said given pixel and said user pupil location to intersect said adjusted image plane at said given adjusted image location based on said given LFSE and a current coarse refractive correction of said adjustable refractive optical system, wherein said optimal visual acuity level is identified as a function of said designated vision correction parameter and said current coarse refractive correction.

In accordance with another aspect, there is provided a computer-implemented method, automatically implemented by one or more digital processors, to automatically adjust user perception of distinct image portions to be rendered on a digital display via a set of pixels thereof, wherein the digital display has an array of light field shaping elements (LFSE), the method comprising: digitally processing each given image portion to be perceptively rendered at a corresponding perceived image depth by, for each given pixel in at least some of the pixels, digitally: calculating a vector between said given pixel and a user pupil location; approximating a direction of a light field emanated by said given pixel based on a given LFSE intersected by said vector; projecting an adjusted image ray trace between said given pixel and said given LFSE to identify a corresponding adjusted image location for a first perceived image depth given said direction; upon said adjusted image ray trace intersecting said given image portion associated with said first perceived image depth, associating with said given pixel an adjusted image portion value designated for said corresponding adjusted image location based on said intersection; otherwise repeating said projecting and associating for a subsequent perceived image depth; and rendering for each said given pixel said adjusted image portion value associated therewith, thereby rendering distinctly perceptively adjusted image portions.

In one embodiment, each of said image portions is digitally mapped to a corresponding virtual image plane virtually positioned relative to the digital display at said corresponding perceived image depth, and wherein said intersection is defined on said corresponding virtual image plane.

In one embodiment, each of said image portions is mapped to a user retinal plane in accordance with said corresponding perceived image depth based on a user eye focus parameter, and wherein said intersection is defined on said retinal plane by redirecting said adjusted image ray trace at said pupil location in accordance with said user eye focus parameter.

In one embodiment, said projecting and associating are implemented in parallel for each said given pixel of at least a subset of said pixels.

In accordance with another aspect, there is provided a non-transitory computer-readable medium comprising digital instructions to be implemented by one or more digital processors to automatically adjust user perception of distinct image portions to be rendered on a digital display via a set of pixels thereof, wherein the digital display has an array of light field shaping elements (LFSE), by: digitally processing each given image portion to be perceptively rendered at a corresponding perceived image depth by, for each given pixel in at least some of the pixels, digitally: calculating a vector between said given pixel and a user pupil location; approximating a direction of a light field emanated by said given pixel based on a given LFSE intersected by said vector; projecting an adjusted image ray trace between said given pixel and said given LFSE to identify a corresponding adjusted image location for a first perceived image depth given said direction; upon said adjusted image ray trace intersecting said given image portion associated with said first perceived image depth, associating with said given pixel an adjusted image portion value designated for said corresponding adjusted image location based on said intersection; otherwise repeating said projecting and associating for a subsequent perceived image depth; and rendering for each said given pixel said adjusted image portion value associated therewith, thereby rendering distinctly perceptively adjusted image portions.

In accordance with another aspect, there is provided a digital display device operable to automatically adjust user perception of distinct image portions to be rendered thereon, the device comprising: a digital display medium comprising an array of pixels and operable to render a pixelated image accordingly; an array of light field shaping elements (LFSEs) to shape a light field emanating from said pixels and thereby at least partially govern a projection thereof from said display medium toward the user; and a hardware processor operable on pixel data for the input image portions to output adjusted image pixel data to be rendered via said LFSEs to adjust user perception of said input image portions as rendered therethrough by: digitally processing each given image portion to be perceptively rendered at a corresponding perceived image depth by, for each given pixel in at least some of the pixels, digitally: calculating a vector between said given pixel and a user pupil location; approximating a direction of a light field emanated by said given pixel based on a given LFSE intersected by said vector; projecting an adjusted image ray trace between said given pixel and said given LFSE to identify a corresponding adjusted image location for a first perceived image depth given said direction; upon said adjusted image ray trace intersecting said given image portion associated with said first perceived image depth, associating with said given pixel an adjusted image portion value designated for said corresponding adjusted image location based on said intersection; otherwise repeating said projecting and associating for a subsequent perceived image depth; and rendering for each said given pixel said adjusted image portion value associated therewith, thereby rendering distinctly perceptively adjusted image portions.

In one embodiment, the digital display device further comprises a pupil tracker or pupil tracking interface operable to dynamically track and automatically accommodate for changes in said input user pupil location.

In one embodiment, the array of LFSEs comprises a lenslet array.

In one embodiment, each of said image portions correspond to an optotype that are rendered side-by-side at distinct perceived image depths.

In accordance with another aspect, there is provided a device for subjective vision testing of a user having a reduced visual acuity, the device comprising: the digital display as described above, wherein each of said image portions corresponds to an optotype; and wherein the display is operable to simultaneously render said optotype in each of said portions side-by-side at distinct perceived image depths.

In one embodiment, the distinct perceived image depths are dynamically variable via said display to subjectively assess a user's reduced visual acuity.

In one embodiment, the device further comprises a variable optical system disposed in a line-of-sight of the display so to further adjust said perceived depth for said rendered image portions.

In accordance with another aspect, there is provided a computer-implemented method, automatically implemented by one or more digital processors, to adjust user perception of distinct image portions to be rendered via a set of pixels and a corresponding array of light field shaping elements (LFSE), the method comprising, for each given pixel of at least some of the set of pixels, digitally: digitally projecting an adjusted image ray trace between said given pixel and a user pupil location to intersect an adjusted image location for a given perceived image depth given a direction of a light field emanated by said given pixel based on a given LFSE intersected thereby; upon said adjusted image ray trace intersecting a given image portion associated with said given perceived image depth, associating with said given pixel an adjusted image portion value designated for said adjusted image location based on said intersection; otherwise repeating said projecting and associating for a subsequent perceived image depth and adjusted image portion associated therewith; and rendering for each said given pixel said adjusted image portion value associated therewith, thereby rendering distinctly perceptively adjusted image portions perceptively rendered at respectively corresponding perceived image depths.

In accordance with another aspect, there is provided a non-transitory computer-readable medium comprising digital instructions to be implemented by one or more digital processors to automatically adjust user perception of distinct image portions to be rendered on a digital display via a set of pixels thereof and an array of light field shaping elements (LFSE) disposed relative thereto, by, for each given pixel of at least some of the set of pixels, digitally: digitally projecting an adjusted image ray trace between said given pixel and a user pupil location to intersect an adjusted image location for a given perceived image depth given a direction of a light field emanated by said given pixel based on a given LFESE intersected thereby; upon said adjusted image ray trace intersecting a given image portion associated with said given perceived image depth, associating with said given pixel an adjusted image portion value designated for said adjusted image location based on said intersection to be rendered accordingly; otherwise repeating said projecting and associating for a subsequent perceived image depth and adjusted image portion associated therewith; thereby rendering distinctly perceptively adjusted image portions perceptively rendered at respectively corresponding perceived image depths.

In one embodiment, the computer-readable medium further comprises instructions for, or the method further comprises, prior to said projecting: calculating a vector between said given pixel and said user pupil location; and approximating said direction of said light field emanated by said given pixel based on said given LFSE intersected by said vector.

In one embodiment, each of said image portions is digitally mapped to a corresponding virtual image plane virtually positioned relative to the pixels at said respectively corresponding perceived image depths, and wherein said intersection is defined on said corresponding virtual image plane.

In one embodiment, each of said image portions is mapped to a user retinal plane in accordance with said given perceived image depth based on a user eye focus parameter, and wherein said intersection is defined on said retinal plane by redirecting said adjusted image ray trace at said pupil location in accordance with said user eye focus parameter.

In one embodiment, the projecting and associating are implemented in parallel for each said given pixel of at least a subset of said pixels.

In one embodiment, the distinct image portions are to be perceptively rendered side-by-side at said respectively corresponding perceived image depths.

In one embodiment, the distinct image portions are to be perceptively rendered side-by-side at said respectively corresponding perceived image depths in a 2-dimentional grid or in respective image quadrants.

In one embodiment, each of said image portions correspond to an optotype simultaneously rendered in each of said portions side-by-side at distinct perceived image depths to subjectively assess a user's reduced visual acuity.

In one embodiment, the overlap between said image portions are automatically addressed by rendering a nearest perceptive depth.

In accordance with another aspect, there is provided a digital display device comprising: an array of pixels; an array of light field shaping elements (LFSEs) to shape a light field emanating from said pixels and thereby at least partially govern a projection thereof from said pixels toward a given user pupil location; and a hardware processor operable on pixel data for input image portions to output adjusted image pixel data to be rendered via said LFSEs to adjust user perception from said given user pupil location of said input image portions as rendered therethrough and thereby render distinctly perceptively adjusted image portions at respectively corresponding perceived image depths.

In one embodiment, the hardware processor outputs said adjusted pixel data as a function of adjusted image ray traces digitally computed for each given pixel of at least some of the array of pixels that intersect said user pupil location.

In one embodiment, the hardware processor is operable to, for each given pixel of at least some of the array of pixels: digitally project an adjusted image ray trace between said given pixel and said given user pupil location to intersect an adjusted image location for a given perceived image depth given a direction of a light field emanated by said given pixel based on a given LFESE intersected thereby; upon said adjusted image ray trace intersecting a given image portion associated with said given perceived image depth, associate with said given pixel an adjusted image portion value designated for said adjusted image location based on said intersection; otherwise repeat said projecting and associating for a subsequent perceived image depth and adjusted image portion associated therewith; and render for each said given pixel said adjusted image portion value associated therewith, thereby rendering distinctly perceptively adjusted image portions perceptively rendered at respectively corresponding perceived image depths.

In one embodiment, the hardware processor is further operable to, prior to said projecting: calculate a vector between said given pixel and said user pupil location; and approximate said direction of said light field emanated by said given pixel based on said given LFSE intersected by said vector.

In one embodiment, each of said image portions is digitally mapped to a corresponding virtual image plane virtually positioned relative to the digital display at said respectively corresponding perceived image depths, and wherein said intersection is defined on said corresponding virtual image plane.

In one embodiment, each of said image portions is mapped to a user retinal plane in accordance with said given perceived image depth based on a user eye focus parameter, and wherein said intersection is defined on said retinal plane by redirecting said adjusted image ray trace at said pupil location in accordance with said user eye focus parameter.

In one embodiment, the projecting and associating are implemented in parallel for each said given pixel of at least a subset of said pixels.

In one embodiment, the distinct image portions are to be perceptively rendered side-by-side at said respectively corresponding perceived image depths.

In one embodiment, the distinct image portions are to be perceptively rendered side-by-side at said respectively corresponding perceived image depths in a 2-dimensional grid or in respective image quadrants.

In one embodiment, each of said image portions correspond to an optotype simultaneously rendered in each of said portions side-by-side at distinct perceived image depths to subjectively assess a user's reduced visual acuity.

In one embodiment, overlap between said image portions are automatically addressed by rendering a nearest perceptive depth.

In one embodiment, the device further comprises a pupil tracker or pupil tracking interface operable to dynamically track and automatically accommodate for changes in said given user pupil location.

In one embodiment, the array of LFSEs comprises a lenslet array.

In one embodiment, each of said distinct perceived image depths are dynamically variable so to subjectively assess the user's reduced visual acuity.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIGS. 2A and 2B are exploded and side views, respectively, of an assembly of a light field display for an electronic device, in accordance with one embodiment;

FIG. 6 is an exemplary diagram of a light field pattern that, when properly projected by a light field display, produces a corrected image exhibiting reduced blurring for a viewer having reduced visual acuity, in accordance with one embodiment;

FIGS. 7A and 7B are photographs of a Snellen chart, as illustratively viewed by a viewer with reduced acuity without image correction (blurry image in FIG. 7A) and with image correction via a light field display (corrected image in FIG. 7B), in accordance with one embodiment;

FIG. 19 is process flow diagram of an illustrative ray-tracing rendering process, in accordance with another embodiment;

FIGS. 22A and 22B are schematic diagrams of an LCD pixel array defined by respective red (R), green (G) and blue (B) subpixels, and rendering an angular image edge using pixel and subpixel rendering, respectively, in accordance with one embodiment;

FIG. 23 is a schematic diagram of one of the pixels of FIG. 22A, showing measures for independently accounting for subpixels thereof apply subpixel rendering to the display of a corrected image through a light field display, in accordance with one embodiment;

FIGS. 26A to 26D are schematic diagrams illustrating certain process steps of FIG. 25;

Figure 1:
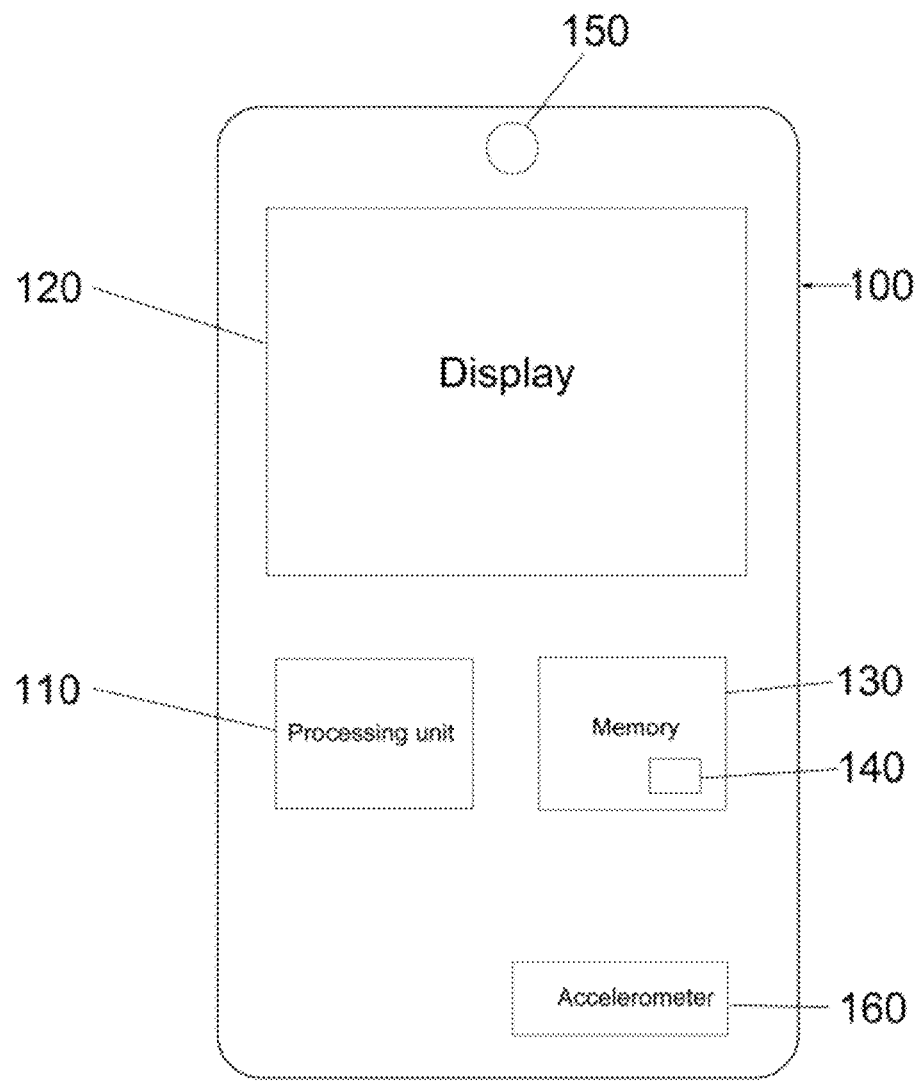
FIG. 1 is a diagrammatical view of an electronic device having a digital display, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

The systems and methods described herein provide, in accordance with different embodiments, different examples of a light field display, adjusted pixel rendering method therefor, and adjusted vision perception system and method using same. For example, some of the herein-described embodiments provide improvements or alternatives to current light field display technologies, for instance, providing for multiple concurrent adjusted image perception planes, depths, and/or focus, which, in some examples, may result in perceptible 2.5D/3D or adjustable location-based image perspective effects, distinctly optimized vision correction tools or vision corrected 2.5D/3D rendering tools, or again provide tools, equipment, features or solutions for the implementation of subjective vision tests. For example, a subjective vision (e.g. blur) testing tool can rely on the herein-described solutions to simultaneously depict distinct optotypes corresponding to respective optical resolving or corrective powers in providing a subjective basis for optical testing comparisons. These and other such applications will be described in further detail below.

As noted above, the devices, displays and methods described herein may allow a user's perception of one or more input images (or input image portions), where each image or image portion is virtually located at a distinct image plane/depth location, to be adjusted or altered using the light field display. These may be used, as described below, to provide vision correction for a user viewing digital displays, but the same light field displays and rendering technology, as detailed below and according to different embodiments, may equally be used or be implemented in a refractor or phoropter-like device to test, screen, diagnose and/or deduce a patient's reduced visual acuity. In accordance with some embodiments, different vision testing devices and systems as described herein may be contemplated so to replace or complement traditional vision testing devices such as refractors and/or phoropters, in which traditional devices different optotypes are shown to a user in sequence via changing and/or compounding optical elements (lenses, prisms, etc.) so to identify an optical combination that best improves the user's perception of these displayed optotypes. As will be described in greater detail below, embodiments as described herein introduce light field display technologies and image rendering techniques, alone or in combination with complementary optical elements such as refractive lens, prisms, etc., to provide, amongst other benefits, for greater vision testing versatility, compactness, portability, range, precision, and/or other benefits as will be readily appreciated by the skilled artisan. Accordingly, while the terms light field refractor or phoropter will be used interchangeably herein to reference the implementation of different embodiments of a more generally defined light field vision testing device and system, the person of ordinary skill in the art will appreciate the versatility of the herein described implementation of light field rendering techniques, and ray tracing approaches detailed herein with respect to some embodiments, in the provision of effective light field vision testing devices and systems in general.

As noted above, some of the herein described embodiments provide for digital display devices, or devices encompassing such displays, for use by users having reduced visual acuity, whereby images ultimately rendered by such devices can be dynamically processed to accommodate the user's reduced visual acuity so that they may consume rendered images without the use of corrective eyewear, as would otherwise be required. Accordingly, such embodiments can be dynamically controlled to progressively adjust a user's perception of rendered images or image portions (e.g. optotype within the context of a blur test for example) until an optimized correction is applied that optimizes the user's perception. Perception adjustment parameters used to achieve this optimized perception can then be translated into a proposed vision correction prescription to be applied to corrective eyewear. Conversely, a user's vision correction eyewear prescription can be used as input to dictate selection of applied vision correction parameters and related image perception adjustment, to validate or possibly further fine tune the user's prescription, for example, and progressively adjusting such correction parameters to test for the possibility of a further improvement. As noted above, embodiments are not to be limited as such as the notions or solutions described herein may also be applied to other technologies in which a user's perception of an input image to be displayed can be altered or adjusted via the light field display. However, for the sake of illustration, a number of the herein described embodiments will be described as allowing for implementation of digitally adaptive vision tests such that individuals with such reduced visual acuity can be exposed to distinct perceptively adjusted versions of an input image(s) (e.g. optotypes) to subjectively ascertain a potentially required or preferred vision correction.

Generally, digital displays as considered herein will comprise a set of image rendering pixels and a corresponding set of light field shaping elements that at least partially govern a light field emanated thereby to produce a perceptively adjusted version of the input image, notably distinct perceptively adjusted portions of an input image or input scene, which may include distinct portions of a same image, a same 2.5D/3D scene, or distinct images (portions) associated with different image depths, effects and/or locations and assembled into a combined visual input. For simplicity, the following will generally consider distinctly addressed portions or segments as distinct portions of an input image, whether that input image comprises a singular image having distinctly characterized portions, a digital assembly of distinctly characterized images, overlays, backgrounds, foregrounds or the like, or any other such digital image combinations.

In some examples, light field shaping elements may take the form of a light field shaping layer or like array of optical elements to be disposed relative to the display pixels in at least partially governing the emanated light field. As described in further detail below, such light field shaping layer elements may take the form of a microlens and/or pinhole array, or other like arrays of optical elements, or again take the form of an underlying light shaping layer, such as an underlying array of optical gratings or like optical elements operable to produce a directional pixelated output.

Within the context of a light field shaping layer, as described in further detail below in accordance with some embodiments, the light field shaping layer can be disposed at a pre-set distance from the pixelated display so to controllably shape or influence a light field emanating therefrom. For instance, each light field shaping layer can be defined by an array of optical elements centered over a corresponding subset of the display's pixel array to optically influence a light field emanating therefrom and thereby govern a projection thereof from the display medium toward the user, for instance, providing some control over how each pixel or pixel group will be viewed by the viewer's eye(s). As will be further detailed below, arrayed optical elements may include, but are not limited to, lenslets, microlenses or other such diffractive optical elements that together form, for example, a lenslet array; pinholes or like apertures or windows that together form, for example, a parallax or like barrier; concentrically patterned barriers, e.g. cut outs and/or windows, such as a to define a Fresnel zone plate or optical sieve, for example, and that together form a diffractive optical barrier (as described, for example, in Applicant's co-pending U.S. application Ser. No. 15/910,908, the entire contents of which are hereby incorporated herein by reference); and/or a combination thereof, such as for example, a lenslet array whose respective lenses or lenslets are partially shadowed or barriered around a periphery thereof so to combine the refractive properties of the lenslet with some of the advantages provided by a pinhole barrier.

In operation, the display device will also generally invoke a hardware processor operable on image pixel (or subpixel) data for an image to be displayed to output corrected or adjusted image pixel data to be rendered as a function of a stored characteristic of the light field shaping elements and/or layer, e.g. layer distance from display screen, distance between optical elements (pitch), absolute relative location of each pixel or subpixel to a corresponding optical element, properties of the optical elements (size, diffractive and/or refractive properties, etc.), or other such properties, and a selected vision correction or adjustment parameter related to the user's reduced visual acuity or intended viewing experience. While light field display characteristics will generally remain static for a given implementation (i.e. a given shaping element and/or layer will be used and set for each device irrespective of the user), image processing can, in some embodiments, be dynamically adjusted as a function of the user's visual acuity or intended application so to actively adjust a distance of a virtual image plane, or perceived image on the user's retinal plane given a quantified user eye focus or like optical aberration(s), induced upon rendering the corrected/adjusted image pixel data via the static optical layer and/or elements, for example, or otherwise actively adjust image processing parameters as may be considered, for example, when implementing a viewer-adaptive pre-filtering algorithm or like approach (e.g. compressive light field optimization), so to at least in part govern an image perceived by the user's cyc(s) given pixel or subpixel-specific light visible thereby through the layer.

Accordingly, a given device may be adapted to compensate for different visual acuity levels and thus accommodate different users and/or uses. For instance, a particular device may be configured to implement and/or render an interactive graphical user interface (GUI) that incorporates a dynamic vision correction scaling function that dynamically adjusts one or more designated vision correction parameter(s) in real-time in response to a designated user interaction therewith via the GUI. For example, a dynamic vision correction scaling function may comprise a graphically rendered scaling function controlled by a (continuous or discrete) user slide motion or like operation, whereby the GUI can be configured to capture and translate a user's given slide motion operation to a corresponding adjustment to the designated vision correction parameter(s) scalable with a degree of the user's given slide motion operation. These and other examples are described in Applicant's co-pending U.S. patent application Ser. No. 15/246,255, the entire contents of which are hereby incorporated herein by reference.

With reference to FIG. 1, and in accordance with one embodiment, a digital display device, generally referred to using the numeral 100, will now be described. In this example, the device 100 is generally depicted as a smartphone or the like, though other devices encompassing a graphical display may equally be considered, such as tablets, e-readers, watches, televisions, GPS devices, laptops, desktop computer monitors, televisions, smart televisions, handheld video game consoles and controllers, vehicular dashboard and/or entertainment displays, and the like.

In the illustrated embodiment, the device 100 comprises a processing unit 110, a digital display 120, and internal memory 130. Display 120 can be an LCD screen, a monitor, a plasma display panel, an LED or OLED screen, or any other type of digital display defined by a set of pixels for rendering a pixelated image or other like media or information. Internal memory 130 can be any form of electronic storage, including a disk drive, optical drive, read-only memory, random-access memory, or flash memory, to name a few examples. For illustrative purposes, memory 130 has stored in it vision correction application 140, though various methods and techniques may be implemented to provide computer-readable code and instructions for execution by the processing unit in order to process pixel data for an image to be rendered in producing corrected pixel data amenable to producing a corrected image accommodating the user's reduced visual acuity (e.g. stored and executable image correction application, tool, utility or engine, etc.). Other components of the electronic device 100 may optionally include, but are not limited to, one or more rear and/or front-facing camera(s) 150, an accelerometer 160 and/or other device positioning/orientation devices capable of determining the tilt and/or orientation of electronic device 100, and the like.

For example, the electronic device 100, or related environment (e.g. within the context of a desktop workstation, vehicular console/dashboard, gaming or e-learning station, multimedia display room, etc.) may include further hardware, firmware and/or software components and/or modules to deliver complementary and/or cooperative features, functions and/or services. For example, in some embodiment, and as will be described in greater detail below, a pupil/eye tracking system may be integrally or cooperatively implemented to improve or enhance corrective image rending by tracking a location of the user's eye(s)/pupil(s) (e.g. both or one, e.g. dominant, cyc(s)) and adjusting light field corrections accordingly. For instance, the device 100 may include, integrated therein or interfacing therewith, one or more eye/pupil tracking light sources, such as one or more infrared (IR) or near-IR (NIR) light source(s) to accommodate operation in limited ambient light conditions, leverage retinal retro-reflections, invoke corneal reflection, and/or other such considerations. For instance, different IR/NIR pupil tracking techniques may employ one or more (e.g. arrayed) directed or broad illumination light sources to stimulate retinal retro-reflection and/or corneal reflection in identifying a tracking a pupil location. Other techniques may employ ambient or IR/NIR light-based machine vision and facial recognition techniques to otherwise locate and track the user's eye(s)/pupil(s). To do so, one or more corresponding (e.g. visible, IR/NIR) cameras may be deployed to capture eye/pupil tracking signals that can be processed, using various image/sensor data processing techniques, to map a 3D location of the user's cyc(s)/pupil(s). In the context of a mobile device, such as a mobile phone, such eye/pupil tracking hardware/software may be integral to the device, for instance, operating in concert with integrated components such as one or more front facing camera(s), onboard IR/NIR light source(s) and the like. In other user environments, such as in a vehicular environment, eye/pupil tracking hardware may be further distributed within the environment, such as dash, console, ceiling, windshield, mirror or similarly-mounted camera(s), light sources, etc.

With reference to FIGS. 2A and 2B, the electronic device 100, such as that illustrated in FIG. 1, is further shown to include a light field shaping layer (LFSL) 200 overlaid atop a display 120 thereof and spaced therefrom via a transparent spacer 310 or other such means as may be readily apparent to the skilled artisan. An optional transparent screen protector 320 is also included atop the layer 200.

For the sake of illustration, the following embodiments will be described within the context of a light field shaping layer defined, at least in part, by a lenslet array comprising an array of microlenses (also interchangeably referred to herein as lenslets) that are each disposed at a distance from a corresponding subset of image rendering pixels in an underlying digital display. It will be appreciated that while a light field shaping layer may be manufactured and disposed as a digital screen overlay, other integrated concepts may also be considered, for example, where light field shaping elements are integrally formed or manufactured within a digital screen's integral components such as a textured or masked glass plate, beam-shaping light sources (e.g. directional light sources and/or backlit integrated optical grating array) or like component.

Accordingly, each lenslet will predictively shape light emanating from these pixel subsets to at least partially govern light rays being projected toward the user by the display device. As noted above, other light field shaping layers may also be considered herein without departing from the general scope and nature of the present disclosure, whereby light field shaping will be understood by the person of ordinary skill in the art to reference measures by which light, that would otherwise emanate indiscriminately (i.e. isotropically) from each pixel group, is deliberately controlled to define predictable light rays that can be traced between the user and the device's pixels through the shaping layer.

For greater clarity, a light field is generally defined as a vector function that describes the amount of light flowing in every direction through every point in space. In other words, anything that produces or reflects light has an associated light field. The embodiments described herein produce light fields from an object that are not "natural" vector functions one would expect to observe from that object. This gives it the ability to emulate the "natural" light fields of objects that do not physically exist, such as a virtual display located far behind the light field display, which will be referred to now as the 'virtual image'. As noted in the examples below, in some embodiments, light field rendering may be adjusted to effectively generate a virtual image on a virtual image plane that is set at a designated distance from an input user pupil location, for example, so to effectively push back, or move forward, a perceived image relative to the display device in accommodating a user's reduced visual acuity (e.g. minimum or maximum viewing distance). In yet other embodiments, light field rendering may rather or alternatively seek to map the input image on a retinal plane of the user, taking into account visual aberrations, so to adaptively adjust rendering of the input image on the display device to produce the mapped effect. Namely, where the unadjusted input image would otherwise typically come into focus in front of or behind the retinal plane (and/or be subject to other optical aberrations), this approach allows to map the intended image on the retinal plane and work therefrom to address designated optical aberrations accordingly. Using this approach, the device may further computationally interpret and compute virtual image distances tending toward infinity, for example, for extreme cases of presbyopia. This approach may also more readily allow, as will be appreciated by the below description, for adaptability to other visual aberrations that may not be as readily modeled using a virtual image and image plane implementation. In both of these examples, and like embodiments, the input image is digitally mapped to an adjusted image plane (e.g. virtual image plane or retinal plane) designated to provide the user with a designated image perception adjustment that at least partially addresses designated visual aberrations. Naturally, while visual aberrations may be addressed using these approaches, other visual effects may also be implemented using similar techniques.

Figure 3A:
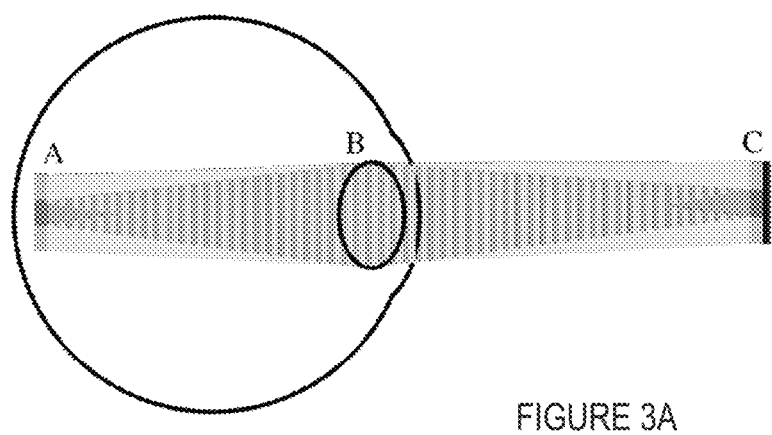
FIGS. 3A, 3B and 3C schematically illustrate normal vision, blurred vision, and corrected vision in accordance with one embodiment, respectively.
Figure 3B:
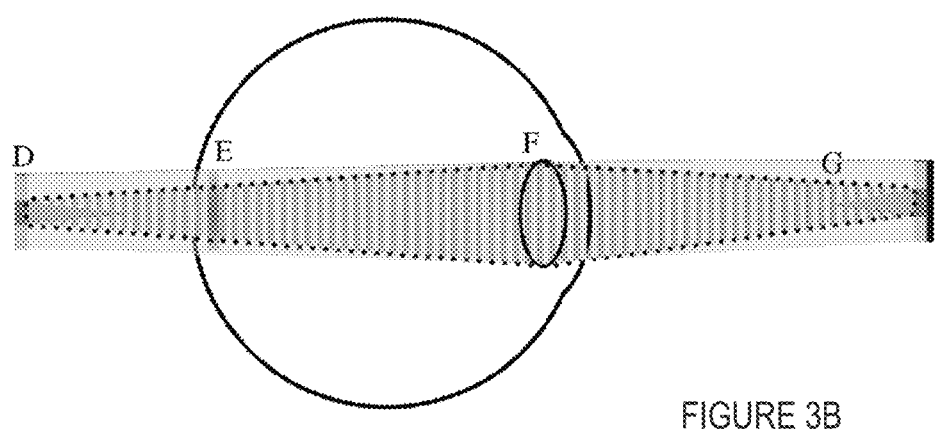

In one example, to apply this technology to vision correction, consider first the normal ability of the lens in an eye, as schematically illustrated in FIG. 3A, where, for normal vision, the image is to the right of the eye (C) and is projected through the lens (B) to the retina at the back of the eye (A). As comparatively shown in FIG. 3B, the poor lens shape (F) in presbyopia causes the image to be focused past the retina (D) forming a blurry image on the retina (E). The dotted lines outline the path of a beam of light (G). Naturally, other visual aberrations can and will have different impacts on image formation on the retina. To address these aberrations, a light field display (K), in accordance with some embodiments, projects the correct sharp image (H) to the back of the retina for an eye with a lens which otherwise could not adjust sufficiently to produce a sharp image. The other two light field pixels (I) and (J) are drawn lightly, but would otherwise fill out the rest of the image.

Figure 3C:
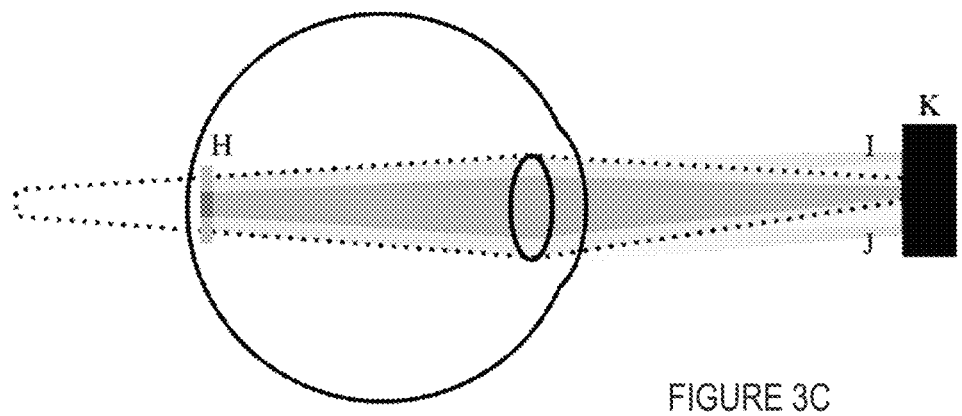

As will be appreciated by the skilled artisan, a light field as seen in FIG. 3C cannot be produced with a 'normal' two-dimensional display because the pixels' light field emits light isotropically. Instead it is necessary to exercise tight control on the angle and origin of the light emitted, for example, using a microlens array or other light field shaping layer such as a parallax barrier, or combination thereof.

Figure 4:
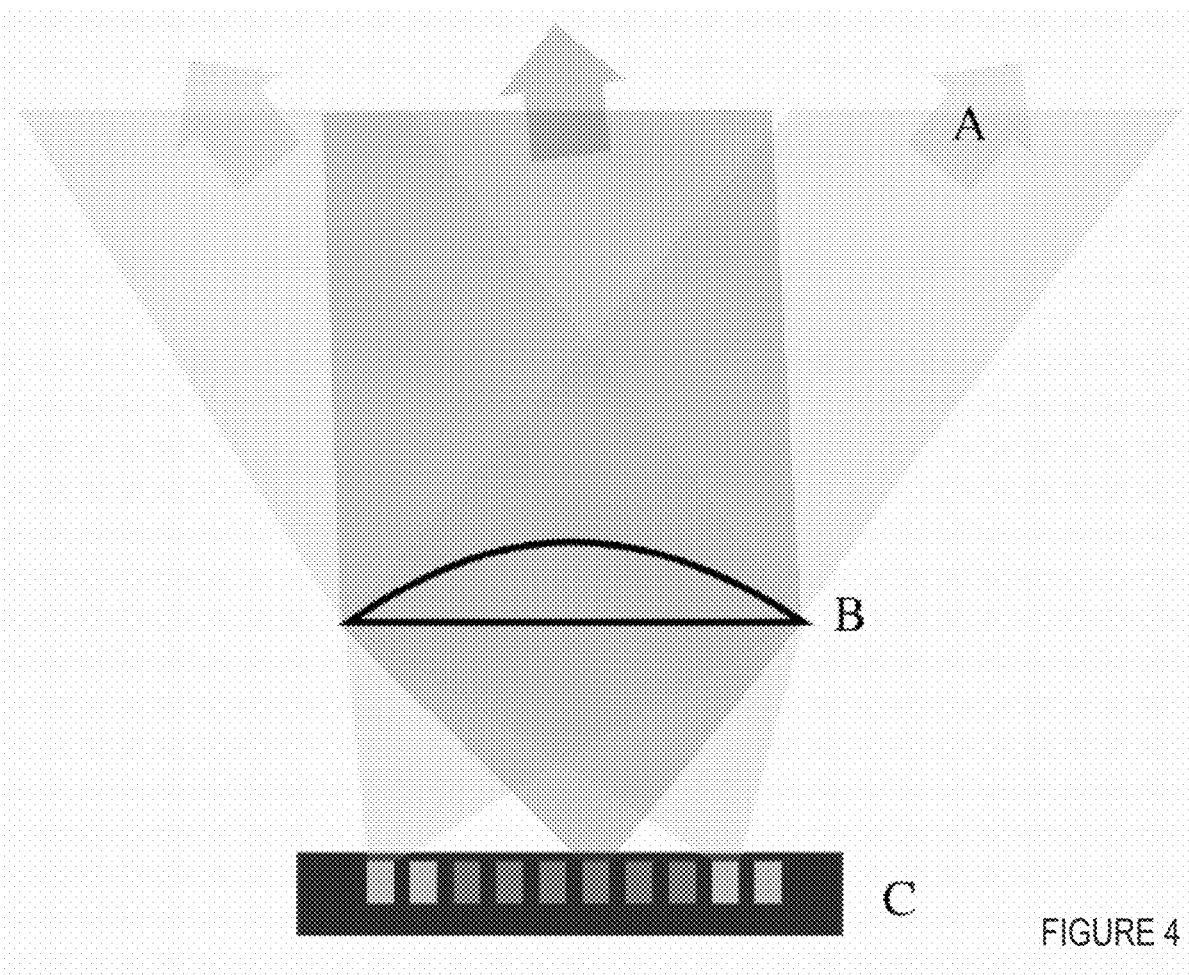
FIG. 4 is a schematic diagram of a single light field pixel defined by a convex lenslet or microlens overlaying an underlying pixel array and disposed at or near its focus to produce a substantially collimated beam, in accordance with one embodiment.

Following with the example of a microlens array, FIG. 4 schematically illustrates a single light field pixel defined by a convex microlens (B) disposed at its focus from a corresponding subset of pixels in an LCD display (C) to produce a substantially collimated beam of light emitted by these pixels, whereby the direction of the beam is controlled by the location of the pixel(s) relative to the microlens. The single light field pixel produces a beam similar to that shown in FIG. 3C where the outside rays are lighter and the majority inside rays are darker. The LCD display (C) emits light which hits the microlens (B) and it results in a beam of substantially collimated light (A).

Figure 5:
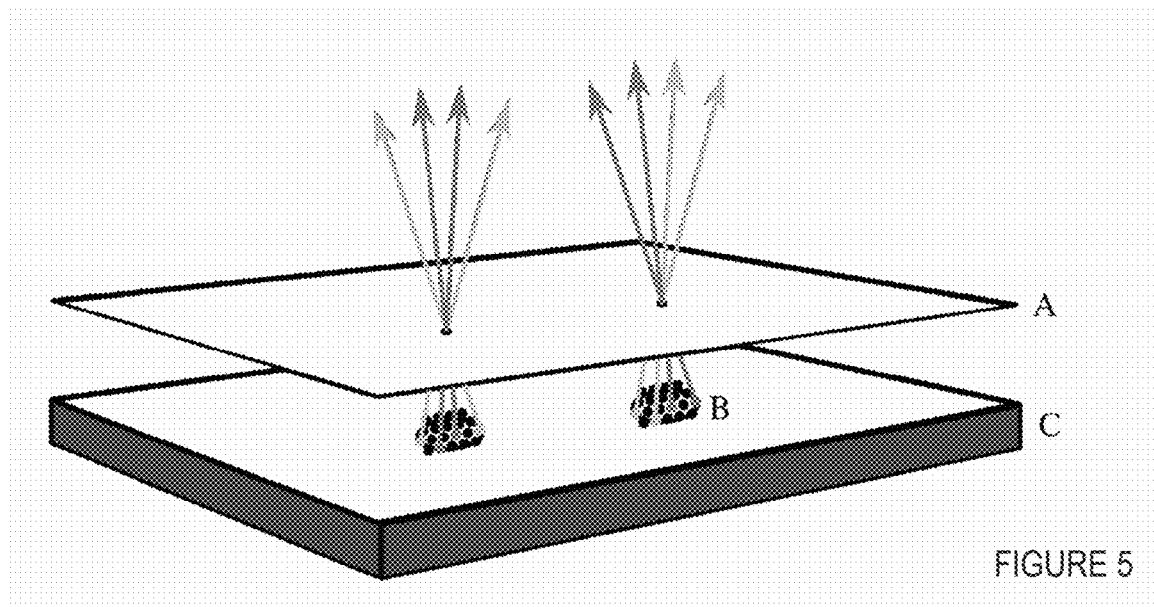
FIG. 5 is another schematic exploded view of an assembly of a light field display in which respective pixel subsets are aligned to emit light through a corresponding microlens or lenslet, in accordance with one embodiment.

Accordingly, upon predictably aligning a particular microlens array with a pixel array, a designated "circle" of pixels will correspond with each microlens and be responsible for delivering light to the pupil through that lens. FIG. 5 schematically illustrates an example of a light field display assembly in which a microlens array (A) sits above an LCD display on a cellphone (C) to have pixels (B) emit light through the microlens array. A ray-tracing algorithm can thus be used to produce a pattern to be displayed on the pixel array below the microlens in order to create the desired virtual image that will effectively correct for the viewer's reduced visual acuity. FIG. 6 provides an example of such a pattern for the letter "Z". Examples of such ray-tracing algorithms are discussed below.

As will be detailed further below, the separation between the microlens array and the pixel array as well as the pitch of the lenses can be selected as a function of various operating characteristics, such as the normal or average operating distance of the display, and/or normal or average operating ambient light levels.

Further, as producing a light field with angular resolution sufficient for accommodation correction over the full viewing 'zone' of a display would generally require an astronomically high pixel density, instead, a correct light field can be produced, in some embodiments, only at or around the location of the user's pupils. To do so, the light field display can be paired with pupil tracking technology to track a location of the user's eyes/pupils relative to the display. The display can then compensate for the user's eye location and produce the correct virtual image, for example, in real time.

In some embodiments, the light field display can render dynamic images at over 30 frames per second on the hardware in a smartphone.

In some embodiments, the light field display can display a virtual image at optical infinity, meaning that any level of accommodation-based presbyopia (e.g. first order) can be corrected for.

In some further embodiments, the light field display can both push the image back or forward, thus allowing for selective image corrections for both hyperopia (far-sightedness) and myopia (nearsightedness). This will be further discussed below in the context of a light field vision testing (e.g. refractor/phoropter) device using the light field display.

In order to demonstrate a working light field solution, and in accordance with one embodiment, the following test was set up. A camera was equipped with a simple lens, to simulate the lens in a human eye and the aperture was set to simulate a normal pupil diameter. The lens was focused to 50 cm away and a phone was mounted 25 cm away. This would approximate a user whose minimal seeing distance is 50 cm and is attempting to use a phone at 25 cm.

With reading glasses, +2.0 diopters would be necessary for the vision correction. A scaled Snellen chart was displayed on the cellphone and a picture was taken, as shown in FIG. 7A. Using the same cellphone, but with a light field assembly in front that uses that cellphone's pixel array, a virtual image compensating for the lens focus is displayed. A picture was again taken, as shown in FIG. 7B, showing a clear improvement.

Figure 9B:
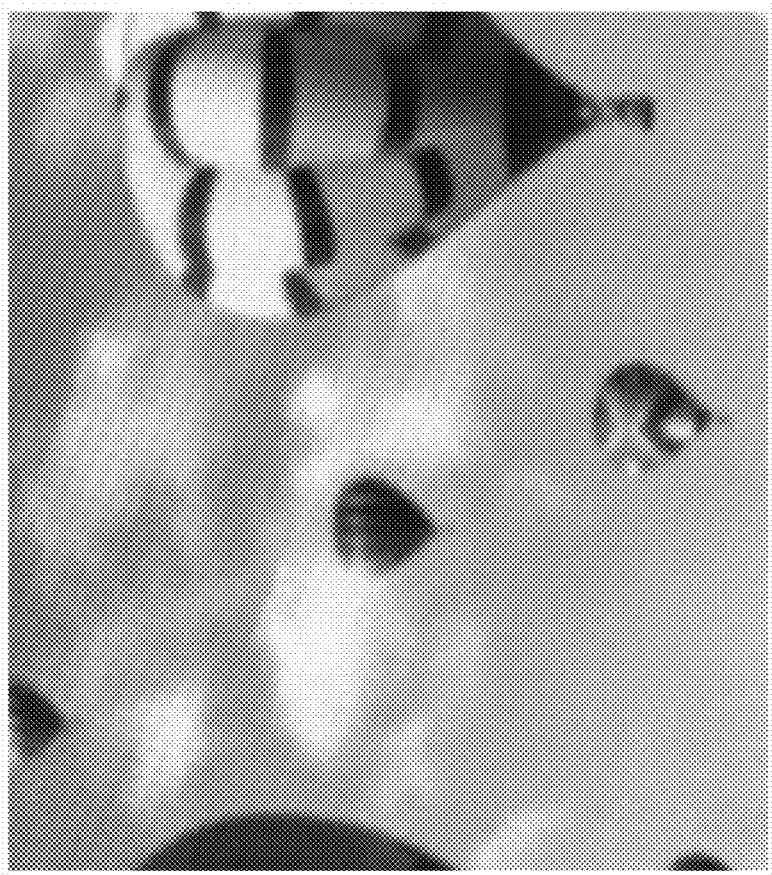
FIGS. 9A and 9B are photographs as illustratively viewed by a viewer with reduced visual acuity without image correction (blurry image in FIG. 9A) and with image correction via a light field display having an angularly mismatched lenslet array (corrected image in FIG. 9B), in accordance with one embodiment.
Figure 9A:
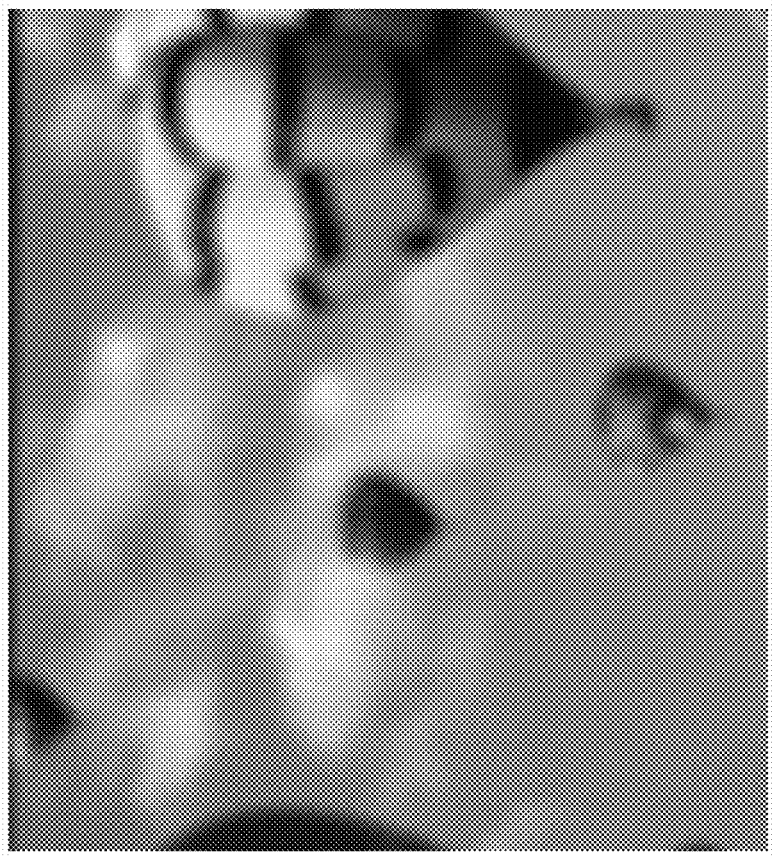

FIGS. 9A and 9B provide another example of results achieved using an exemplary embodiment, in which a colour image was displayed on the LCD display of a Sony™ Xperia™ XZ Premium phone (reported screen resolution of 3840×2160 pixels with 16:9 ratio and approximately 807 pixel-per-inch (ppi) density) without image correction (FIG. 9A) and with image correction through a square fused silica microlens array set at a 2 degree angle relative to the screen's square pixel array and defined by microlenses having a 7.0 mm focus and 200 µm pitch. In this example, the camera lens was again focused at 50 cm with the phone positioned 30 cm away. Another microlens array was used to produce similar results, and consisted of microlenses having a 10.0 mm focus and 150 µm pitch.

Figure 10A:
FIGS. 10A and 10B are photographs as illustratively viewed by a viewer with reduced visual acuity without image correction (blurry image in FIG. 10A) and with image correction via a light field display having an angularly mismatched lenslet array (corrected image in FIG. 10B), in accordance with one embodiment.
Figure 10B:

FIGS. 10A and 10B provide yet another example or results achieved using an exemplary embodiment, in which a colour image was displayed on the LCD display of a Sony™ Xperia™ XZ Premium phone without image correction (FIG. 10A) and with image correction through a square fused silica microlens array set at a 2 degree angle relative to the screen's square pixel array and defined by microlenses having a 10.0 mm focus and 150 µm pitch. In this example, the camera lens was focused at 66 cm with the phone positioned 40 cm away.

Accordingly, a display device as described above and further exemplified below, can be configured to render a corrected image via the light field shaping layer that accommodates for the user's visual acuity. By adjusting the image correction in accordance with the user's actual predefined, set or selected visual acuity level, different users and visual acuity may be accommodated using a same device configuration. That is, in one example, by adjusting corrective image pixel data to dynamically adjust a virtual image distance below/above the display as rendered via the light field shaping layer, different visual acuity levels may be accommodated.

As will be appreciated by the skilled artisan, different image processing techniques may be considered, such as those introduced above and taught by Pamplona and/or Huang, for example, which may also influence other light field parameters to achieve appropriate image correction, virtual image resolution, brightness and the like.

Figure 8:
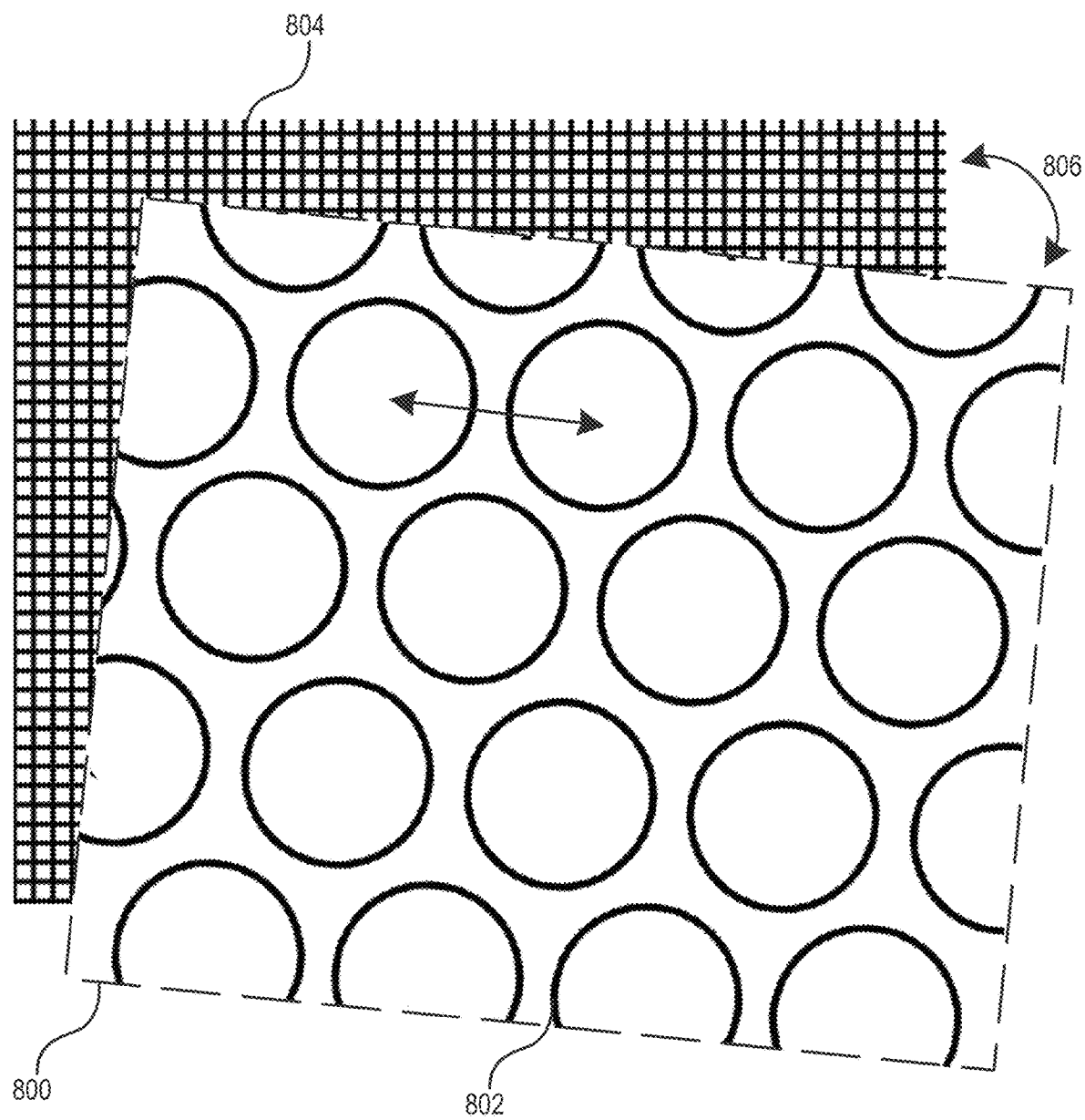
FIG. 8 is a schematic diagram of a portion of a hexagonal lenslet array disposed at an angle relative to an underlying pixel array, in accordance with one embodiment.

With reference to FIG. 8, and in accordance with one embodiment, a microlens array configuration will now be described, in accordance with another embodiment, to provide light field shaping elements in a corrective light field implementation. In this embodiment, the microlens array 800 is defined by a hexagonal array of microlenses 802 disposed so to overlay a corresponding square pixel array 804. In doing so, while each microlens 802 can be aligned with a designated subset of pixels to produce light field pixels as described above, the hexagonal-to-square array mismatch can alleviate certain periodic optical artifacts that may otherwise be manifested given the periodic nature of the optical elements and principles being relied upon to produce the desired optical image corrections. Conversely, a square microlens array may be favoured when operating a digital display comprising a hexagonal pixel array.

In some embodiments, as illustrated in FIG. 8, the microlens array 800 may further or alternatively overlaid at an angle 806 relative to the underlying pixel array, which can further or alternatively alleviate period optical artifacts.

In yet some further or alternative embodiments, a pitch ratio between the microlens array and pixel array may be deliberately selected to further or alternatively alleviate periodic optical artifacts. For example, a perfectly matched pitch ratio (i.e. an exact integer number of display pixels per microlens) is most likely to induce periodic optical artifacts, whereas a pitch ratio mismatch can help reduce such occurrences. Accordingly, in some embodiments, the pitch ratio will be selected to define an irrational number, or at least, an irregular ratio, so to minimize periodic optical artifacts. For instance, a structural periodicity can be defined so to reduce the number of periodic occurrences within the dimensions of the display screen at hand, e.g. ideally selected so to define a structural period that is greater than the size of the display screen being used.

While this example is provided within the context of a microlens array, similar structural design considerations may be applied within the context of a parallax barrier, diffractive barrier or combination thereof.

Figure 11:
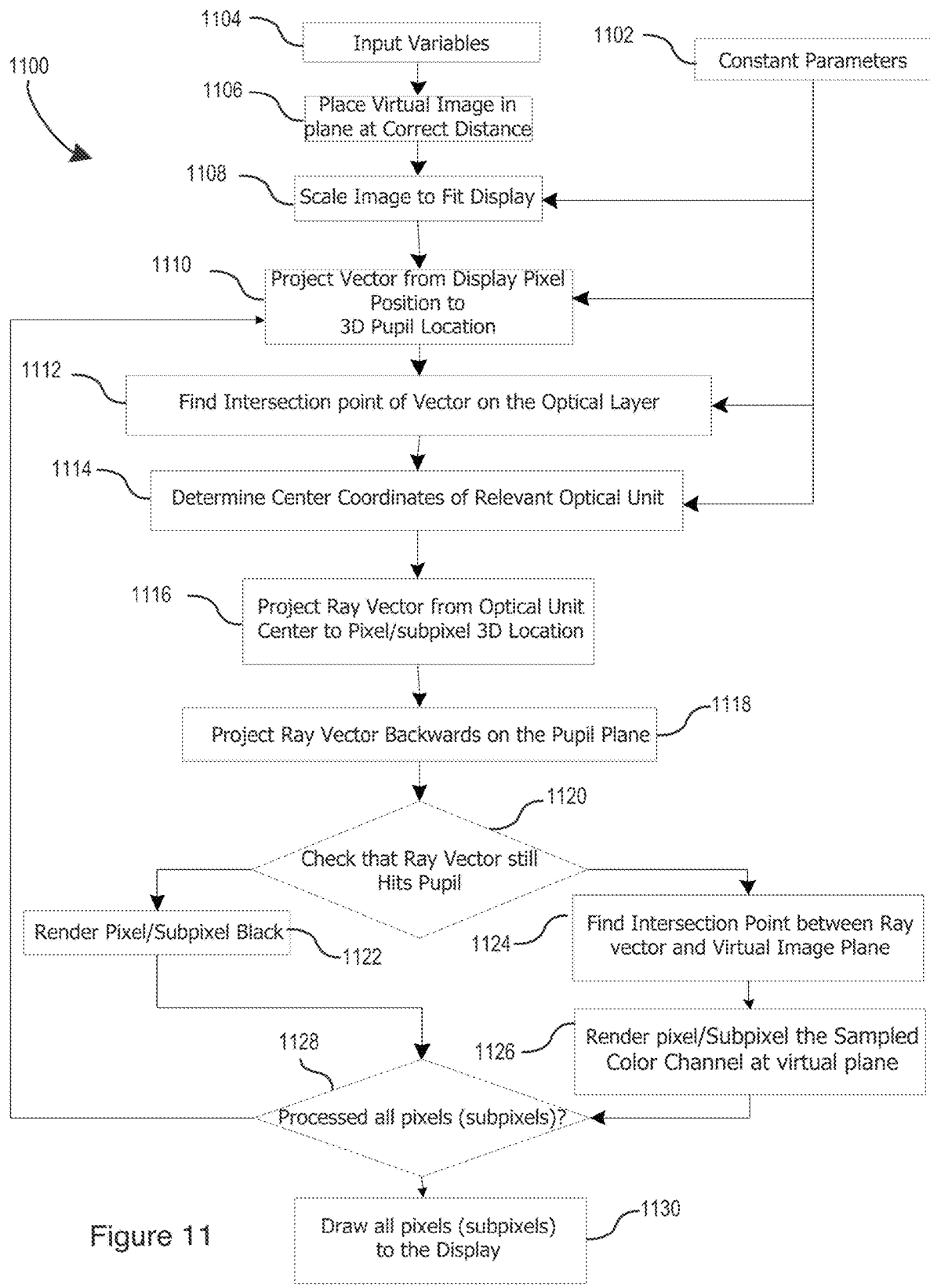
FIG. 11 is a process flow diagram of an illustrative ray-tracing rendering process, in accordance with one embodiment.
Figure 12:
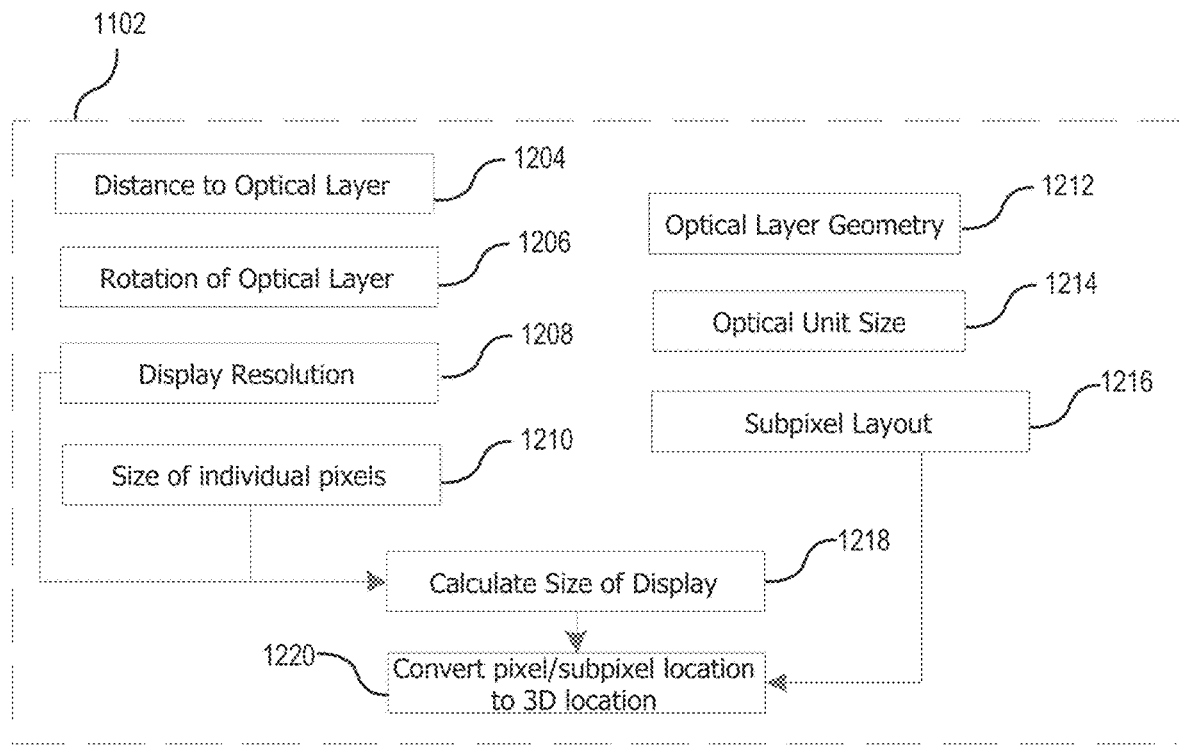
FIGS. 12 and 13 are process flow diagrams of exemplary input constant parameters and variables, respectively, for the ray-tracing rendering process of FIG. 11, in accordance with one embodiment.
Figure 13:
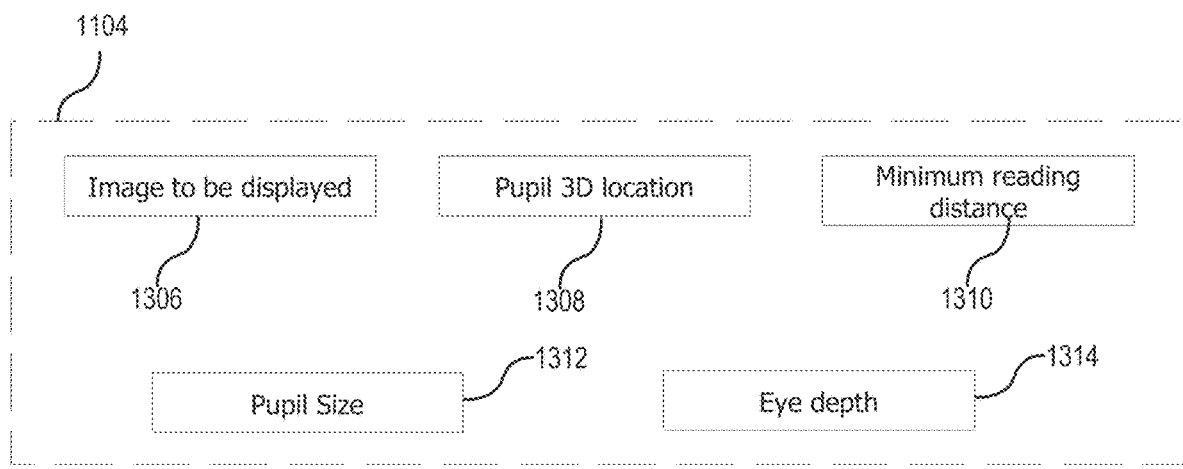

With reference to FIGS. 11 to 13, and in accordance with one embodiment, an exemplary computationally implemented ray-tracing method for rendering an adjusted image via an array of light field shaping elements, in this example provided by a light field shaping layer (LFSL) disposed relative to a set of underlying display pixels, that accommodates for the user's reduced visual acuity will now be described. In this example, for illustrative purposes, adjustment of a single image (i.e. the image as whole) is being implemented without consideration for distinct image portions. Further examples below will specifically address modification of the following example for adaptively adjusting distinct image portions.

In this exemplary embodiment, a set of constant parameters 1102 may be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1104 which are expected to change either at each rendering iteration or at least between each user's viewing session.

As illustrated in FIG. 12, the list of constant parameters 1102 may include, without limitations, the distance 1204 between the display and the LFSL, the in-plane rotation angle 1206 between the display and LFSL frames of reference, the display resolution 1208, the size of each individual pixel 1210, the optical LFSL geometry 1212, the size of each optical element 1214 within the LFSL and optionally the subpixel layout 1216 of the display. Moreover, both the display resolution 1208 and the size of each individual pixel 1210 may be used to pre-determine both the absolute size of the display in real units (i.e. in mm) and the three-dimensional position of each pixel within the display. In some embodiments where the subpixel layout 1216 is available, the position within the display of each subpixel may also be pre-determined. These three-dimensional location/positions are usually calculated using a given frame of reference located somewhere within the plane of the display, for example a corner or the middle of the display, although other reference points may be chosen. Concerning the optical layer geometry 1212, different geometries may be considered, for example a hexagonal geometry such as the one shown in FIG. 8. Finally, by combining the distance 1204, the rotation angle 1206, and the geometry 1212 with the optical element size 1214, it is possible to similarly pre-determine the three-dimensional location/position of each optical element center with respect to the display's same frame of reference.

FIG. 13 meanwhile illustratively lists an exemplary set of input variables 1104 for method 1100, which may include any input data fed into method 1100 that may reasonably change during a user's single viewing session, and may thus include without limitation: the image(s) to be displayed 1306 (e.g. pixel data such as on/off, colour, brightness, etc.), the three-dimensional pupil location 1308 (e.g. in embodiments implementing active eye/pupil tracking methods) and/or pupil size 1312 and the minimum reading distance 1310 (e.g. one or more parameters representative of the user's reduced visual acuity or condition). In some embodiments, the eye depth 1314 may also be used. The image data 1306, for example, may be representative of one or more digital images to be displayed with the digital pixel display. This image may generally be encoded in any data format used to store digital images known in the art. In some embodiments, images 1306 to be displayed may change at a given framerate.

The pupil location 1308, in one embodiment, is the three-dimensional coordinates of at least one of the user's pupils' center with respect to a given reference frame, for example a point on the device or display. This pupil location 1308 may be derived from any eye/pupil tracking method known in the art. In some embodiments, the pupil location 1308 may be determined prior to any new iteration of the rendering algorithm, or in other cases, at a lower framerate. In some embodiments, only the pupil location of a single user's eye may be determined, for example the user's dominant eye (i.e. the one that is primarily relied upon by the user). In some embodiments, this position, and particularly the pupil distance to the screen may otherwise or additionally be rather approximated or adjusted based on other contextual or environmental parameters, such as an average or preset user distance to the screen (e.g. typical reading distance for a given user or group of users; stored, set or adjustable driver distance in a vehicular environment; etc.).

In the illustrated embodiment, the minimum reading distance 1310 is defined as the minimal focus distance for reading that the user's eye(s) may be able to accommodate (i.e. able to view without discomfort). In some embodiments, different values of the minimum reading distance 1310 associated with different users may be entered, for example, as can other adaptive vision correction parameters be considered depending on the application at hand and vision correction being addressed. In some embodiments, minimum reading distance 1310 may be derived from an eye prescription (e.g. glasses prescription or contact prescription) or similar. It may, for example, correspond to the near point distance corresponding to the uncorrected user's eye, which can be calculated from the prescribed corrective lens power assuming that the targeted near point was at 25 cm.

Figure 14A:
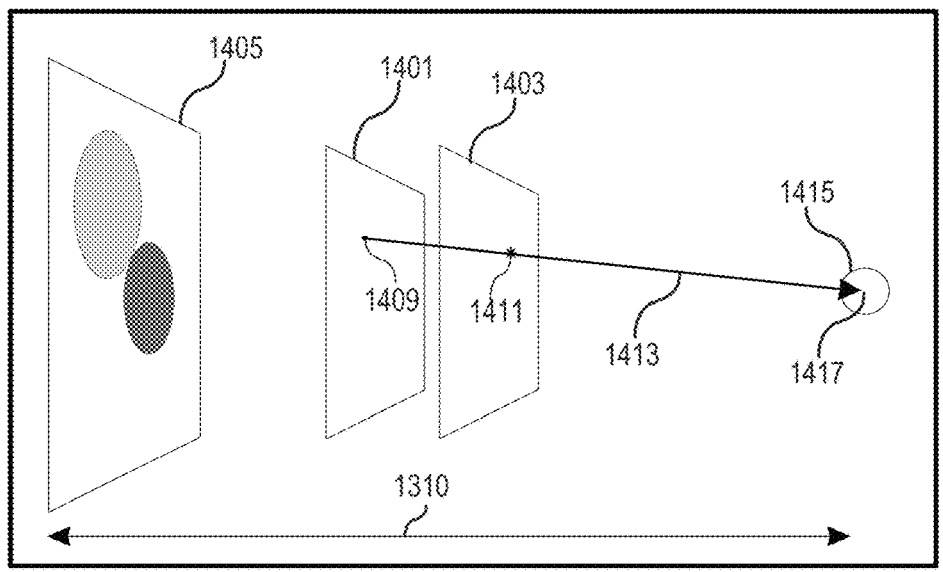
FIGS. 14A to 14C are schematic diagrams illustrating certain process steps of FIG. 11.
Figure 14B:
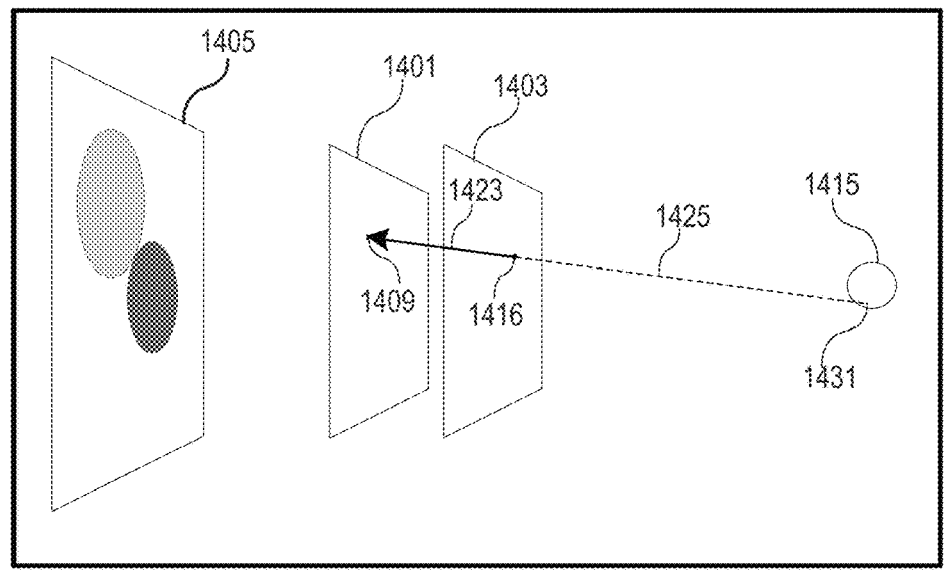
Figure 14C:
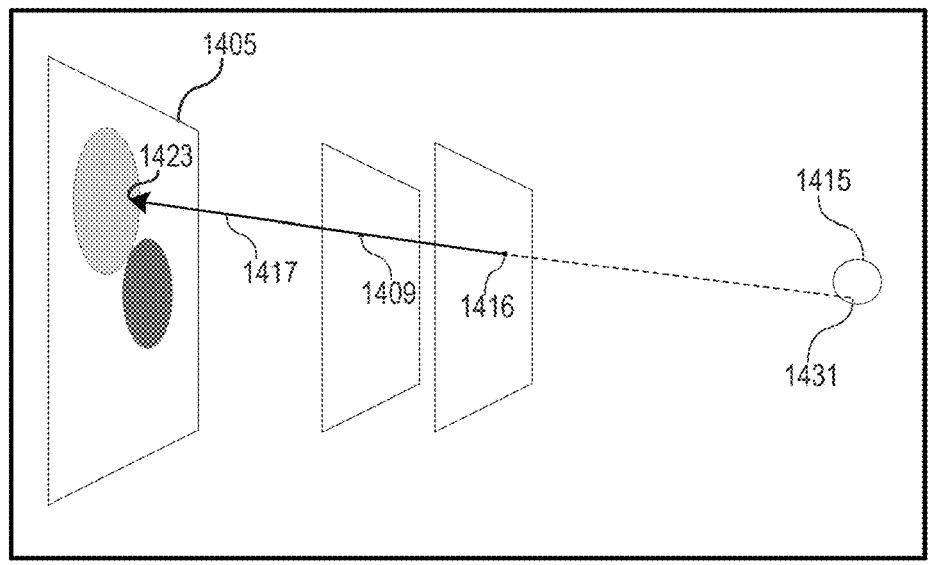

With added reference to FIGS. 14A to 14C, once parameters 1102 and variables 1104 have been set, the method of FIG. 11 then proceeds with step 1106, in which the minimum reading distance 1310 (and/or related parameters) is used to compute the position of a virtual (adjusted) image plane 1405 with respect to the device's display, followed by step 1108 wherein the size of image 1306 is scaled within the image plane 1405 to ensure that it correctly fills the pixel display 1401 when viewed by the distant user. This is illustrated in FIG. 14A, which shows a diagram of the relative positioning of the user's pupil 1415, the light field shaping layer 1403, the pixel display 1401 and the virtual image plane 1405. In this example, the size of image 1306 in image plane 1405 is increased to avoid having the image as perceived by the user appear smaller than the display's size.

An exemplary ray-tracing methodology is described in steps 1110 to 1128 of FIG. 11, at the end of which the output color of each pixel of pixel display 1401 is known so as to virtually reproduce the light field emanating from an image 1306 positioned at the virtual image plane 1405. In FIG. 11, these steps are illustrated in a loop over each pixel in pixel display 1401, so that each of steps 1110 to 1126 describes the computations done for each individual pixel. However, in some embodiments, these computations need not be executed sequentially, but rather, steps 1110 to 1128 may be executed in parallel for each pixel or a subset of pixels at the same time. Indeed, as will be discussed below, this exemplary method is well suited to vectorization and implementation on highly parallel processing architectures such as GPUs.

As illustrated in FIG. 14A, in step 1110, for a given pixel 1409 in pixel display 1401, a trial vector 1413 is first generated from the pixel's position to the center position 1417 of pupil 1415. This is followed in step 1112 by calculating the intersection point 1411 of vector 1413 with the LFSL 1403.

The method then finds, in step 1114, the coordinates of the center 1416 of the LFSL optical element closest to intersection point 1411. This step may be computationally intensive and will be discussed in more depth below. Once the position of the center 1416 of the optical element is known, in step 1116, a normalized unit ray vector is generated from drawing and normalizing a vector 1423 drawn from center position 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. The direction of this ray vector will be used to find the portion of image 1306, and thus the associated color, represented by pixel 1409. But first, in step 1118, this ray vector is projected backwards to the plane of pupil 1415, and then in step 1120, the method verifies that the projected ray vector 1425 is still within pupil 1415 (i.e. that the user can still "see" it). Once the intersection position, for example location 1431 in FIG. 14B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

If this deviation is deemed to be too large (i.e. light emanating from pixel 1409 channeled through optical element 1416 is not perceived by pupil 1415), then in step 1122, the method flags pixel 1409 as unnecessary and to simply be turned off or render a black color. Otherwise, as shown in FIG. 14C, in step 1124, the ray vector is projected once more towards virtual image plane 1405 to find the position of the intersection point 1423 on image 1306. Then in step 1126, pixel 1409 is flagged as having the color value associated with the portion of image 1306 at intersection point 1423.

In some embodiments, method 1100 is modified so that at step 1120, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1220 continues to step 1124. At step 1126, the pixel color value assigned to pixel 1409 is chosen to be somewhere between the full color value of the portion of image 1306 at intersection point 1423 or black, depending on the value of the interpolation function used at step 1120 (1 or 0).

In yet other embodiments, pixels found to illuminate a designated area around the pupil may still be rendered, for example, to produce a buffer zone to accommodate small movements in pupil location, for example, or again, to address potential inaccuracies, misalignments or to create a better user experience.

In some embodiments, steps 1118, 1120 and 1122 may be avoided completely, the method instead going directly from step 1116 to step 1124. In such an exemplary embodiment, no check is made that the ray vector hits the pupil or not, but instead the method assumes that it always docs.

Once the output colors of all pixels have been determined, these are finally rendered in step 1130 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

With reference to FIGS. 19 and 20A to 20D, and in accordance with one embodiment, another exemplary computationally implemented ray-tracing method for rendering an adjusted image via the light field shaping layer (LFSL) that accommodates for the user's reduced visual acuity, for example, will now be described. Again, for illustrative purposes, in this example, adjustment of a single image (i.e. the image as whole) is being implemented without consideration for distinct image portions. Further examples below will specifically address modification of the following example for adaptively adjusting distinct image portions.

In this embodiment, the adjusted image portion associated with a given pixel/subpixel is computed (mapped) on the retina plane instead of the virtual image plane considered in the above example, again in order to provide the user with a designated image perception adjustment. Therefore, the currently discussed exemplary embodiment shares some steps with the method of FIG. 11. Indeed, a set of constant parameters 1102 may also be pre-determined. These may include, for example, any data that are not expected to significantly change during a user's viewing session, for instance, which are generally based on the physical and functional characteristics of the display for which the method is to be implemented, as will be explained below. Similarly, every iteration of the rendering algorithm may use a set of input variables 1104 which are expected to change either at each rendering iteration or at least between each user viewing session. The list of possible variables and constants is substantially the same as the one disclosed in FIGS. 12 and 13 and will thus not be replicated here.

Once parameters 1102 and variables 1104 have been set, this second exemplary ray-tracing methodology proceeds from steps 1910 to 1936, at the end of which the output color of each pixel of the pixel display is known so as to virtually reproduce the light field emanating from an image perceived to be positioned at the correct or adjusted image distance, in one example, so to allow the user to properly focus on this adjusted image (i.e. having a focused image projected on the user's retina) despite a quantified visual aberration. In FIG. 19, these steps are illustrated in a loop over each pixel in pixel display 1401, so that each of steps 1910 to 1934 describes the computations done for each individual pixel. However, in some embodiments, these computations need not be executed sequentially, but rather, steps 1910 to 1934 may be executed in parallel for each pixel or a subset of pixels at the same time. Indeed, as will be discussed below, this second exemplary method is also well suited to vectorization and implementation on highly parallel processing architectures such as GPUs.

Referencing once more FIG. 14A, in step 1910 (as in step 1110), for a given pixel in pixel display 1401, a trial vector 1413 is first generated from the pixel's position to pupil center 1417 of the user's pupil 1415. This is followed in step 1912 by calculating the intersection point of vector 1413 with optical layer 1403.

From there, in step 1914, the coordinates of the optical element center 1416 closest to intersection point 1411 are determined. This step may be computationally intensive and will be discussed in more depth below. As shown in FIG. 14B, once the position of the optical element center 1416 is known, in step 1916, a normalized unit ray vector is generated from drawing and normalizing a vector 1423 drawn from optical element center 1416 to pixel 1409. This unit ray vector generally approximates the direction of the light field emanating from pixel 1409 through this particular light field element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan. In step 1918, this ray vector is projected backwards to pupil 1415, and then in step 1920, the method ensures that the projected ray vector 1425 is still within pupil 1415 (i.e. that the user can still "see" it). Once the intersection position, for example location 1431 in FIG. 14B, of projected ray vector 1425 with the pupil plane is known, the distance between the pupil center 1417 and the intersection point 1431 may be calculated to determine if the deviation is acceptable, for example by using a pre-determined pupil size and verifying how far the projected ray vector is from the pupil center.

Now referring to FIGS. 20A to 20D, steps 1921 to 1929 of method 1900 will be described. Once optical element center 1416 of the relevant optical unit has been determined, at step 1921, a vector 2004 is drawn from optical element center 1416 to pupil center 1417. Then, in step 1923, vector 2004 is projected further behind the pupil plane onto focal plane 2006 (location where any light rays originating from optical layer 1403 would be focused by the eye) to locate focal point 2008. For a user with perfect vision, focal plane 2006 would be located at the same location as retina plane 2010, but in this example, focal plane 2006 is located behind retina plane 2010, which would be expected for a user with some form of farsightedness. The position of focal plane 2006 may be derived from the user's minimum reading distance 1310, for example, by deriving therefrom the focal length of the user's eye. Other manually input or computationally or dynamically adjustable means may also or alternatively be considered to quantify this parameter.

The skilled artisan will note that any light ray originating from optical element center 1416, no matter its orientation, will also be focused onto focal point 2008, to a first approximation. Therefore, the location on retina plane 2010 onto which light entering the pupil at intersection point 1431 will converge may be approximated by drawing a straight line between intersection point 1431 where ray vector 1425 hits the pupil 1415 and focal point 2008 on focal plane 2006. The intersection of this line with retina plane 2010 (retina image point 2012) is thus the location on the user's retina corresponding to the image portion that will be reproduced by corresponding pixel 1409 as perceived by the user. Therefore, by comparing the relative position of retina point 2012 with the overall position of the projected image on the retina plane 2010, the relevant adjusted image portion associated with pixel 1409 may be computed.

To do so, at step 1927, the corresponding projected image center position on retina plane 2010 is calculated. Vector 2016 is generated originating from the center position of display 1401 (display center position 2018) and passing through pupil center 1417. Vector 2016 is projected beyond the pupil plane onto retina plane 2010, wherein the associated intersection point gives the location of the corresponding retina image center 2020 on retina plane 2010. The skilled technician will understand that step 1927 could be performed at any moment prior to step 1929, once the relative pupil center location 1417 is known in input variables step 1904. Once image center 2020 is known, one can then find the corresponding image portion of the selected pixel/subpixel at step 1929 by calculating the x/y coordinates of retina image point 2012 relative to retina image center 2020 on the retina, scaled to the x/y retina image size 2031.

Figure 20A:
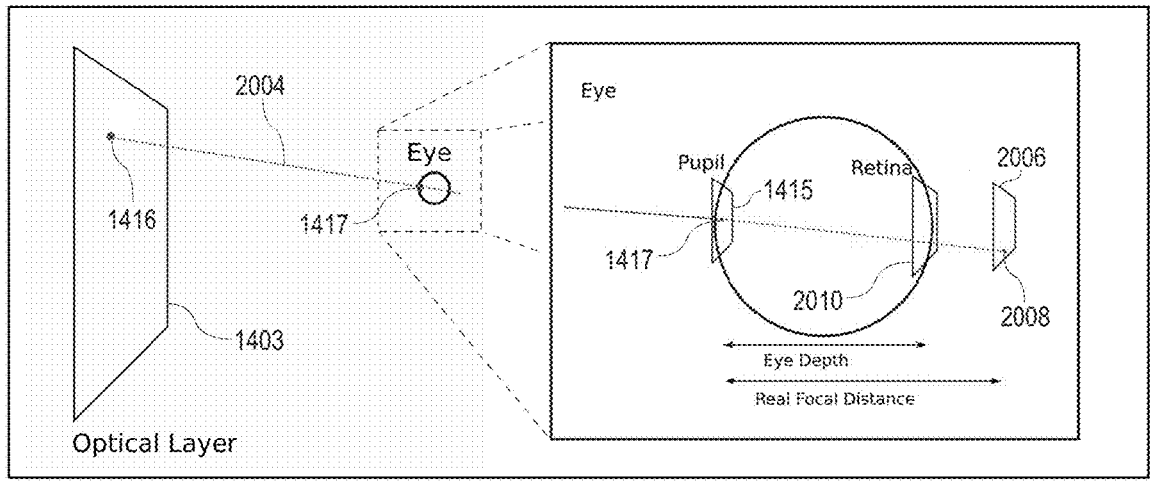
FIGS. 20A to 20D are schematic diagrams illustrating certain process steps of FIG. 19.
Figure 20B:
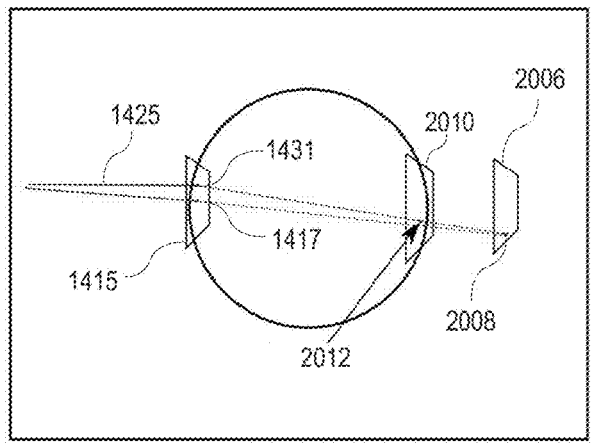
Figure 20C:
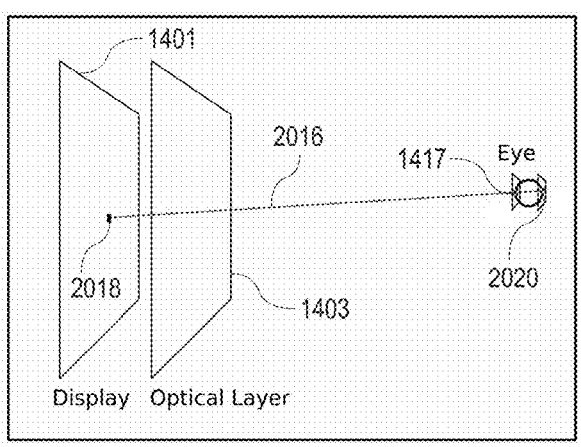
Figure 20D:
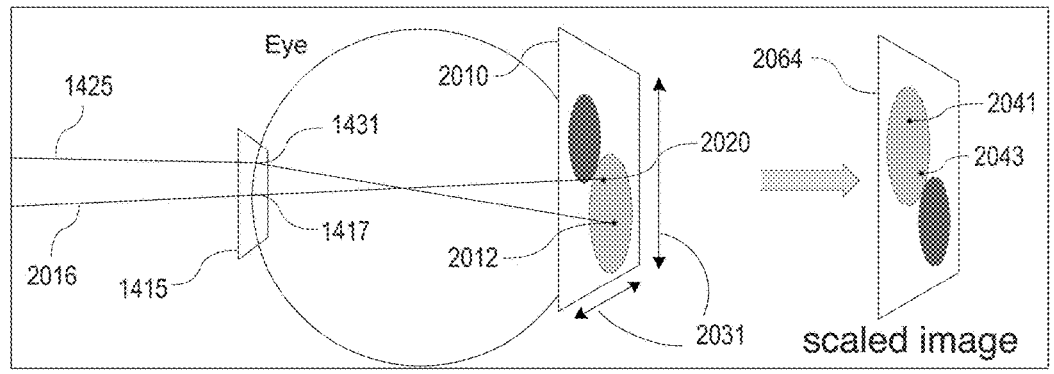

This retina image size 2031 may be computed by calculating the magnification of an individual pixel on retina plane 2010, for example, which may be approximately equal to the x or y dimension of an individual pixel multiplied by the eye depth 1314 and divided by the absolute value of the distance to the eye (i.e. the magnification of pixel image size from the eye lens). Similarly, for comparison purposes, the input image is also scaled by the image x/y dimensions to produce a corresponding scaled input image 2064. Both the scaled input image and scaled retina image should have a width and height between −0.5 to 0.5 units, enabling a direct comparison between a point on the scaled retina image 2010 and the corresponding scaled input image 2064, as shown in FIG. 20D.

From there, the image portion position 2041 relative to retina image center position 2043 in the scaled coordinates (scaled input image 2064) corresponds to the inverse (because the image on the retina is inverted) scaled coordinates of retina image point 2012 with respect to retina image center 2020. The associated color with image portion position 2041 is therefrom extracted and associated with pixel 1409.

In some embodiments, method 1900 may be modified so that at step 1920, instead of having a binary choice between the ray vector hitting the pupil or not, one or more smooth interpolation function (i.e. linear interpolation, Hermite interpolation or similar) are used to quantify how far or how close the intersection point 1431 is to the pupil center 1417 by outputting a corresponding continuous value between 1 or 0. For example, the assigned value is equal to 1 substantially close to pupil center 1417 and gradually change to 0 as the intersection point 1431 substantially approaches the pupil edges or beyond. In this case, the branch containing step 1122 is ignored and step 1920 continues to step 1124. At step 1931, the pixel color value assigned to pixel 1409 is chosen to be somewhere between the full color value of the portion of image 1306 at intersection point 1423 or black, depending on the value of the interpolation function used at step 1920 (1 or 0).

In yet other embodiments, pixels found to illuminate a designated area around the pupil may still be rendered, for example, to produce a buffer zone to accommodate small movements in pupil location, for example, or again, to address potential inaccuracies or misalignments.

Once the output colors of all pixels in the display have been determined (check at step 1934 is true), these are finally rendered in step 1936 by pixel display 1401 to be viewed by the user, therefore presenting a light field corrected image. In the case of a single static image, the method may stop here. However, new input variables may be entered and the image may be refreshed at any desired frequency, for example because the user's pupil moves as a function of time and/or because instead of a single image a series of images are displayed at a given framerate.

As will be appreciated by the skilled artisan, selection of the adjusted image plane onto which to map the input image in order to adjust a user perception of this input image allows for different ray tracing approaches to solving a similar challenge, that is of creating an adjusted image using the light field display that can provide an adjusted user perception, such as addressing a user's reduce visual acuity. While mapping the input image to a virtual image plane set at a designated minimum (or maximum) comfortable viewing distance can provide one solution, the alternate solution may allow accommodation of different or possibly more extreme visual aberrations. For example, where a virtual image is ideally pushed to infinity (or effectively so), computation of an infinite distance becomes problematic. However, by designating the adjusted image plane as the retinal plane, the illustrative process of FIG. 19 can accommodate the formation of a virtual image effectively set at infinity without invoking such computational challenges. Likewise, while first order focal length aberrations are illustratively described with reference to FIG. 19, higher order or other optical anomalies may be considered within the present context, whereby a desired retinal image is mapped out and traced while accounting for the user's optical aberration(s) so to compute adjusted pixel data to be rendered in producing that image. These and other such considerations should be readily apparent to the skilled artisan.

While the computations involved in the above described ray-tracing algorithms (steps 1110 to 1128 of FIG. 11 or steps 1920 to 1934 of FIG. 19) may be done on general CPUs, it may be advantageous to use highly parallel programming schemes to speed up such computations. While in some embodiments, standard parallel programming libraries such as Message Passing Interface (MPI) or OPENMP may be used to accelerate the light field rendering via a general-purpose CPU, the light field computations described above are especially tailored to take advantage of graphical processing units (GPU), which are specifically tailored for massively parallel computations. Indeed, modern GPU chips are characterized by the very large number of processing cores, and an instruction set that is commonly optimized for graphics. In typical use, each core is dedicated to a small neighborhood of pixel values within an image, e.g., to perform processing that applies a visual effect, such as shading, fog, affine transformation, etc. GPUs are usually also optimized to accelerate exchange of image data between such processing cores and associated memory, such as RGB frame buffers. Furthermore, smartphones are increasingly being equipped with powerful GPUs to speed the rendering of complex screen displays, e.g., for gaming, video, and other image-intensive applications. Several programming frameworks and languages tailored for programming on GPUs include, but are not limited to, CUDA, OpenCL, OpenGL Shader Language (GLSL), High-Level Shader Language (HLSL) or similar. However, using GPUs efficiently may be challenging and thus require creative steps to leverage their capabilities, as will be discussed below.

With reference to FIGS. 15 to 18C and in accordance with one exemplary embodiment, an exemplary process for computing the center position of an associated light field shaping element in the ray-tracing process of FIG. 11 (or FIG. 19) will now be described. The series of steps are specifically tailored to avoid code branching, so as to be increasingly efficient when run on GPUs (i.e. to avoid so called "warp divergence"). Indeed, with GPUs, because all the processors must execute identical instructions, divergent branching can result in reduced performance.

Figure 15:
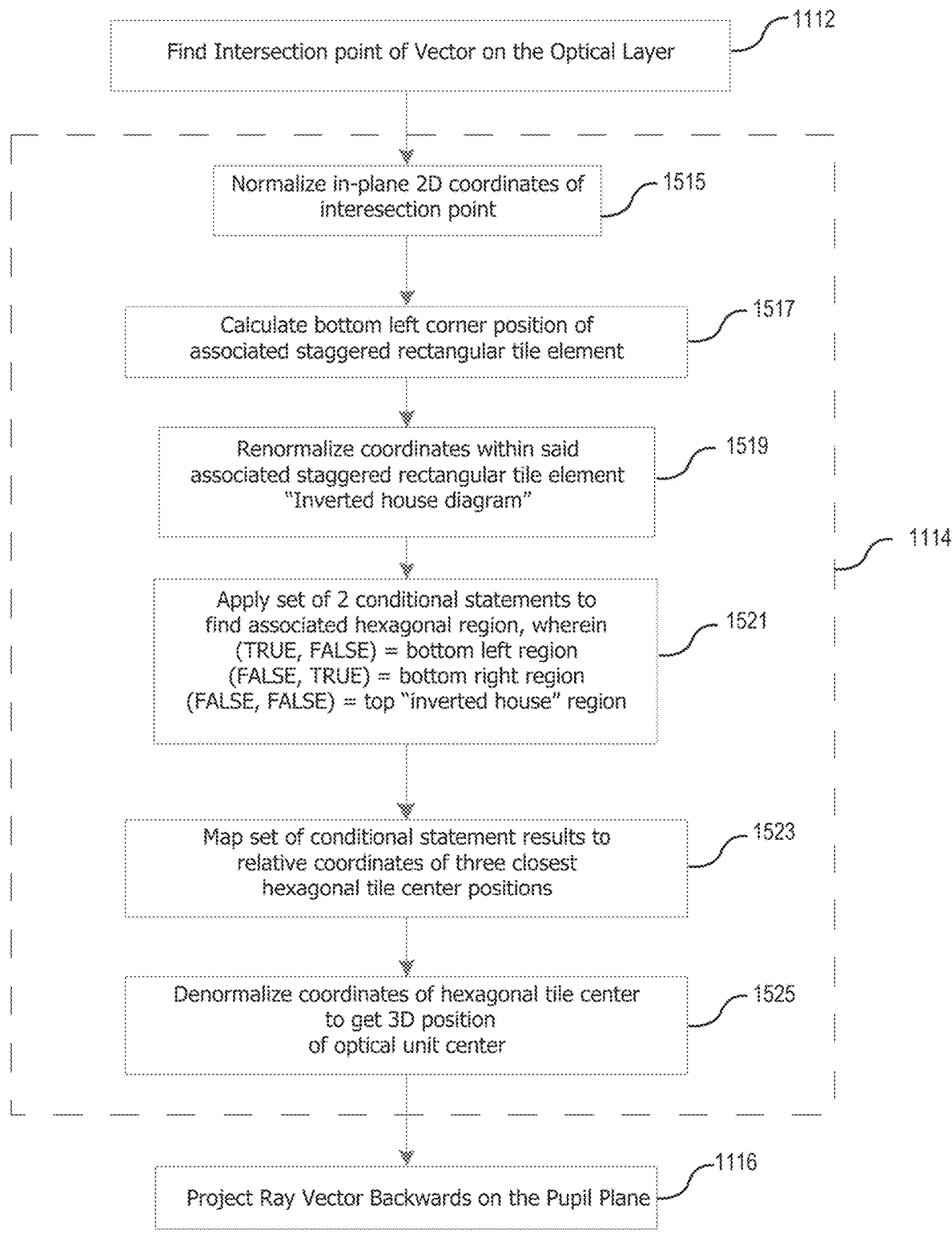
FIG. 15 is a process flow diagram of an exemplary process for computing the center position of an associated light field shaping unit in the ray-tracing rendering process of FIG. 11, in accordance with one embodiment.

With reference to FIG. 15, and in accordance with one embodiment, step 1114 of FIG. 11 is expanded to include steps 1515 to 1525. A similar discussion can readily be made in respect of step 1914 of FIG. 19, and thus need not be explicitly detailed herein. The method receives from step 1112 the 2D coordinates of the intersection point 1411 (illustrated in FIG. 14A) of the trial vector 1413 with optical layer 1403. As discussed with respect to the exemplary embodiment of FIG. 8, there may be a difference in orientation between the frames of reference of the optical layer (hexagonal array of microlenses 802 in FIG. 8, for example) and of the corresponding pixel display (square pixel array 804 in FIG. 8, for example). This is why, in step 1515, these input intersection coordinates, which are initially calculated from the display's frame of reference, may first be rotated to be expressed from the light field shaping layer's frame of reference and optionally normalized so that each individual light shaping element has a width and height of 1 unit. The following description will be equally applicable to any light field shaping layer having a hexagonal geometry like the exemplary embodiment of FIG. 8. Note however that the method steps 1515 to 1525 described herein may be equally applied to any kind of light field shaping layer sharing the same geometry (i.e. not only a microlens array, but pinhole arrays as well, etc.). Likewise, while the following example is specific to an exemplary hexagonal array of LFSL elements definable by a hexagonal tile array of regular hexagonal tiles, other geometries may also benefit from some or all of the features and/or advantages of the herein-described and illustrated embodiments. For example, different hexagonal LFSL element arrays, such as stretched/elongated, skewed and/or rotated arrays may be considered, as can other nested array geometries in which adjacent rows and/or columns of the LFSL array at least partially "overlap" or inter-nest. For instance, as will be described further below, hexagonal arrays and like nested array geometries will generally provide for a commensurately sized rectangular/square tile of an overlaid rectangular/square array or grid to naturally encompass distinct regions as defined by two or more adjacent underlying nested array tiles, which can be used to advantage in the examples provided below. In yet other embodiments, the processes discussed herein may be applied to rectangular and/or square LFSL element arrays. Other LFSL element array geometries may also be considered, as will be appreciated by the skilled artisan upon reading of the following example, without departing from the general scope and nature of the present disclosure.

Figure 16A:
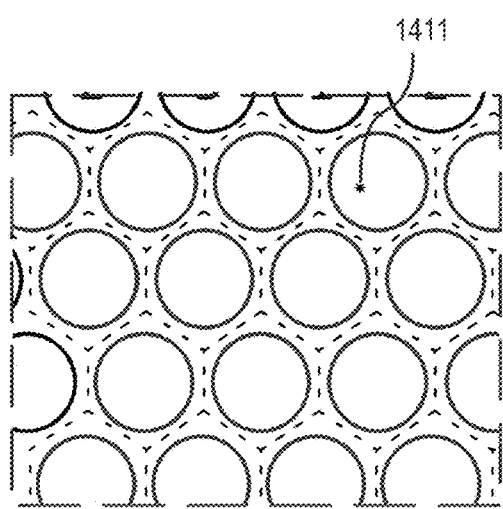
FIGS. 16A and 16B are schematic diagrams illustrating an exemplary hexagonal light field shaping layer with a corresponding hexagonal tile array, in accordance with one embodiment.
Figure 16B:
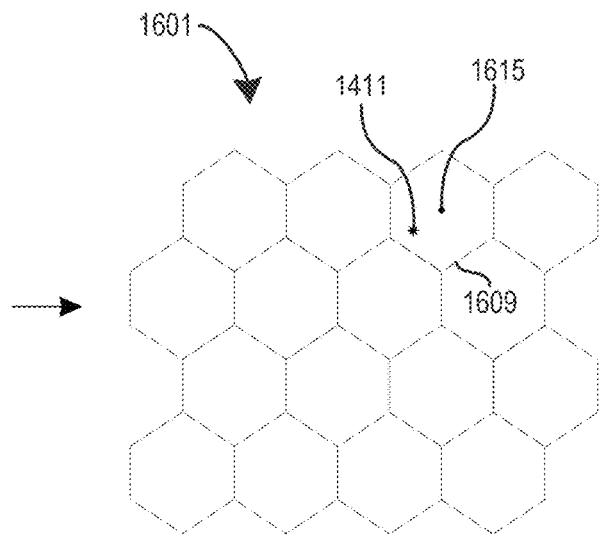

For hexagonal geometries, as illustrated in FIGS. 16A and 16B, the hexagonal symmetry of the light field shaping layer 1403 may be represented by drawing an array of hexagonal tiles 1601, each centered on their respective light field shaping element, so that the center of a hexagonal tile element is more or less exactly the same as the center position of its associated light field shaping element. Thus, the original problem is translated to a slightly similar one whereby one now needs to find the center position 1615 of the associated hexagonal tile 1609 closest to the intersection point 1411, as shown in FIG. 16B.

Figure 17A:
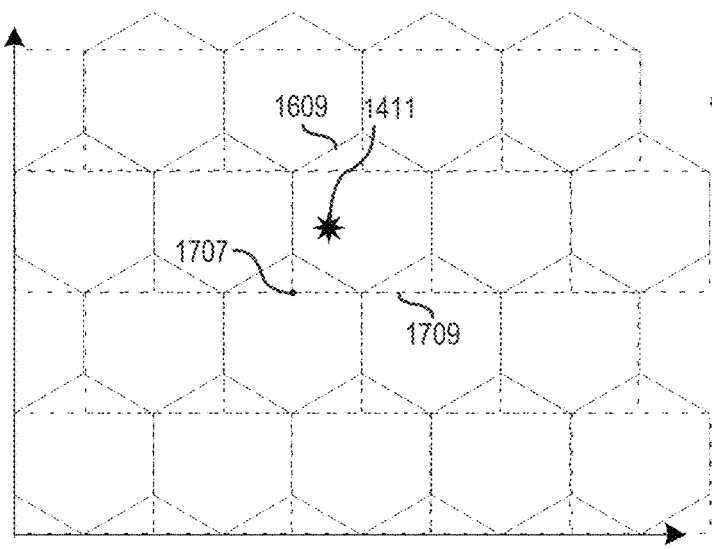
FIGS. 17A and 17B are schematic diagrams illustrating overlaying a staggered rectangular tile array over the hexagonal tile array of FIGS. 16A and 16B, in accordance with one embodiment.

To solve this problem, the array of hexagonal tiles 1601 may be superimposed on or by a second array of staggered rectangular tiles 1705, in such a way as to make an "inverted house" diagram within each rectangle, as clearly illustrated in FIG. 17A, namely defining three linearly segregated tile regions for each rectangular tile, one region predominantly associated with a main underlying hexagonal tile, and two other opposed triangular regions associated with adjacent underlying hexagonal tiles. In doing so, the nested hexagonal tile geometry is translated to a rectangular tile geometry having distinct linearly segregated tile regions defined therein by the edges of underlying adjacently disposed hexagonal tiles. Again, while regular hexagons are used to represent the generally nested hexagonal LFSL element array geometry, other nested tile geometries may be used to represent different nested element geometries. Likewise, while a nested array is shown in this example, different staggered or aligned geometries may also be used, in some examples, in some respects, with reduced complexity, as further described below.

Furthermore, while this particular example encompasses the definition of linearly defined tile region boundaries, other boundary types may also be considered provided they are amenable to the definition of one or more conditional statements, as illustrated below, that can be used to output a corresponding set of binary or Boolean values that distinctly identify a location of a given point within one or another of these regions, for instance, without invoking, or by limiting, processing demands common to branching or looping decision logics/trees/statements/etc.

Figure 17B:
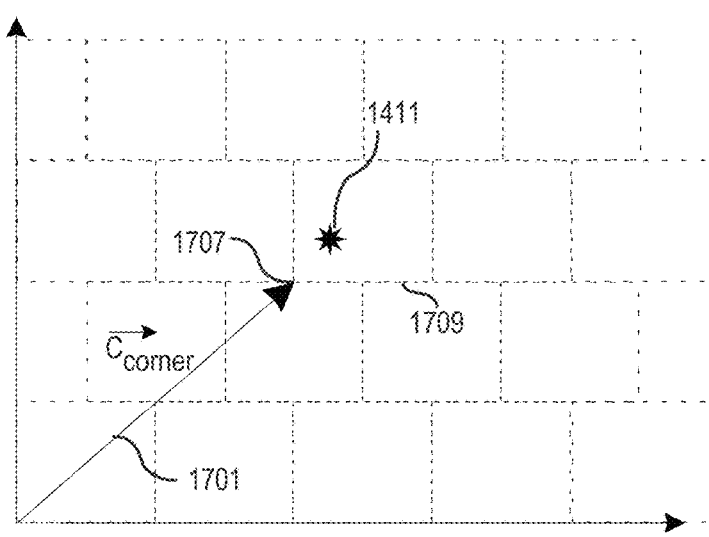

Following with hexagonal example, to locate the associated hexagon tile center 1615 closest to the intersection point 1411, in step 1517, the method first computes the 2D position of the bottom left corner 1707 of the associated (normalized) rectangular tile element 1709 containing intersection point 1411, as shown in FIG. 17B, which can be calculated without using any branching statements by the following two equations (here in normalized coordinates wherein each rectangle has a height and width of one unit):

$$\vec{t} = (\text{floor}(uv_y), 0)$$

$$\vec{C}_{corner} = (\vec{uv} + \vec{t}) - \vec{t}$$

where $\vec{uv}$ is the position vector of intersection point 1411 in the common frame of reference of the hexagonal and staggered rectangular tile arrays, and the floor( ) function returns the greatest integer less than or equal to each of the xy coordinates of $\vec{uv}$.

Figure 18A:
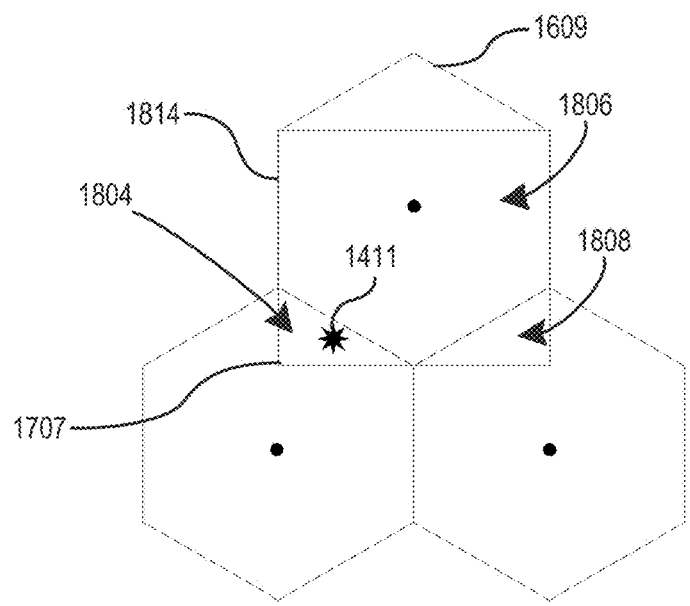
FIGS. 18A to 18C are schematic diagrams illustrating the associated regions of neighboring hexagonal tiles within a single rectangular tile, in accordance with one embodiment.
Figure 18B:
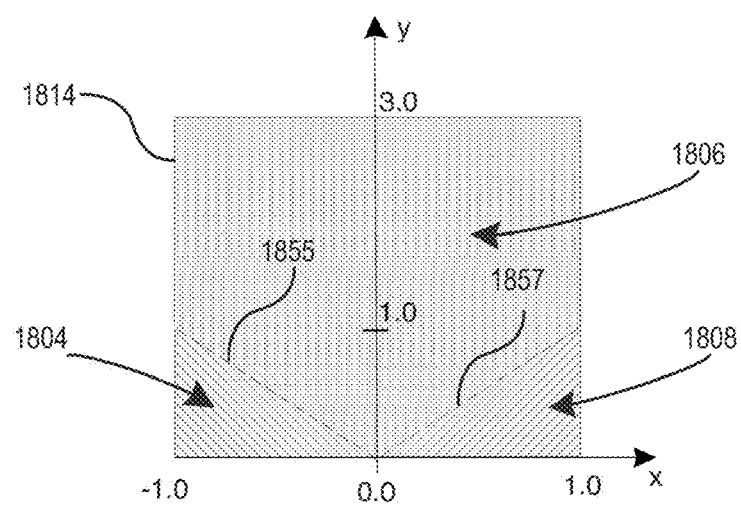
Figure 18C:
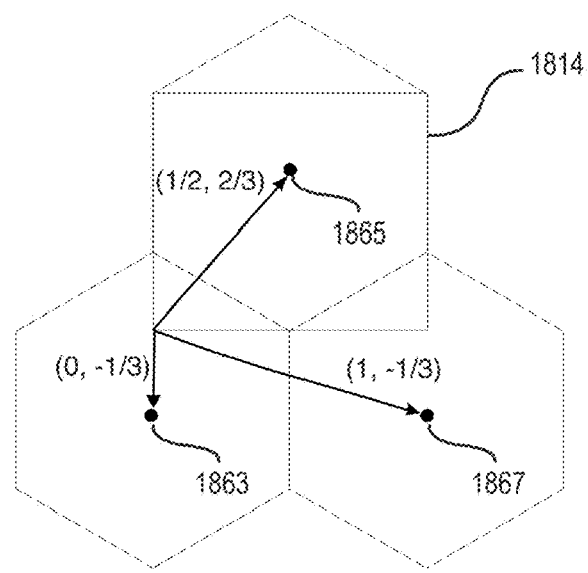

Once the position of lower left corner 1707, indicated by vector $\vec{C}_{corner}$ 1701, of the associated rectangular element 1814 containing the intersection point 1411 is known, three regions 1804, 1806 and 1807 within this rectangular element 1814 may be distinguished, as shown in FIGS. 18A to 18C. Each region is associated with a different hexagonal tile, as shown in FIG. 18A, namely, each region is delineated by the linear boundaries of adjacent underlying hexagonal tiles to define one region predominantly associated with a main hexagonal tile, and two opposed triangular tiles defined by adjacent hexagonal tiles on either side of this main tile. As will be appreciated by the skilled artisan, different hexagonal or nestled tile geometries will result in the delineation of different rectangular tile region shapes, as will different boundary profiles (straight vs. curved) will result in the definition of different boundary value statements, defined further below.

Continuing with the illustrated example, in step 1519, the coordinates within associated rectangular tile 1814 are again rescaled, as shown on the axis of FIG. 18B, so that the intersection point's location, within the associated rectangular tile, is now represented in the rescaled coordinates by a vector $\vec{d}$ where each of its x and y coordinates are given by:

$$d_x = 2*(uv_x - C_{corner_x}) - 1$$
$$d_y = 3*(uv_y - C_{corner_y})$$

Thus, the possible x and y values of the position of intersection point 1411 within associated rectangular tile 1814 are now contained within $-1<x<1$ and $0<y<3$. This will make the next step easier to compute.

To efficiently find the region encompassing a given intersection point in these rescaled coordinates, the fact that, within the rectangular element 1814, each region is separated by a diagonal line is used. For example, this is illustrated in FIG. 18B, wherein the lower left region 1804 is separated from the middle "inverted house" region 1806 and lower right region 1808 by a downward diagonal line 1855, which in the rescaled coordinates of FIG. 18B, follows the simple equation y=−x. Thus, all points where x<−y are located in the lower left region. Similarly, the lower right region 1808 is separated from the other two regions by a diagonal line 1857 described by the equation y<x. Therefore, in step 1521, the associated region containing the intersection point is evaluated by using these two simple conditional statements. The resulting set of two Boolean values will thus be specific to the region where the intersection point is located. For example, the checks (caseL=x<y, caseR=y<x) will result in the values (caseL=true, caseR=false), (caseL=false, caseR=true) and (caseL=false, caseR=false) for intersection points located in the lower left region 1804, lower right region 1808 and middle region 1806, respectively. One may then convert these Boolean values to floating points values, wherein usually in most programming languages true/false Boolean values are converted into 1.0/0.0 floating point values. Thus, one obtains the set (caseL, caseR) of values of (1.0, 0.0), (0.0, 1.0) or (0.0, 0.0) for each of the described regions above.

To finally obtain the relative coordinates of the hexagonal center associated with the identified region, in step 1523, the set of converted Boolean values may be used as an input to a single floating point vectorial function operable to map each set of these values to a set of xy coordinates of the associated element center. For example, in the described embodiment and as shown in FIG. 18C, one obtains the relative position vectors of each hexagonal center $\vec{r}$ with the vectorial function:

$$\vec{r} = (r_x, r_y) = \left(0.5 + 0.5*(caseR - caseL), \frac{2}{3} - (caseR - caseL)\right)$$

thus, the inputs of (1.0, 0.0), (0.0, 1.0) or (0.0, 0.0) map to the positions (0.0, −1/3), (0.5, 2/3), and (1.0, −1/3), respectively, which corresponds to the shown hexagonal centers 1863, 1865 and 1867 shown in FIG. 18C, respectively, in the rescaled coordinates.

Now back to FIG. 15, we may proceed with the final step 1525 to translate the relative coordinates obtained above to absolute 3D coordinates with respect to the display or similar (i.e. in mm). First, the coordinates of the hexagonal tile center and the coordinates of the bottom left corner are added to get the position of the hexagonal tile center in the optical layer's frame of reference. As needed, the process may then scale back the values into absolute units (i.e. mm) and rotate the coordinates back to the original frame of reference with respect to the display to obtain the 3D positions (in mm) of the optical layer element's center with respect to the display's frame of reference, which is then fed into step 1116.

The skilled artisan will note that modifications to the above-described method may also be used. For example, the staggered grid shown in FIG. 17A may be translated higher by a value of ⅓ (in normalized units) so that within each rectangle the diagonals separating each region are located on the upper left and right corners instead. The same general principles described above still applies in this case, and the skilled technician will understand the minimal changes to the equations given above will be needed to proceed in such a fashion. Furthermore, as noted above, different LFSL element geometries can result in the delineation of different (normalized) rectangular tile regions, and thus, the formation of corresponding conditional boundary statements and resulting binary/Boolean region-identifying and center-locating coordinate systems/functions.

In yet other embodiments, wherein a rectangular and/or square microlens array is used instead of a nestled (hexagonal) array, a slightly different method may be used to identify the associated LFSL element (microlens) center (step 1114). Herein, the microlens array is represented by an array of rectangular and/or square tiles. The method, as previously described, goes through step 1515, where the x and y coordinates are rescaled (normalized) with respect to a microlens x and y dimension (henceforth giving each rectangular and/or square tile a width and height of 1 unit). However, at step 1517, the floor( ) function is used directly on each x and y coordinates of $\vec{uv}$ (the position vector of intersection point 1411) to find the coordinates of the bottom left corner associated with the corresponding square/rectangular tile. Therefrom, the relative coordinates of the tile center from the bottom left corner are added directly to obtain the final scaled position vector:

$$\vec{r} = (r_x, r_y) = (floor(uv_x) + 0.5, floor(uv_y) + 0.5)$$

Once this vector is known, the method goes directly to step 1525 where the coordinates are scaled back into absolute units (i.e. mm) and rotated back to the original frame of reference with respect to the display to obtain the 3D positions (in mm) of the optical layer element's center with respect to the display's frame of reference, which is then fed into step 1116.

The light field rendering methods described above (from FIGS. 11 to 20D) may also be applied, in some embodiments, at a subpixel level in order to achieve an improved light field image resolution. Indeed, a single pixel on a color subpixelated display is typically made of several color primaries, typically three colored elements-ordered (on various displays) either as blue, green and red (BGR) or as red, green and blue (RGB). Some displays have more than three primaries such as the combination of red, green, blue and yellow (RGBY) or red, green, blue and white (RGBW), or even red, green, blue, yellow and cyan (RGBYC). Subpixel rendering operates by using the subpixels as approximately equal brightness pixels perceived by the luminance channel. This allows the subpixels to serve as sampled image reconstruction points as opposed to using the combined subpixels as part of a "true" pixel. For the light field rendering methods as described above, this means that the center position of a given pixel (e.g. pixel 1401 in FIG. 14) is replaced by the center positions of each of its subpixel elements. Therefore, the number of color samples to be extracted is multiplied by the number of subpixels per pixel in the digital display. The methods may then follow the same steps as described above and extract the associated image portions of each subpixel individually (sequentially or in parallel).

Figure 21A:
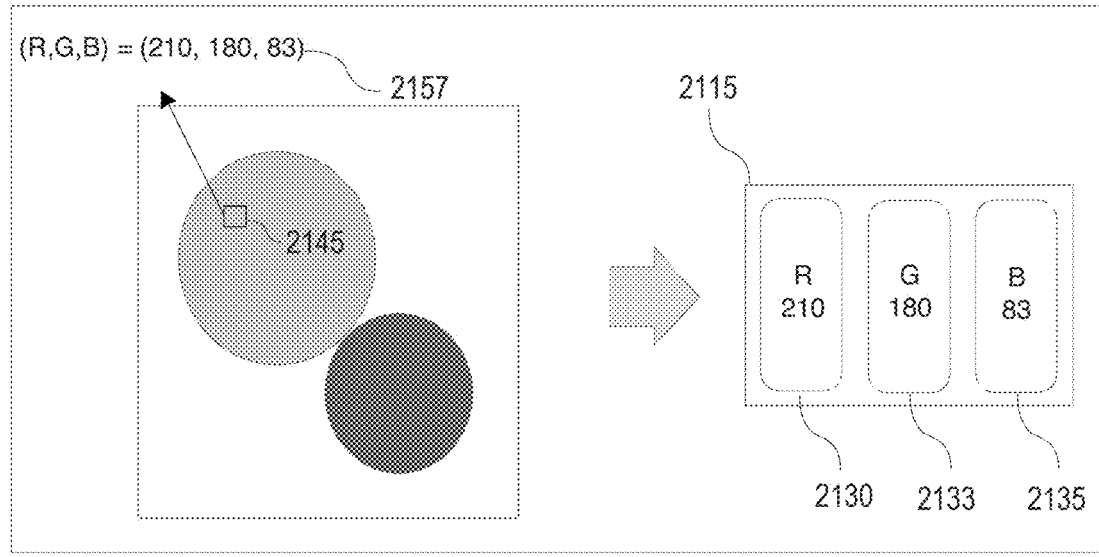
FIGS. 21A and 21B are schematic diagrams illustrating pixel and subpixel rendering, respectively, in accordance with some embodiments.
Figure 21B:
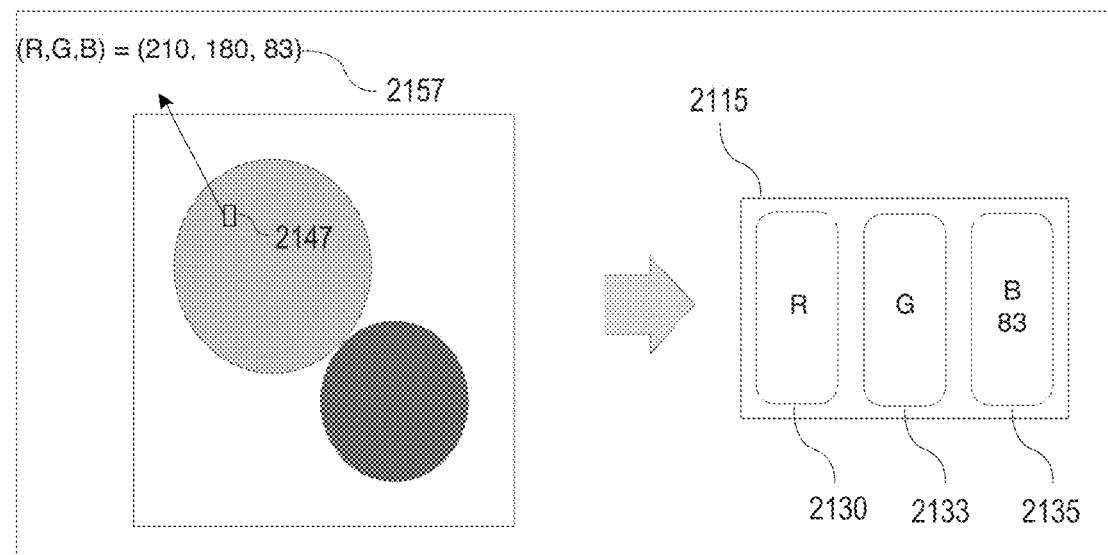

In FIG. 21A, an exemplary pixel 2115 is comprised of three RGB subpixels (2130 for red, 2133 for green and 2135 for blue). Other embodiments may deviate from this color partitioning, without limitation. When rendering per pixel, as described in FIG. 11 or in FIG. 19, the image portion 2145 associated with said pixel 2115 is sampled to extract the luminance value of each RGB color channels 2157, which are then all rendered by the pixel at the same time. In the case of subpixel rendering, as illustrated in FIG. 21B, the methods find the image portion 2147 associated with blue subpixel 2135. Therefore, only the subpixel channel intensity value of RGB color channels 2157 corresponding to the target subpixel 2135 is used when rendering (herein the blue subpixel color value, the other two values are discarded). In doing so, a higher adjusted image resolution may be achieved for instance, by adjusting adjusted image pixel colours on a subpixel basis, and also optionally discarding or reducing an impact of subpixels deemed not to intersect or to only marginally intersect with the user's pupil.

To further illustrate embodiments making use of subpixel rendering, with reference to FIGS. 22A and 22B, a (LCD) pixel array 2200 is schematically illustrated to be composed of an array of display pixels 2202 each comprising red (R) 2204, green (G) 2206, and blue (B) 2208 subpixels. As with the examples provided above, to produce a light field display, a light field shaping layer, such as a microlens array, is to be aligned to overlay these pixels such that a corresponding subset of these pixels can be used to predictably produce respective light field rays to be computed and adjusted in providing a corrected image. To do so, the light field ray ultimately produced by each pixel can be calculated knowing a location of the pixel (e.g. x,y coordinate on the screen), a location of a corresponding light field element through which light emanating from the pixel will travel to reach the user's eye(s), and optical characteristics of that light field element, for example. Based on those calculations, the image correction algorithm will compute which pixels to light and how, and output subpixel lighting parameters (e.g. R, G and B values) accordingly. As noted above, to reduce computation load, only those pixels producing rays that will interface with the user's eyes or pupils may be considered, for instance, using a complementary eye tracking engine and hardware, though other embodiments may nonetheless process all pixels to provide greater buffer zones and/or a better user experience.

In the example shown in FIG. 22A, an angular edge 2209 is being rendered that crosses the surfaces of affected pixels 2210, 2212, 2214 and 2216. Using standard pixel rendering, each affected pixel is either turned on or off, which to some extent dictates a relative smoothness of the angular edge 2209.

In the example shown in FIG. 22B, subpixel rendering is instead favoured, whereby the red subpixel in pixel 2210, the red and green subpixels in pixel 2214 and the red subpixel in pixel 2216 are deliberately set to zero (0) to produce a smoother representation of the angular edge 2209 at the expense of colour trueness along that edge, which will not be perceptible to the human eye given the scale at which these modifications are being applied. Accordingly, image correction can benefit from greater subpixel control while delivering sharper images.

In order to implement subpixel rendering in the context of light field image correction, in some embodiments, ray tracing calculations must be executed in respect of each subpixel, as opposed to in respect of each pixel as a whole, based on a location (x,y coordinates on the screen) of each subpixel. Beyond providing for greater rendering accuracy and sharpness, subpixel control and ray tracing computations may accommodate different subpixel configurations, for example, where subpixel mixing or overlap is invoked to increase a perceived resolution of a high resolution screen and/or where non-uniform subpixel arrangements are provided or relied upon in different digital display technologies.

In some embodiments, however, in order to avoid or reduce a computation load increase imparted by the distinct consideration of each subpixel, some computation efficiencies may be leveraged by taking into account the regular subpixel distribution from pixel to pixel, or in the context of subpixel sharing and/or overlap, for certain pixel groups, lines, columns, etc. With reference to FIG. 23, a given pixel 2300, much as those illustrated in FIGS. 22A and 22B, is shown to include horizontally distributed red (R) 2304, green (G) 2306, and blue (B) 2308 subpixels. Using standard pixel rendering and ray tracing, light emanating from this pixel can more or less be considered to emanate from a point located at the geometric center 2310 of the pixel 2300. To implement subpixel rendering, ray tracing could otherwise be calculated in triplicate by specifically addressing the geometric location of each subpixel. Knowing the distribution of subpixels within each pixel, however, calculations can be simplified by maintaining pixel-centered computations and applying appropriate offsets given known geometric subpixel offsets (i.e. negative horizontal offset 2314 for the red subpixel 2304, a zero offset for the green 2306 and a positive horizontal offset 2318 for the blue subpixel 2308). In doing so, light field image correction can still benefit from subpixel processing without significantly increased computation load.

While this example contemplates a linear (horizontal) subpixel distribution, other 2D distributions may also be considered without departing from the general scope and nature of the present disclosure. For example, for a given digital display screen and pixel and subpixel distribution, different subpixel mappings can be determined to define respective pixel subcoordinate systems that, when applied to standard pixel-centric ray tracing and image correction algorithms, can allow for subpixel processing and increase image correction resolution and sharpness without undue processing load increases.

In some embodiments, additional efficiencies may be leveraged on the GPU by storing the image data, for example image 1306, in the GPU's texture memory. Texture memory is cached on chip and in some situations is operable to provide higher effective bandwidth by reducing memory requests to off-chip DRAM. Specifically, texture caches are designed for graphics applications where memory access patterns exhibit a great deal of spatial locality, which is the case of the steps 1110-1126 of method 1100. For example, in method 1100, image 1306 may be stored inside the texture memory of the GPU, which then greatly improves the retrieval speed during step 1126 where the color channel associated with the portion of image 1306 at intersection point 1423 is determined.

With reference to FIGS. 24 to 26D, and in accordance with one embodiment, an exemplary computationally implemented ray-tracing method for rendering multiple images or image portions on multiple adjusted distinct image planes simultaneously via an array of light field shaping elements, or light field shaping layer (LFSL) thereof, will now be described. The previous above-described embodiments were directed to correcting a single image by directly or indirectly modifying the location of the virtual image plane. In contrast, the below-described embodiments are directed to a light field display which is generally operable to display multiple image planes at different locations/depths simultaneously. Unlike known stereoscopic effects, the methods as herein described may be implemented to generate varying depth perceptions within a same eye, that is, allowing for the monoscopic viewing of an input to exhibit multiple distinct image perception adjustments (i.e. multiple juxtaposed and/or overlapping depths, enhancements or like optical adjustments, compensations, etc.). For example, in some embodiments, distinct image planes may be juxtaposed such that different sides or quadrants of an image, for example, may be perceived at different depths. In such embodiments, a different effective vision correction parameter (e.g. diopter), or depth, may be applied, to each portion or quadrant. While this approach may result in some distortions or artefacts at the edges of the areas or quadrants, depending on the image data to be rendered along these edges, such artefacts may be negligible if at all perceivable. In other embodiments, however, different image portions may be at least partially superimposed such that portions at different depths, when viewed from particular perspectives, may indeed appear to overlap. This enables a user to focus on each plane individually, thus creating a 2.5D effect. Thus, a portion of an image may mask or obscure a portion of another image located behind it depending on the location of the user's pupil (e.g. on an image plane perceived to be located at an increased distance from the display than the one of the first image portion). Other effects may include parallax motion between each image plane when the user moves. The following provides a more detailed description of an embodiment in which overlapping portions may be addressed via an applicable transparency parameter resolved by processing each virtual image portion layer by layer.

Figure 24:
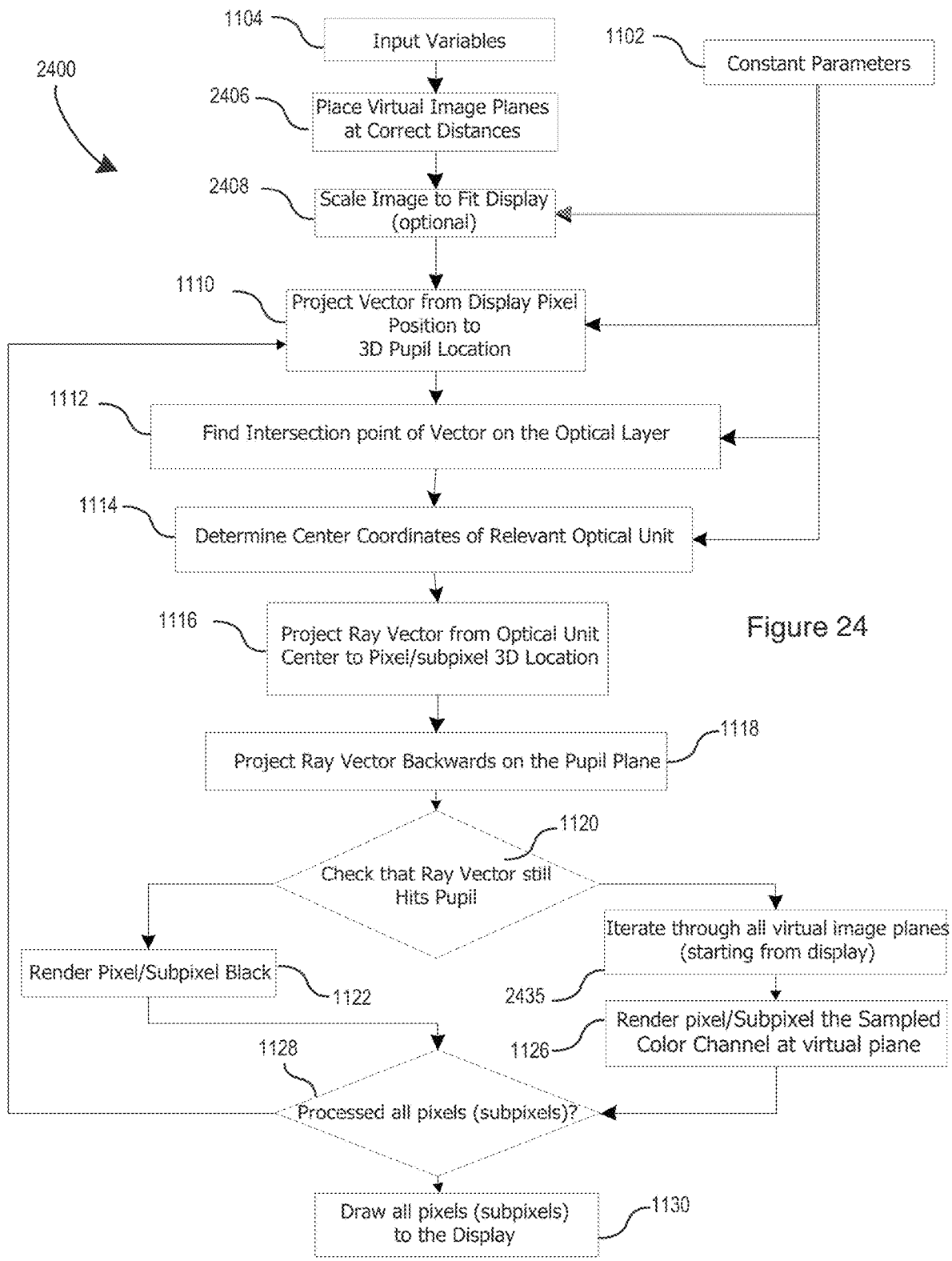
FIG. 24 is a process flow diagram of an illustrative ray-tracing rendering process for rendering a light field originating from multiple distinct virtual image planes, in accordance with one embodiment.

Method 2400 of FIG. 24 substantially mirrors method 1100 of FIG. 11, but generalizes it to include multiple distinct virtual image planes. Thus, new steps 2406, 2408, and 2435 have been added, while steps 1110 to 1122, and 1126 to 1130 are the same as already described above. Meanwhile, when considering a fixed refractor installation, the input of constant parameters 1102 may, in such cases, be fixed and integrally designed within operation of the device/system.

For example, to account for multiple distinct image planes, image data 1306 of input variables 1104 may also include depth information. Thus, any image or image portion may have a respective depth indicator. Thus, at step 2406, a set of multiple virtual image planes may be defined. On these planes, images or image portions may be present. Areas around these images may be defined as transparent or see-through, meaning that a user would be able to view through that virtual image plane and see, for example, images or image portions located behind it. At step 2408, any image or image portion on these virtual image planes may be optionally scaled to fit the display.

As an example, in the previous example of FIGS. 14A-14C, a single virtual image plane 1405, showing two circles, was shown. In contrast, FIGS. 26A and 26B show an example wherein each circle is located on its own image plane (e.g. original virtual plane 1405 with new virtual image plane 2605). The skilled technician will understand that two planes are shown only as an example and that the method described herein applies equally well to any number of virtual planes. The only effect of having more planes is a larger computational load.

Going back to FIG. 24, steps 1110 to 1122 occur similarly to the ones described in FIG. 11. However, step 1124 has been included and expanded upon in Step 2435, which is described in FIG. 25. In step 2435, an iteration is done over the set of virtual image planes to compute which image portion from which virtual image plane is seen by the user. Thus, at step 2505 a virtual image plane is selected, starting from the plane located closest to the user. Then step 1124 proceeds as described previously for that selected virtual plane. At step 2510 the corresponding color channel of the intersection point identified at step 1124 is sampled. Then at step 2515, a check is made to see if the color channel is transparent. If this is not the case, then the sampled color channel is sent to step 1126 of FIG. 24, which was already described and where the color channel is rendered by the pixel/subpixel. An example of this is illustrated in FIGS. 26A and 26B, wherein a user is located so that a ray vector 2625 computed passing through optical element 2616 and pixel/subpixel 2609 intersects virtual image plane 1405 at location 2623. Since this location is non-transparent, this is the color channel that will be assigned to the pixel/subpixel. However, as this example shows, this masks or hides parts of the image located on virtual image plane 2605. Thus, an example of the image perceived by the user is shown in FIG. 26B.

Figure 25:
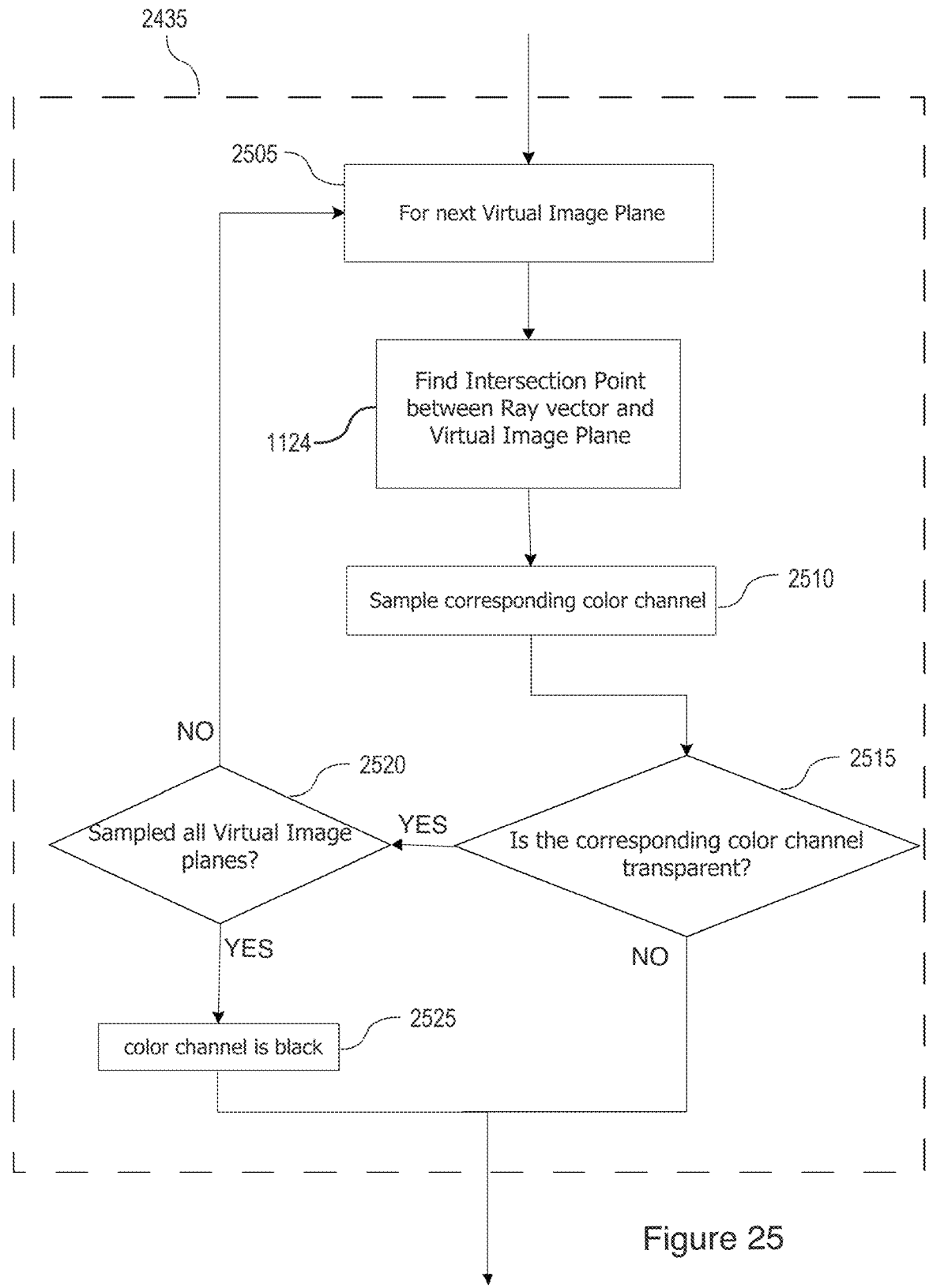
FIG. 25 is a process flow diagram of an exemplary process for iterating over multiple virtual image planes in the ray-tracing rendering process of FIG. 24, in accordance with one embodiment.

Going back to FIG. 25, at step 2515 if the color channel is transparent, then another check is made at step 2520 to see if all virtual image planes have been iterated upon. If this is the case, then that means that no image or image portion is seen by the user and at step 2525, for example, the color channel is set to black (or any other background colour), before proceeding to step 1126. If however at least one more virtual image plane is present, then the method goes back to step 2505 and selects that next virtual image plane and repeats steps 1124, 2510 and 2515. An example of this is illustrated in FIG. 26C, wherein a user is located so that a distinct ray vector 2675 computed passing through optical element 2666 and pixel/subpixel 2659 first intersects at location 2673 of virtual image plane 1405. This location is defined to be transparent, so the method checks for additional virtual image planes (here plane 2605) and computes the intersection point 2693, which is non-transparent, and thus the corresponding color channel is selected. An example of the image perceived by the user is shown in FIG. 26D.

Going back to FIG. 24, once the pixel/subpixel has been assigned the correct color channel at step 1126, the method proceeds as described previously at steps 1128 and 1130.

Figure 27:
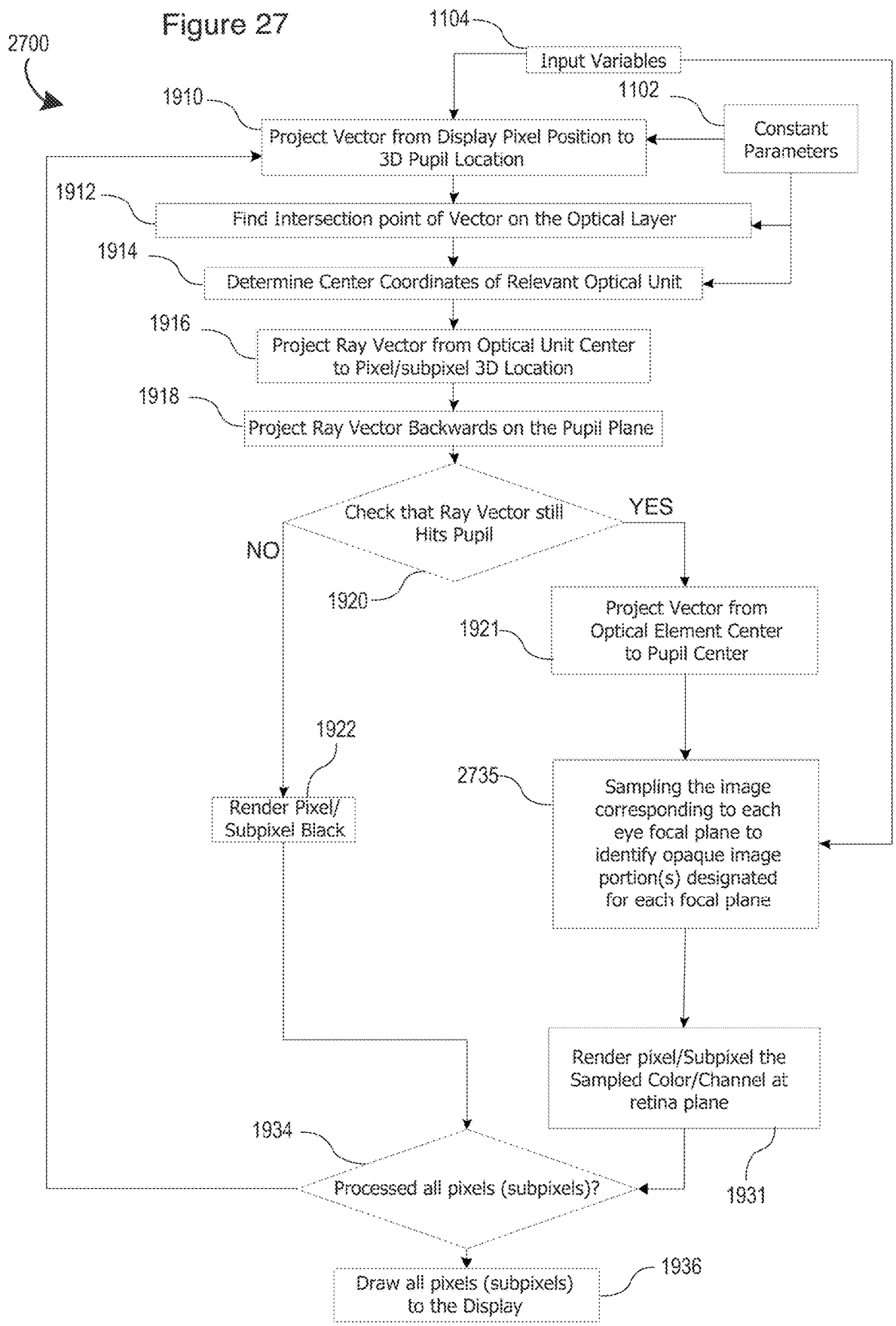
FIG. 27 is a process flow diagram of an illustrative ray-tracing rendering process for rendering a light field originating from multiple distinct virtual image planes, in accordance with one embodiment.
Figure 28:
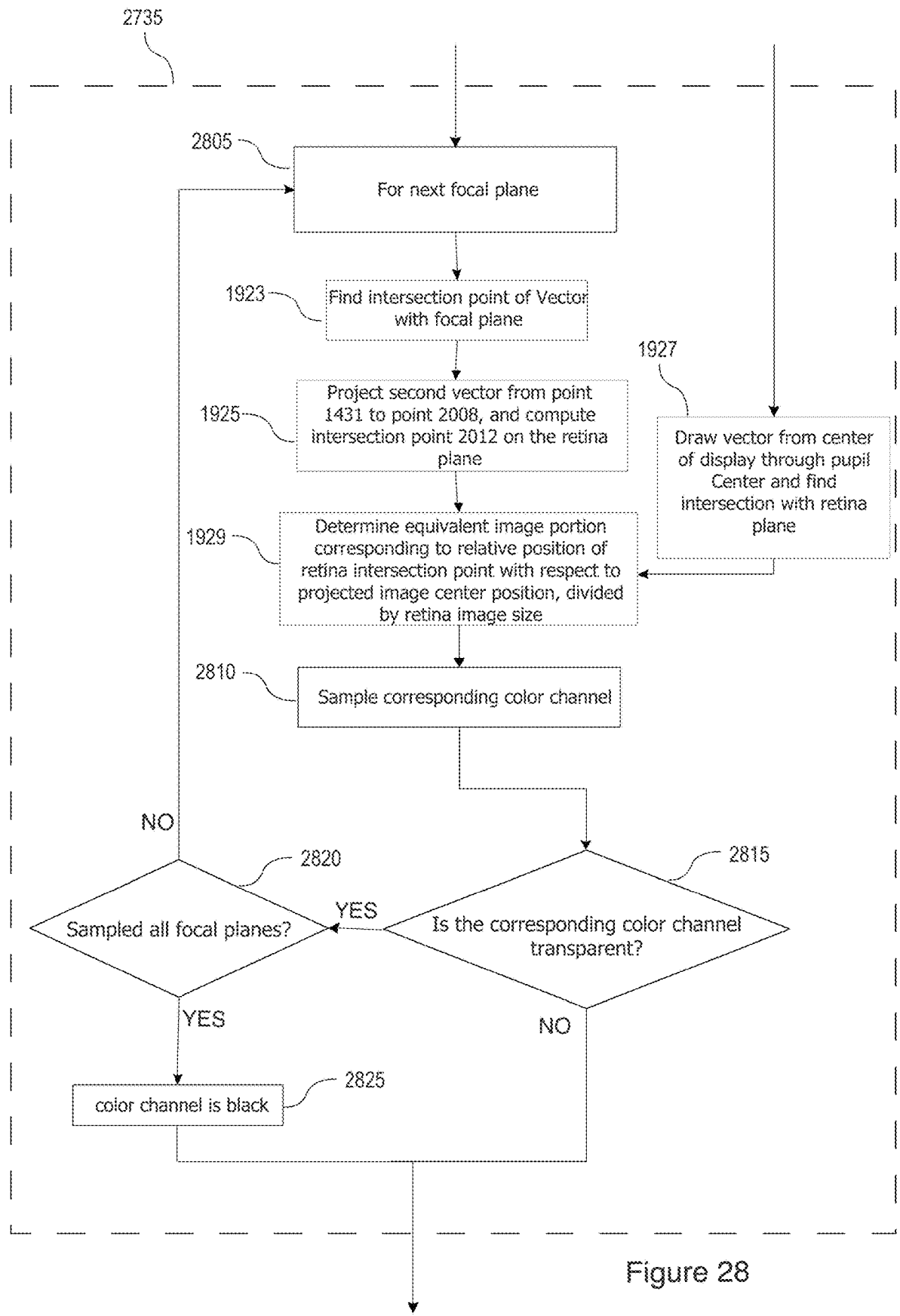
FIG. 28 is a process flow diagram of an exemplary process for iterating over multiple virtual image planes in the ray-tracing rendering process of FIG. 27, in accordance with one embodiment.

Similarly, method 2700 of FIG. 27 substantially mirrors method 1900 of FIG. 19 but also generalizes it to include multiple distinct eye focal planes, including infinity, as explained above. Thus, in method 2700, steps 1910 to 1921 and 1931 to 1936 are the same as described for method 1900. The difference comes from new step 2735 which includes and expands upon steps 1921 to 1929, as shown in FIG. 28. There, we see that the method iterates over all designated image planes, starting from the plane corresponding to an image located closest to the user. Thus, a new eye focal plane is selected at step 2805, which is used for steps 1923 to 1929 already described above. Once the corresponding image portion is located at step 1929, at step 2810, the corresponding pixel/subpixel color channel is sampled. Then at step 2815, if the color channel is non-transparent, then the method goes back to step 1931 of FIG. 27, wherein the pixel/subpixel is assigned that color channel. However, if the image portion is transparent, then the method iterates to the next designated image plane. Before this is done, the method checks at step 2820 if all the eye focal planes have been iterated upon. If this is the case, then no image portion will be selected and at step 2825 the color channel is set to black, for example, before exiting to step 1931. If other eye focal planes are still available, then the method goes back to step 2805 to select the next plane and the method iterates once more.

Figure 29A:
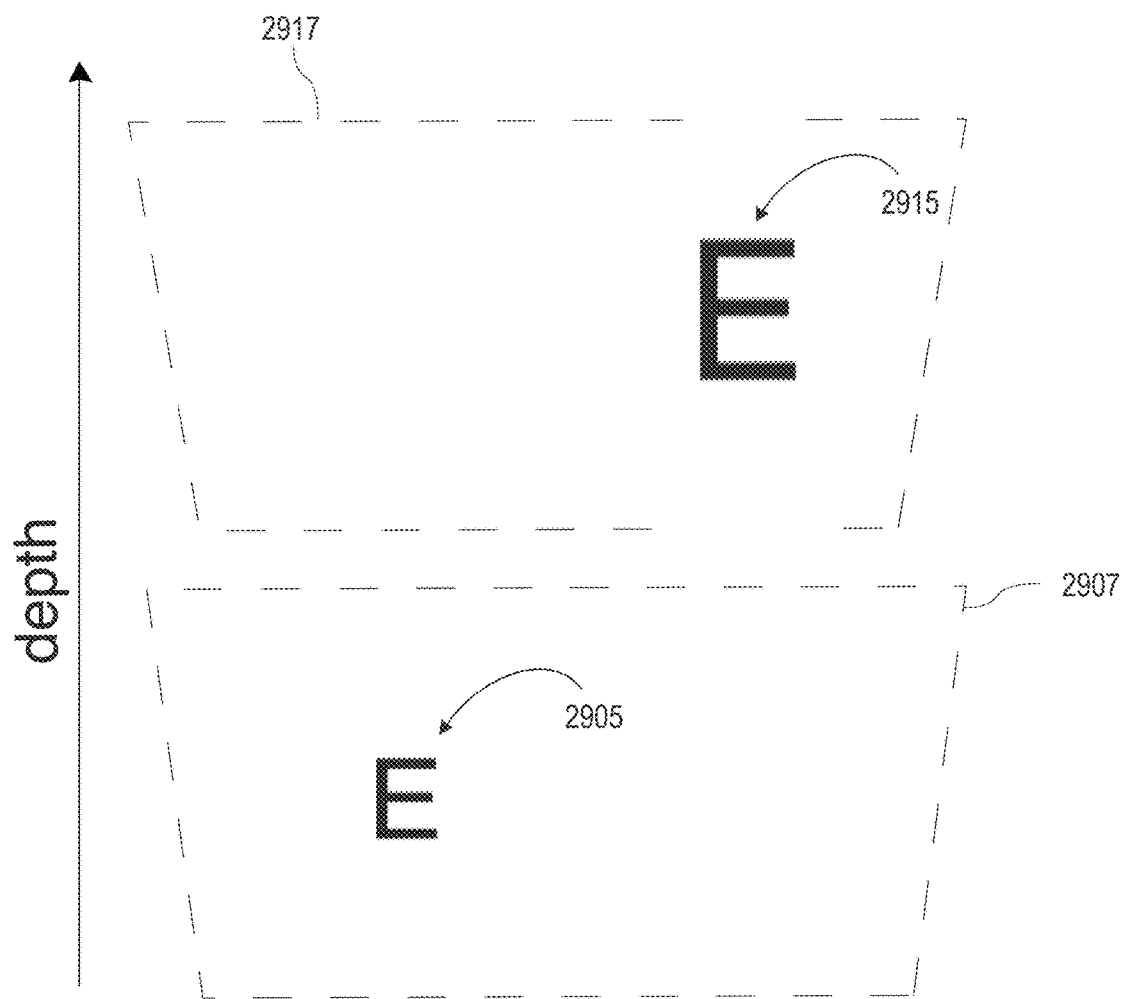
FIGS. 29A and 29B are schematic diagrams illustrating an example of a subjective visual acuity test using the ray-tracing rendering process of FIG. 25 or FIG. 27, in accordance with one embodiment.
Figure 29B:
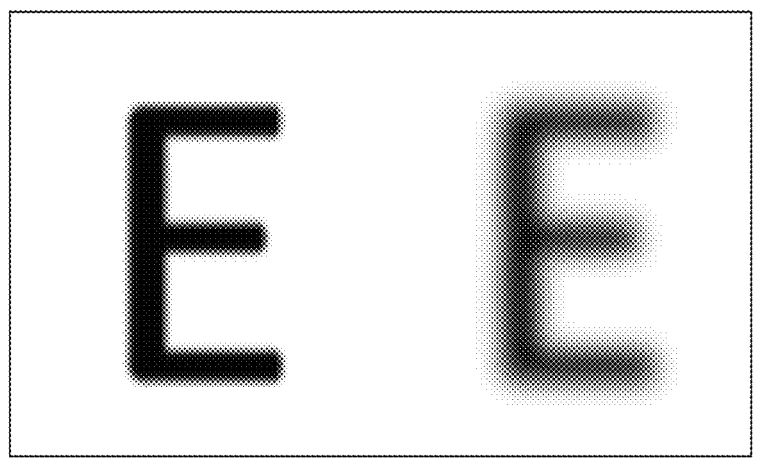

In some embodiments, methods 2400 or 2700 may be used to implement a phoropter/refractor device to do subjective visual acuity evaluations. For example, as illustrated in FIGS. 29A and 29B, different optotypes (e.g. letters, symbols, etc.) may be displayed simultaneously but at different perceived depths, to simulate the effect of adding a refractive optical component (e.g. change in focus/optical power). In FIG. 29A, two images of the same optotype (e.g. letter E) are displayed, each on their own designated image plane (e.g. here illustrated as virtual image planes as an example only). In this example, image 2905 is located on designated image plane 2907 while image 2915 is located on designated image plane 2917, which is located further away. In FIG. 29B, we see an example of the perception of both images as perceived by a user with reduced visual acuity (e.g. myopia), for example, wherein the image closest to the user is seen to be clearer. Thus, a user could be presented with multiple images (e.g. 2 side-by-side, 4, 6 or 9 in a square array, etc.) and indicate which image is clearer and/or most comfortable to view. An eye prescription may then be derived from this information. Moreover, in general, both spherical and cylindrical power may be induced by the light field display.

Accordingly, it can be observed that the ray-tracing methods 2400 and 2700 noted above, and related light field display solutions, can be equally applied to image perception adjustment solutions for visual media consumption, as they can for subjective vision testing solutions, or other technologically related fields of endeavour. As alluded to above, the light field display and rendering/ray-tracing methods discussed above may all be used to implement, according to various embodiments, a subjective vision testing device or system such as a phoropter or refractor. Indeed, a light field display may replace, at least in part, the various refractive optical components usually present in such a device. Thus, the vision correction light field ray tracing methods 1100, 1900, 2400, or 2700 discussed above may equally be applied to render optotypes at different dioptric power or refractive correction by generating vision correction for hyperopia (far-sightedness) and myopia (nearsightedness), as was described above in the general case of a vision correction display. Light field systems and methods described herein, according to some embodiments, may be applied to create the same capabilities as a traditional instrument and to open a spectrum of new features, all while improving upon many other operating aspects of the device. For example, the digital nature of the light field display enables continuous changes in dioptric power compared to the discrete change caused by switching or changing a lens or similar; displaying two or more different dioptric corrections seamlessly at the same time; and, in some embodiments, the possibility of measuring higher-order aberrations and/or to simulate them for different purposes such as, deciding for free-form lenses, cataract surgery operation protocols, IOL choice, etc. Such exemplary subjective vision testing and accommodation systems were previously descried in Applicant's U.S. Pat. No. 10,761,604 issued Sep. 1, 2020, the entire disclosure of which is incorporated herein by reference.

With reference to FIGS. 30, and 31A to 31C, and in accordance with different illustrative, but non-limiting embodiments, an exemplary subjective vision testing system, generally referred to using the numeral 3000, will now be described. At the heart of this system is a light field vision testing device such as a light field refractor or phoropter 3001. Generally, the light field phoropter 3001 is a device comprising, at least in part, a light field display 3003 and which is operable to display or generate one or more optotypes to a patient having his/her vision acuity (e.g. refractive error) tested. In some embodiments, the light field phoropter may comprise an eye tracker 3009 (such as a near-IR camera or other as discussed above) that may be used to determine the pupil center position in real-time or near real-time, for accurately locating the patient's pupil, as explained above with regard to the ray-tracing methods 1100, 1900, 2400, or 2700. Indeed, FIG. 32 shows a plot of the angular resolution (in arcminutes) of an exemplary light field display comprising a 1500 ppi digital pixel display as a function of the dioptric power of the light field image (in diopters). We clearly see that, in this particular example, the light field display is able to generate displacements (line 3205) in diopters that have higher resolution corresponding to 20/20 vision (line 3207) or better (e.g. 20/15—line 3209) and close to (20/10—line 3211)), here within a dioptric power range of 2 to 2.5 diopters. Thus, the light field displays and ray-tracing methods described above, according to different embodiments, may be used to replace, at least in part, traditional optical components. In some embodiments, a head-rest, eyepiece or similar (not shown) may be used to keep the patient's head still and in the same location, thus in such examples, foregoing the general utility of a pupil tracker or similar techniques by substantially fixing a pupil location relative to this headrest. In some embodiments, phoropter 3001 may comprise a network interface 3023 for communicating via network to a remote database or server 3059.

Figure 31A:
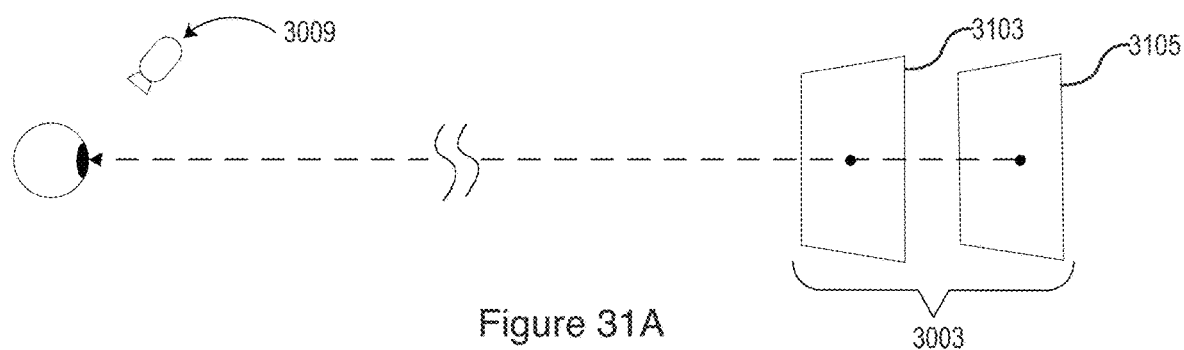
FIGS. 31A to 31C are schematic diagrams of exemplary light field refractors/phoropters, in accordance with different embodiments.
Figure 32:
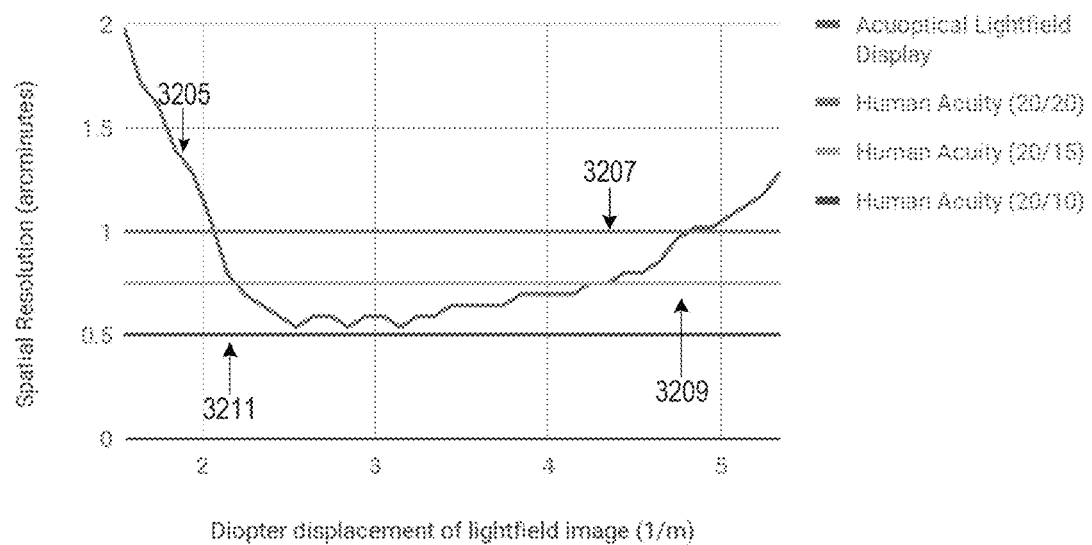
FIG. 32 is a plot of the angular resolution of an exemplary light field display as a function of the dioptric power generated, in accordance with one embodiment.

For example, in one embodiment and as illustrated in FIG. 31A, the light field phoropter 3001 may comprise light field display 3003 (herein comprising a MLA 3103 and a digital pixel display 3105) located relatively far away (e.g. one or more meters) from the patient' eye currently being diagnosed. Note that the pointed line is used to schematically illustrate the direction of the light rays emitted by the display 3105. Also illustrated is the eye-tracker 3009, which may be provided as a physically separate element, for example, installed in at a given location in a room or similar. In some embodiments, the noted eye/pupil tracker may include the projection of IR markers/patterns to help align the patient's eye with the light field display. In some embodiments, a tolerance window (e.g. "eye box") may be considered to limit the need to refresh the ray-tracing iteration. An exemplary value of the size of the eye box, in some embodiments, is around 6 mm, though smaller (e.g. 4 mm) or larger eye boxes may alternatively be set to impact image quality, stability or like operational parameters.

Going back to FIG. 30, light field phoropter 3001 may also comprise, according to different embodiments and as will be further discussed below, one or more refractive optical components 3007, a processing unit 3021, a data storage unit or internal memory 3013, a network interface 3023, one or more cameras 3017 and a power module 3023.

In some embodiments, power module 3023 may comprise, for example, a rechargeable Li-ion battery or similar. In some embodiments, it may comprise an additional external power source, such as, for example, a USB-C external power supply. It may also comprise a visual indicator (screen or display) for communicating the device's power status, for example whether the device is on/off or recharging.

In some embodiments, internal memory 3013 may be any form of electronic storage, including a disk drive, optical drive, read-only memory, random-access memory, or flash memory, to name a few examples. In some embodiments, a library of chart patterns (Snellen charts, prescribed optotypes, forms, patterns, or other) may be located in internal memory 3013 and/or retrievable from remote server 3059.

Figure 33A:
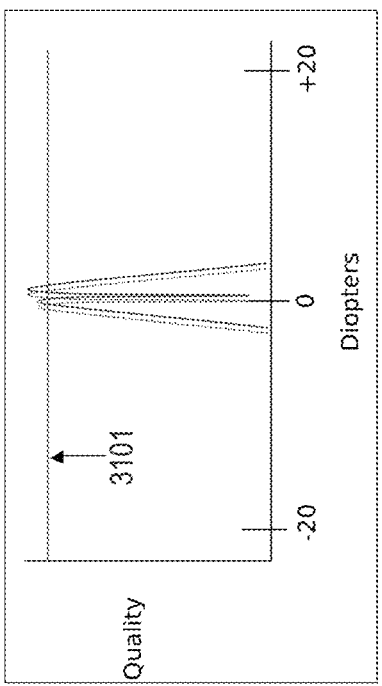
FIGS. 33A to 33D are schematic plots of the image quality generated by a light field refractor/phoropter as a function of the dioptric power generated by using in combination with the light field display (A) no refractive component, (B) one refractive component, (C) and (D) a multiplicity of refractive components.
Figure 33B:
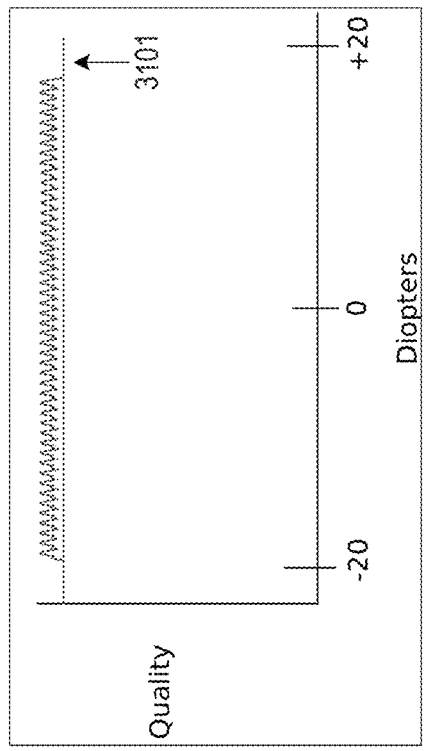

In some embodiments, one or more optical components 3007 can be used in combination with the light field display 3003, for example to shorten the device's dimensions and still offer an acceptable range in dioptric power. The general principle is schematically illustrated in the plots of FIGS. 33A to 33D. In these plots, the image quality (e.g. inverse of the angular resolution, higher is better) at which optotypes are small enough to be useful for vision testing in this plot is above horizontal line 3101 which represents typical 20/20 vision. FIG. 33A shows the plot for the light field display only, where we see the characteristic two peaks corresponding to the smallest resolvable point, one of which was plotted in FIG. 32 (here inverted and shown as a peak instead of a basin), and where each region above the line may cover a few diopters of dioptric power, according to some embodiments. While the dioptric range may, in some embodiments, be more limited than needed when relying only on the light field display, it is possible to shift this interval by adding one or more refractive optical components. This is shown in FIG. 33B where the regions above the line 3101 is shifted to the left (negative diopters) by adding a single lens in the optical path.

Figure 33C:
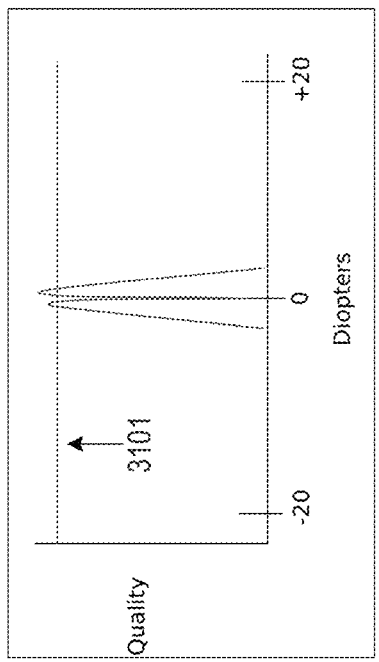
Figure 33D:
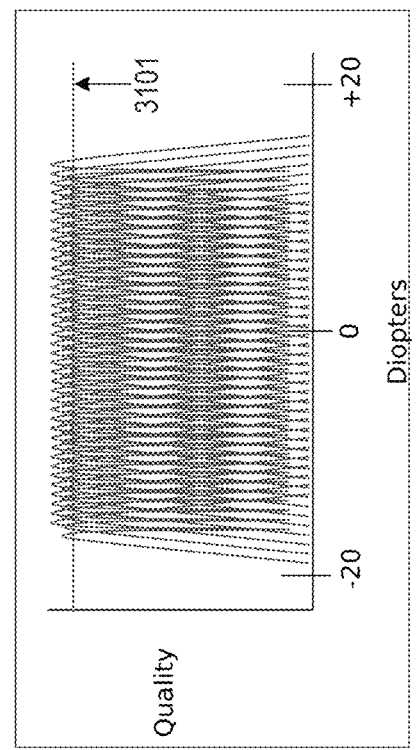

Thus, by using a multiplicity of refractive optical components or by alternating sequentially between different refractive components of increasing or decreasing dioptric power, it is possible to shift the center of the light field diopter range to any required value, as shown in FIG. 33C, and thus the image quality may be kept above line 3101 for any required dioptric power as shown in FIG. 33D. In some embodiments, a range of 30 diopters from +10 to −20 may be covered for example. In the case of one or more reels of lenses, the lens may be switched for a given larger dioptric power increment, and the light field display would be used to provide a finer continuous change to accurately pin-point the required total dioptric power required to compensate for the patient's reduced visual acuity. This would still result in light field phoropter 3001 having a reduced number of refractive optical components compared to the number of components needed in a traditional phoropter, while drastically enhancing the overall fine-tuning ability of the device.

Figure 31B:
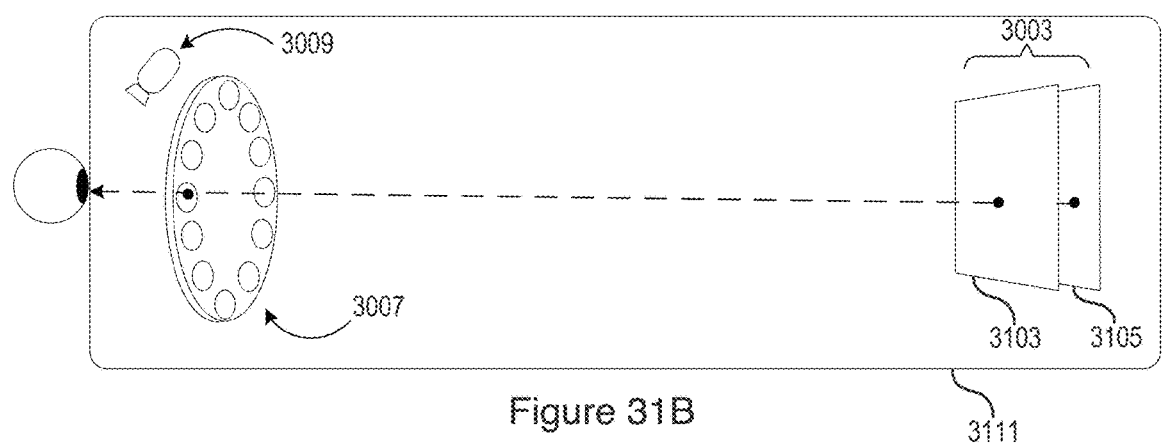

One example, according to one embodiment, of such a light field phoropter 3001 is schematically illustrated in FIG. 31B, wherein the light field display 3003 (herein shown again comprising MLA 3103 and digital pixel display 3105) is combined with a multiplicity of refractive components 3007 (herein illustrate as a reel of lenses as an example only). By changing the refractive component used in combination with the light field display, a larger dioptric range may be covered. This may also provide means to reduce the device's dimension, making it in some embodiments more portable, and encompass all its internal components into a shell, housing or casing 3111. In some embodiments, the light field phoropter may comprise a durable ABS housing and may be shock and harsh-environment resistant. In some embodiments, the light field phoropter 3001 may comprise a telescopic feel for fixed or portable usage; optional mounting brackets, and/or a carrying case. In some embodiments, all components may be internally protected and sealed from the elements.

In some embodiments, the casing may further comprise an eye piece or similar that the patient has to look through, which may limit movement of the patient's eye during diagnostic and/or indirectly provide a pupil location to the light field renderer.

Figure 31C:
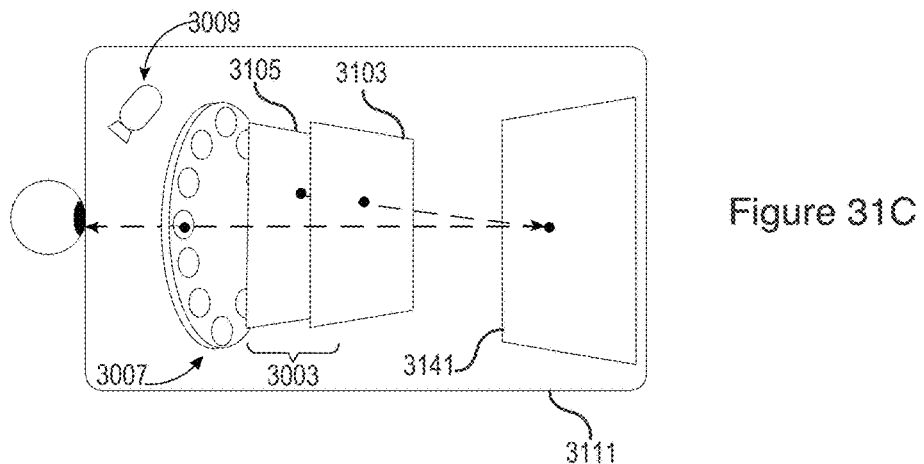

In some embodiments, it may also be possible to further reduce the size of the device by adding, for example, a mirror or any device which may increase the optical path. This is illustrated in FIG. 31C where the length of the device was reduced by adding a mirror 3141. This is shown schematically by the pointed arrow which illustrates the light being emitted from pixel display 3105 travelling through MLA 3103 before being reflected by mirror 3141 back through refractive components 3007 and ultimately hitting the eye.

The skilled technician will understand that different examples of refractive components 3007 may include, without limitation, one or more lenses, sometimes arranged in order of increasing dioptric power in one or more reels of lenses similar to what is typically found in traditional phoropters; an electrically controlled fluid lens; active Fresnel lens; and/or Spatial Light Modulators (SLM). In some embodiments, additional motors and/or actuators may be used to operate refractive components 3007. These may be communicatively linked to processing unit 3021 and power module 3023, and operate seamlessly with light display 3003 to provide the required dioptric power.

Figure 34A:
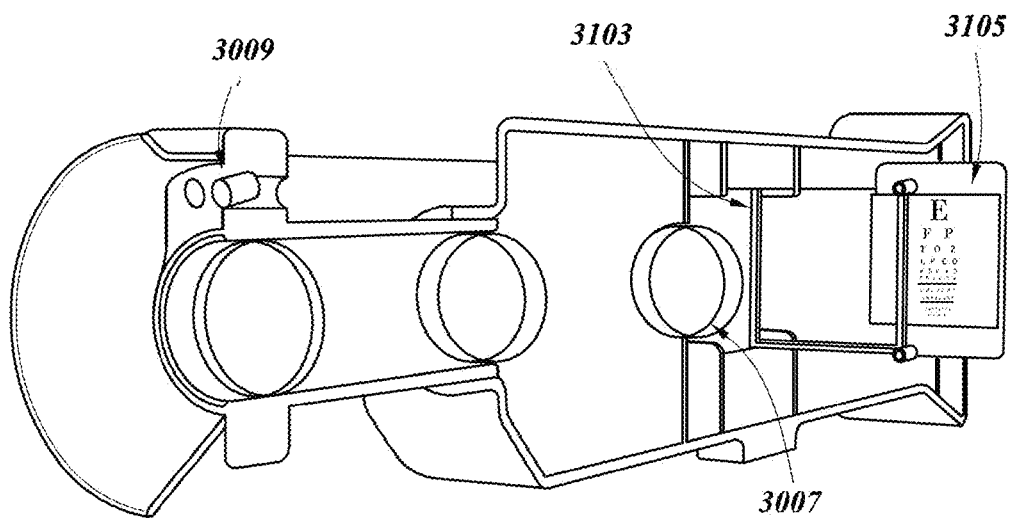
FIGS. 34A and 34B are perspective internal views of exemplary light field refractors/phoropters showing a casing thereof in cross-section, in accordance with one embodiment.
Figure 34B:
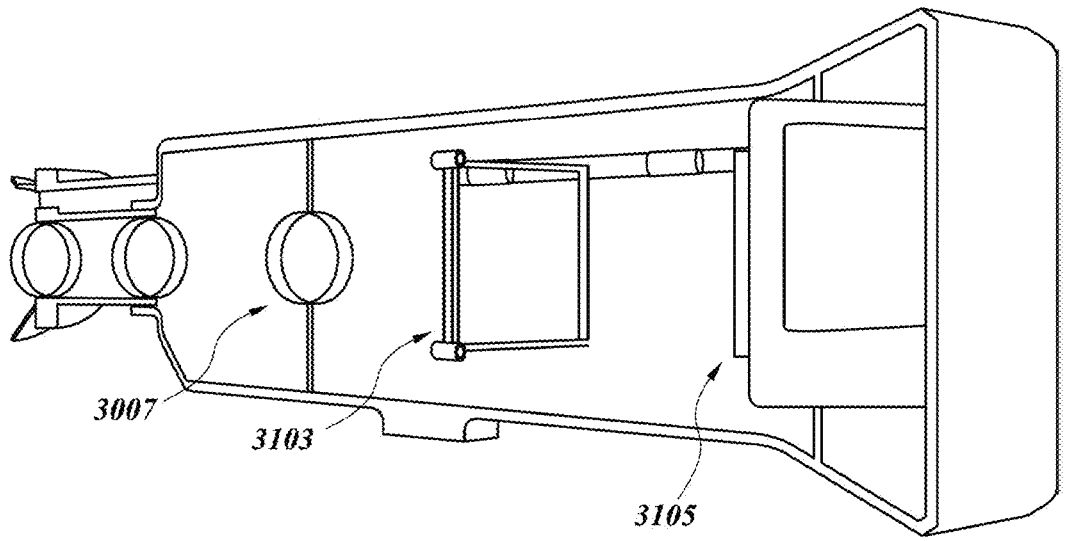

For example, FIGS. 34A and 34B show a perspective view of an exemplary light field phoropter 3001 similar to the one of FIG. 31B, but wherein the refractive component 3007 is an electrically tunable liquid lens. Thus, in this particular embodiment, no mechanical or moving component are used, which may result in the device being more robust. In some embodiments, the electrically tunable lens may have a range of +13 diopters.

In one illustrative embodiment, a 1000 dpi display is used with a MLA having a 65 mm focal distance and 1000 μm pitch with the user's eye located at a distance of about 26 cm. A similar embodiment uses the same MLA and user distance with a 3000 dpi display.

Other displays having resolutions including 750 dpi, 1000 dpi, 1500 dpi and 3000 dpi were also tested or used, as were MLAs with a focal distance and pitch of 65 mm and 1000 µm, 43 mm and 525 µm, 65 mm and 590 µm, 60 mm and 425 µm, 30 mm and 220 µm, and 60 mm and 425 µm, respectively, and user distances of 26 cm, 45 cm or 65 cm.

Figure 30:
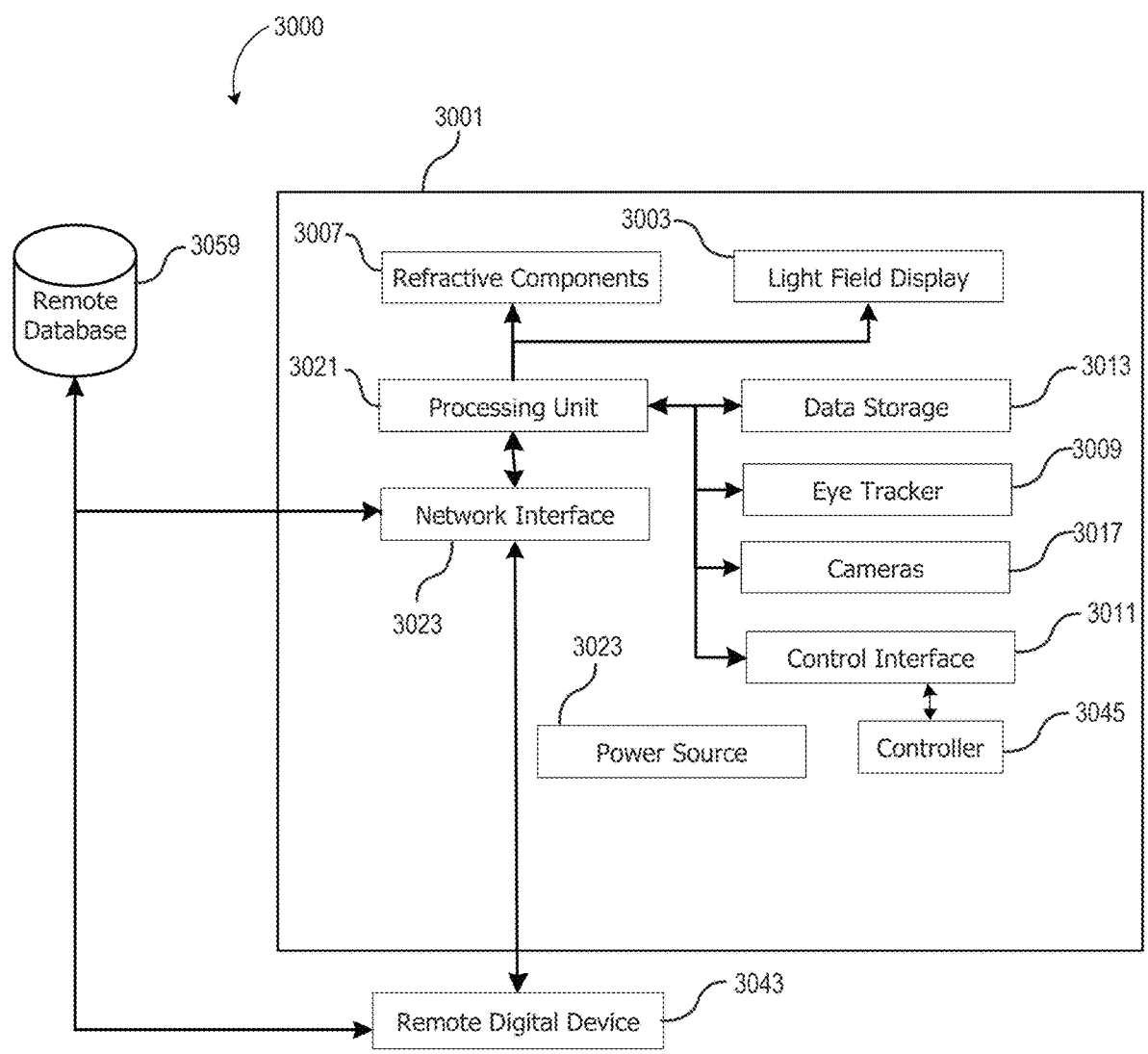
FIG. 30 is a schematic diagram of an exemplary vision testing system, in accordance with one embodiment.

Going back to FIG. 30, in some embodiments, eye-tracker 3009 may be a digital camera, in which case it may be used to further acquire images of the patient's eye to provide further diagnostics, such as pupillary reflexes and responses during testing for example. In other embodiments, one or more additional cameras 3017 may be used to acquire these images instead. In some embodiments, light field phoropter 3001 may comprise built-in stereoscopic tracking cameras.

In some embodiments, feedback and/or control of the vision test being administered may be given via a control interface 3011. In some embodiments, the control interface 3011 may comprise a dedicated handheld controller-like device 3045. This controller 3045 may be connected via a cable or wirelessly, and may be used by the patient directly and/or by an operator like an eye professional. In some embodiments, both the patient and operator may have their own dedicated controller. In some embodiments, the controller may comprise digital buttons, analog thumbstick, dials, touch screens, and/or triggers.

In some embodiments, control interface 3011 may comprise a digital screen or touch screen, either on the phoropter device itself or on an external module. In other embodiments, the control interface may let other remote devices control the light field phoropter via the network interface. For example, remote digital device 3043 may be connected to light field phoropter by a cable (e.g. USB cable, etc.) or wirelessly (e.g. via Bluetooth or similar) and interface with the light field phoropter via a dedicated application, software or website. Such a dedicated application may comprise a graphical user interface (GUI), and may also be communicatively linked to remote database 3059.

In some embodiments, the patient may give feedback verbally and the operator may control the vision test as a function of that verbal feedback. In some embodiments, phoropter 3001 may comprise a microphone to record the patient's verbal communications, either to communicate them to a remote operator via network interface 3023 or to directly interact with the device (e.g. via speech recognition or similar).

In some embodiments, processing unit 3021 may be communicatively connected to data storage 3013, eye tracker 3009, light field display 3003 and refractive components 3007. Processing unit 3021 may be responsible for rendering one or more optotypes via light field display 3003 and, in some embodiments, jointly control refractive components 3007 to achieve a required total dioptric power. It may also be operable to send and receive data to internal memory 3013 or to/from remote database 3059.

In some embodiments, diagnostic data may be automatically transmitted/communicated to remote database 3059 or remote digital device 3043 via network interface 3023 through the use of a wired or wireless network connection. The skilled artisan will understand that different means of connecting electronic devices may be considered herein, such as, but not limited to, Wi-Fi, Bluetooth, NFC, Cellular, 2G, 3G, 4G, 5G or similar. In some embodiments, the connection may be made via a connector cable (e.g. USB including microUSB, USB-C, Lightning connector, etc.). In some embodiments, remote digital device 3043 may be located in a different room, building or city.

Figure 35:
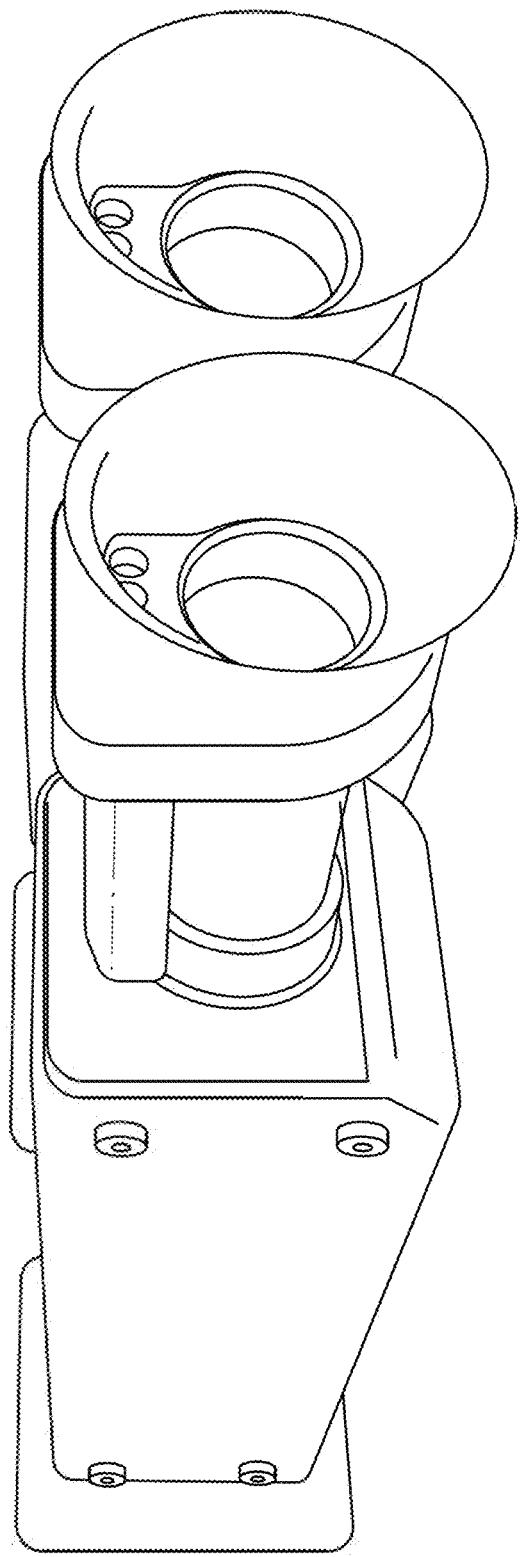
FIG. 35 is a perspective view of an exemplary light field refractor/phoropter combining side-by-side two of the units shown in FIGS. 34A and 34B for evaluating both eyes at the same time, in accordance with one embodiment.

In some embodiments, two light field phoropters 3001 may be combined side-by-side to independently measure the visual acuity of both left and right eye at the same time. An example is shown in FIG. 35, where two units corresponding to the embodiment of FIGS. 34A and 34B (used as an example only) are placed side-by-side or fused into a single device.

In some embodiments, a dedicated application, software or website may provide integration with third party patient data software. In some embodiments, the phoropter's software may be updated on-the-fly via a network connection and/or be integrated with the patient's smartphone app for updates and reminders.

In some embodiments, the dedicated application, software or website may further provide a remote, real-time collaboration platform between the eye professional and patient, and/or between different eye professionals. This may include interaction between different participants via video chat, audio chat, text messages, etc.

In some embodiments, light field phoropter 3001 may be self-operated or operated by an optometrist, ophthalmologist or other certified eye-care professional. For example, in some embodiments, a patient could use phoropter 3001 in the comfort of his/her own home.

Figure 36:
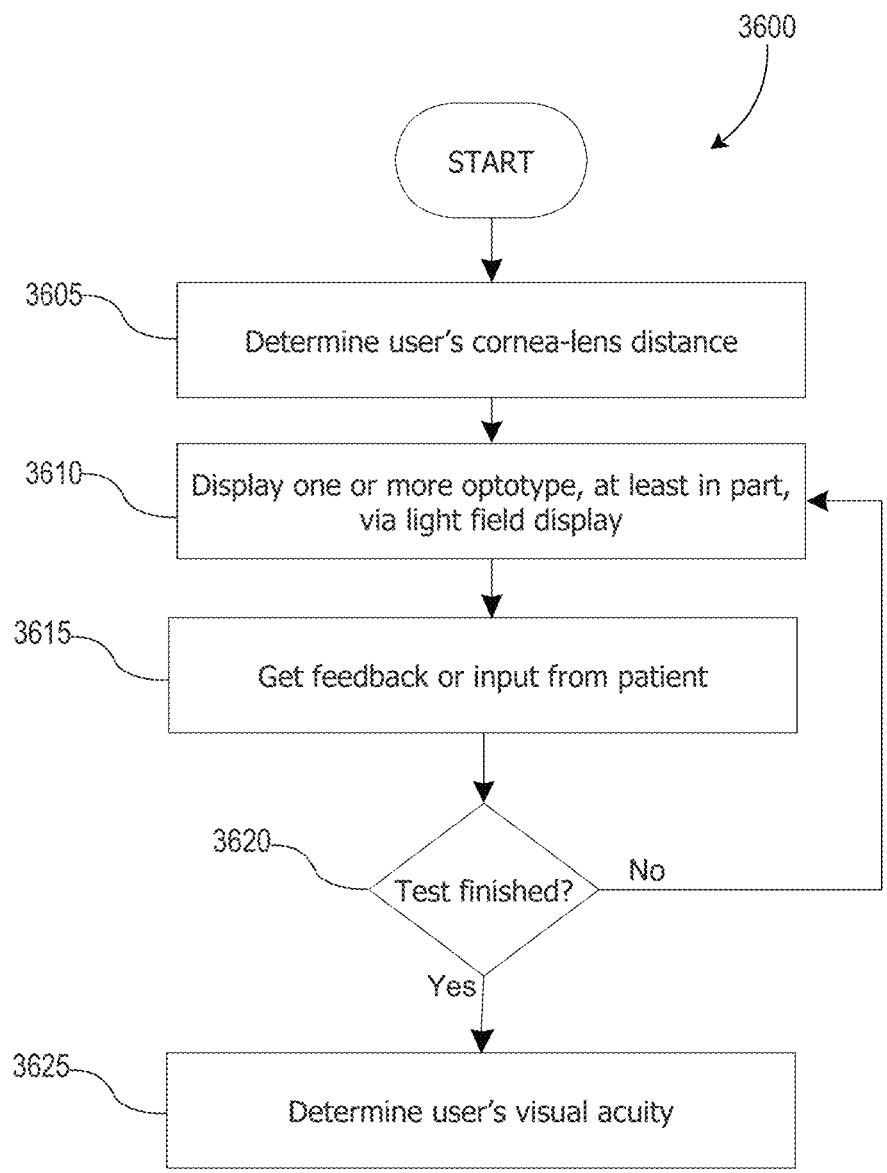
FIG. 36 is a process flow diagram of an exemplary dynamic subjective vision testing method, in accordance with one embodiment.

With reference to FIG. 36 and in accordance with different exemplary embodiments, a dynamic subjective vision testing method using vision testing system 3000, generally referred to using the numeral 3600, will now be described. As mentioned above, the use of a light field display enables phoropter 3001 of vision testing system 3000 to provide more dynamic and/or more modular vision tests than what is generally possible with traditional phoropters. Generally, method 3600 seeks to diagnose a patient's reduced visual acuity and produce therefrom, in some embodiments, an eye prescription or similar.

In some embodiments, eye prescription information may include, for each eye, one or more of: distant spherical, cylindrical and/or axis values, and/or a near (spherical) addition value.

In some embodiments, the eye prescription information may also include the date of the eye exam and the name of the eye professional that performed the eye exam. In some embodiments, the eye prescription information may also comprise a set of vision correction parameter(s) 201 used to operate any vision correction light field displays using the systems and methods described above. In some embodiments, the eye prescription may be tied to a patient profile or similar, which may contain additional patient information such as a name, address or similar. The patient profile may also contain additional medical information about the user. All information or data (i.e. set of vision correction parameter(s) 201, user profile data, etc.) may be kept on remote database 3059. Similarly, in some embodiments, the user's current vision correction parameter(s) may be actively stored and accessed from external database 3059 operated within the context of a server-based vision correction subscription system or the like, and/or unlocked for local access via the client application post user authentication with the server-based system.

Phoropter 3001 being, in some embodiments, portable, a large range of environment may be chosen to deliver the vision test (home, eye practitioner's office, etc.). At the start, the patient's eye may be placed at the required location. This is usually by placing his/her head on a headrest or by placing the objective (eyepiece) on the eye to be diagnosed. As mentioned above, the vision test may be self-administered or partially self-administered by the patient. For example, the operator (e.g. eye professional or other) may have control over the type of test being delivered, and/or be the person who generates or helps generate therefrom an eye prescription, while the patient may enter inputs dynamically during the test (e.g. by choosing or selecting an optotype, etc.).

As discussed above, the light field rendering method 3600 generally requires an accurate location of the patient's pupil center. Thus, at step 3605, such a location is acquired. In some embodiments, such a pupil location may be acquired via eye tracker 3009, either once, at intervals, or continuously. In other embodiments, the location may be derived from the device or system's dimension. For example, in some embodiments, the use an eye-piece or similar provides an indirect means of deriving the pupil location. In some embodiments, the phoropter 3001 may be self-calibrating and not require any additional external configuration or manipulation from the patient or the practitioner before being operable to start a vision test.

At step 3610, one or more optotypes is/are displayed to the patient, at one or more dioptric power (e.g. in sequence, side-by-side, or in a grid pattern/layout). The use of light field display 3003 offers multiple possibilities regarding how the optotypes are presented, and at which dioptric power each may be rendered. The optotypes may be presented sequentially at different dioptric power, via one or more dioptric power increments. In some embodiments, the patient and/or operator may control the speed and size of the dioptric power increments.

Figure 37:
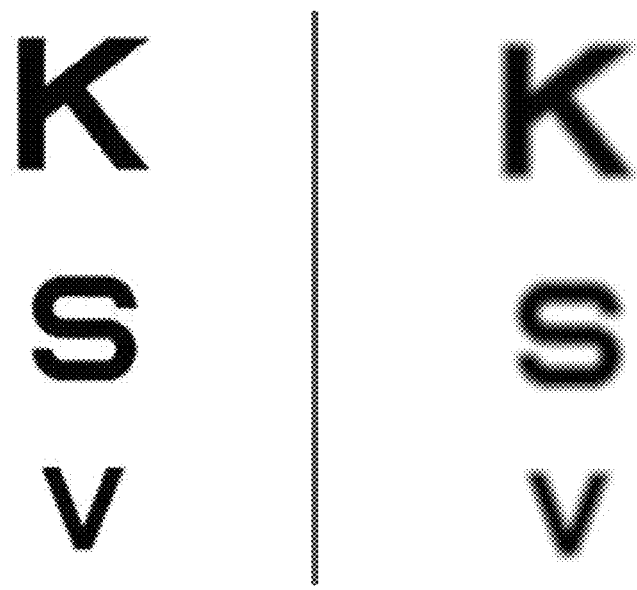
FIG. 37 is a schematic diagram of an exemplary light field image showing two columns of optotypes at different dioptric power for the method of FIG. 36, in accordance with one embodiment.

In some embodiments, optotypes may also be presented, at least in part, simultaneously on the same image but rendered at a different dioptric power (via ray-tracing methods 2400, or 2700, for example). For example, FIG. 37 shows an example of how different optotypes may be displayed to the patient but rendered with different dioptric power simultaneously. These may be arranged in columns or in a table or similar. In FIG. 37, we see two columns of three optotypes (K, S, V), varying in size, as they are perceived by a patient, each column being rendered at different degrees of refractive correction (e.g. dioptric power). In this specific example, the optotypes on the right are being perceived as blurrier than the optotypes on the left.

Thus, at step 3615, the patient would communicate/verbalize this information to the operator or input/select via control interface 3011 the left column as the one being clearer. Thus, in some embodiments, method 3600 may be configured to implement dynamic testing functions that dynamically adjust one or more displayed optotype's dioptric power in real-time in response to a designated input, herein shown by the arrow going back from step 3620 to step 3610. In the case of sequentially presented optotypes, the patient may indicate when the optotypes shown are clearer. In some embodiments, the patient may control the sequence of optotypes shown (going back and forth as needed in dioptric power), and the speed and increment at which these are presented, until he/she identifies the clearest optotype. In some embodiments, the patient may indicate which optotype or which group of optotypes is the clearest by moving an indicator icon or similar within the displayed image.

In some embodiments, the optotypes may be presented via a video feed or similar.

In some embodiments, when using a reel of lenses or similar, discontinuous changes in dioptric power may be unavoidable. For example, the reel of lenses may be used to provide a larger increment in dioptric power, as discussed above. Thus, step 3610 may in this case comprise first displaying larger increments of dioptric power by changing lens as needed, and when the clearest or less blurry optotypes are identified, fine-tuning with continuous or smaller increments in dioptric power using the light field display. In the case of optotypes presented simultaneously, the refractive components 3007 may act on all optotypes at the same time, and the change in dioptric power between them may be controlled only by the light display 3003. In some embodiments, for example when using an electrically tunable fluid lens or similar, the change in dioptric power may be continuous.

In some embodiments, eye images may be recorded during steps 3610 to 3620 and analyzed to provide further diagnostics. For example, eye images may be compared to a bank or database of proprietary eye exam images and analyzed, for example via an artificial intelligence (AI) or Machine-learning (ML) system or similar. This analysis may be done by phoropter 3001 locally or via a remote server or database 3059.

Once the correct dioptric power needed to correct for the patient's reduced visual acuity is defined at step 3625, an eye prescription or vision correction parameter(s) may be derived from the total dioptric power used to display the best perceived optotypes.

In some embodiments, the patient, an optometrist or other eye-care professional may be able to transfer the patient's eye prescription directly and securely to his/her user profile store on said server or database 3059. This may be done via a secure website, for example, so that the new prescription information is automatically uploaded to the secure user profile on remote database 3059. In some embodiments, the eye prescription may be sent remotely to a lens specialist or similar to have prescription glasses prepared.

In some embodiments, the vision testing system 3000 may also or alternatively be used to simulate compensation for higher-order aberrations. Indeed, the light field rendering methods 1100, 1900, 2400, or 2700 described above may be used to compensation for higher order aberrations (HOA), and thus be used to validate externally measured or tested HOA via method 3600, in that a measured, estimated or predicted HOA can be dynamically compensated for using the system described herein and thus subjectively visually validated by the viewer in confirming whether the applied HOA correction satisfactory addresses otherwise experienced vision deficiencies. In one such embodiment, a HOA correction preview can be rendered, for example, in enabling users to appreciate the impact HOA correction (e.g. HOA compensating eyewear or contact lenses, intraocular lenses (IOL), surgical procedures, etc.), or different levels or precisions thereof, could have on their visual acuity. Alternatively, HOA corrections once validated can be applied on demand to provide enhanced vision correction capabilities to consumer displays.

Higher-order aberrations can be defined in terms of Zernike polynomials, and their associated coefficients. In some embodiments, the light field phoropter may be operable to help validate or confirm measured higher-order aberrations, or again to provide a preview of how certain HOA corrections may lead to different degrees of improved vision. To do so, in some embodiments, the ray-tracing methods 1100, 1900, 2400, or 2700 may be modified to account for the wavefront distortion causing the HOA which are characterized by a given set of values of the Zernike coefficients. Such an approach may include, in some embodiments, extracting or deriving a set of light rays corresponding to a given wavefront geometry. Thus, the light field display may be operable to compensate for the distortion by generating an image corresponding to an "opposite" wavefront aberration. In some embodiments, the corresponding total aberration values may be normalized for a given pupil size of circular shape. Moreover, in some embodiments, the wavefront may be scaled, rotated and transformed to account for the size and shape of the view zones. This may include concentric scaling, translation of pupil center, and rotation of the pupil, for example.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

While the present disclosure describes various exemplary embodiments, the disclosure is not so limited. To the contrary, the disclosure is intended to cover various modifications and equivalent arrangements included within the general scope of the present disclosure.

What is claimed is:

1. A device to subjectively assess a user's reduced visual acuity, comprising:
   a digital display;
   a lenslet array disposed relative to said digital display to shape a light field emanating therefrom; and
   a hardware processor configured to operate on pixel data for respective optotypes to output respectively adjusted pixel data to be rendered side-by-side by said digital display via said lenslet array so to respectively adjust the user's perception of said respective optotypes as rendered therethrough to thereby render, side-by-side, distinctly perceptively adjusted optotypes corresponding to respective visual corrections to subjectively assess the user's reduced visual acuity.

2. The device of claim 1, further comprising an adjustable refractive optical system disposed relative to said digital display so to set a selectable common refractive correction and thus further refract and thus redirect said light field, wherein each of said respective visual corrections is further defined as a function of said selectable common refractive correction.

3. The device of claim 2, wherein said selectable common refractive correction is selectable to define a common coarse refractive correction for each of said respective optotypes, whereas said respectively adjusted pixel data further refines said respective visual corrections.

4. The device of claim 2, wherein said adjustable refractive optical system comprises a tunable lens.

5. The device of claim 1, wherein said respective optotypes comprise identical optotypes that are distinctly perceptively adjusted for subjective comparison.

6. The device of claim 1, wherein said respectively adjusted pixel data digitally maps each of said respective optotypes to a corresponding virtual image plane virtually positioned relative to the digital display at respectively corresponding perceived image depths.

7. The device of claim 1, wherein said respectively adjusted pixel data digitally maps each of said respective optotypes to a retinal plane in accordance with said respective visual corrections based on respective eye focus parameters.

8. The device of claim 1, wherein said distinctly perceptively adjusted optotypes are rendered side-by-side in respective quadrants.

9. The device of claim 1, wherein said distinctly perceptively adjusted optotypes are rendered side-by-side in a 2-dimensional grid.

10. The device of claim 1, wherein said respective visual corrections are dynamically variable so to subjectively assess the user's reduced visual acuity.

* * * * *